US006794510B2

(12) United States Patent
Le Bourdonnec et al.

(10) Patent No.: US 6,794,510 B2
(45) Date of Patent: Sep. 21, 2004

(54) PROCESSES FOR THE PREPARATION OF PERIPHERAL OPIOID ANTAGONIST COMPOUNDS AND INTERMEDIATES THERETO

(75) Inventors: Bertrand Le Bourdonnec, East Fallowfield Township, PA (US); Roland Ellwood Dolle, King of Prussia, PA (US)

(73) Assignee: Adolor Corporation, Exton, PA (US)

( * ) Notice: Subject to any disclaimer, the term of this patent is extended or adjusted under 35 U.S.C. 154(b) by 0 days.

(21) Appl. No.: 10/216,158

(22) Filed: Aug. 8, 2002

(65) Prior Publication Data

US 2004/0039205 A1 Feb. 26, 2004

(51) Int. Cl.[7] ...................... C07D 211/32; A61K 31/445
(52) U.S. Cl. ..................... 546/192; 514/331; 546/236
(58) Field of Search ................................ 546/192, 236; 514/331

(56) References Cited

U.S. PATENT DOCUMENTS

| | | | |
|---|---|---|---|
| 5,159,081 A | 10/1992 | Cantrell et al. | 546/226 |
| 5,250,542 A | 10/1993 | Cantrell et al. | 514/315 |
| 5,270,328 A | 12/1993 | Cantrell et al. | 514/331 |
| 5,434,171 A * | 7/1995 | Frank et al. | 514/331 |
| 6,451,806 B2 | 9/2002 | Farrar | 514/282 |
| 6,469,030 B2 | 10/2002 | Farrar et al. | 514/331 |

OTHER PUBLICATIONS

Barton, D.H.R., et al., "Improved methods for the radical deoxygenation of secondary alcohols," *Tetrahedron Lett.*, 1989, 30(20), 2619–2622.

Barton, D.H.R., et al., "On the mechanism of deoxygenation of secondary alcohols by tin hydride reduction of methyl xanthates and other thiocarbonyl derivatives," *Tetrahedron Lett.*, 1990 31(28), 3991–3994.

Boussaguet, P., et al., "Catalytic and supported barton— McCombie deoxygenation of secondary alcohols: a clean reaction," *Tetrahedron Lett.*, 2000, 41, 3377–3380.

Dorland's Illustrated Medical Dictionary, 27th Ed., W.B. Saunders Company, Philadelphia, PA, 1988, 816.

Dorland's Illustrated Medical Dictionary, 27th Ed., W.B. Saunders Company, Philadelphia, PA, 1988, 1995, 375.

Gevorgyan, V., et al., "A novel $B(C_6F_5)_3$–catalyzed reduction of alcohols and cleavage of aryl and alkyl ethers with hydrosilanes," *J. Org. Chem.*, 2000, 65, 6179–6186.

Lidstrom, P., et al., "Microwave assisted organic synthesis—a review," *Tetrahedron*, 2001, 57(45), 9225–9283.

Livingston, E.H., et al., "Postoperative ileus," *Digestive Diseases and Sciences*, Jan. 1990, 35(1), 121–132.

Perlmutter, P., et al., "Diastereoselection in the nucleophilic conjugate addition of amines to 2–hydroxyalkylpropenoates," *J. Org. Chem.*, 1988, 29(8), 949–952.

(List continued on next page.)

Primary Examiner—Rita Desai
(74) Attorney, Agent, or Firm—Washcock Washburn LLP

(57) ABSTRACT

Novel processes for the preparation of peripheral opioid antagonist compounds and intermediates thereto. The compounds prepared by the present processes may be useful, for example, as antagonists to the mu, kappa and delta opioid receptors, and thereby may be useful in the treatment of gastrointestinal motility disorders, and in preventing peripheral opiate induced side effects. The present processes may offer improved yields, purity, ease of preparation and/or isolation of intermediates and final product, and more industrially useful reaction conditions and workability.

14 Claims, 7 Drawing Sheets

OTHER PUBLICATIONS

Perlmutter, P., et al., "A simple route to α–substituted–β–amino ester precursors of carbapenem antibiotics," *J. Org. Chem.*, 1995, 60, 6515–6522.

Resnick, J., et al., "Delayed gastric emptying and postoperative ileus after nongastric abdominal surgery: Part 1," *J. Am. J. Gastroenterology*, 1997, 92(5), 751–762.

Resnick, J., et al., "Delayed gastric emptying and postoperative ileus after nongastric abdominal surgery: Part II," *J. Am. J. Gastroenterology*, 1997, 92(6), 934–940.

Sakai, T., et al., "$Me_3SiCl–NaI–CH_3CN$ as an efficient and practical reducing agent for benzylic alcohols," *Tetrahedron Lett.*, 1987, 28(33), 3817–3818.

Werner, J.A., et al., "Synthesis of trans–3, 4–dimethyl–4–(3–hydroxyphenyl)piperidine opioid antagonists: application of the Cis–thermal elimination of carbonates to alkaloid synthesis," *J. Org. Chem.*, 1996, 61, 587–597.

* cited by examiner

VII-I
MOR: Ki = 31.6 nM

VII-II
MOR: Ki = 30.6 nM

IIc-I
MOR: Ki = 32 nM

IIc-II
MOR: Ki = 12.5 nM

IId-I
MOR: Ki = 27 nM

IIa-I
MOR: Ki = 45 nM

IIb-I
MOR: Ki = 148 nM

US 6,794,510 B2

PROCESSES FOR THE PREPARATION OF PERIPHERAL OPIOID ANTAGONIST COMPOUNDS AND INTERMEDIATES THERETO

FIELD OF THE INVENTION

The present invention relates to novel processes for the preparation of peripheral opioid antagonist compounds, as well as intermediates thereof.

BACKGROUND OF THE INVENTION

The trans-3,4-dimethyl-4-(3-hydroxyphenyl)piperidines are an important class of compounds which exhibit opioid antagonist activity as a result of the 3-methyl substituent. Alvimopan (i.e., (+)-2-[(S)-benzyl-3-[4(R)-(3-hydroxyphenyl)-3(R),4-dimethylpiperidin-1-yl] propionamidolacetic acid), shown below, represents an example of this class of opioid antagonists. This compound is a peripherally-active antagonist which has a high affinity for the μ-opioid receptor in the lining of the gastrointestinal tract and is useful in the treatment of gastrointestinal motility disorders. See, e.g., U.S. Pat. Nos. 5,270,328; 5,250,542; 5,159,081; and 5,434,171.

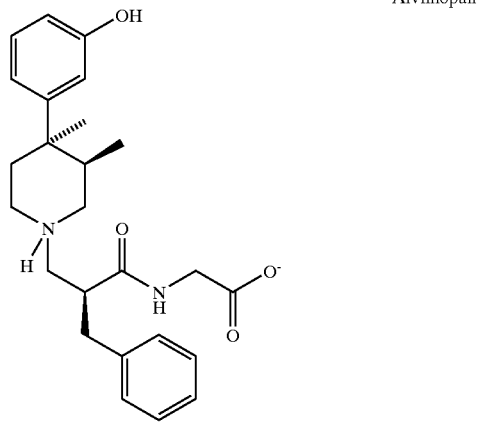

Alvimopan

A synthesis of Alvimopan, partially outlined in FIG. 1, has been described in Werner et al., *J. Org. Chem.*, 1996, 61, 587. The drug product was prepared in 12 steps and 6.2% yield from 1,3-dimethyl-4-piperidone as starting material. The synthesis includes the preparation of a (3R,4R)-3,4-dimethyl-4-(3-hydroxyphenyl)-piperidine nucleus (A), which was achieved in seven steps and 14.4% overall yield. While the next step, involving the Michael addition of (A) to methyl acrylate to produce intermediate (B), proceeds in good yield (96%), alkylation of the dianion of (B) with benzyl bromide proceeds with poor diastereoselectivity (47:53 mixture of the (3R,4R,αS)- and (3R,4R,αR)-isomers of the alkylation products, respectively). Consequently, the diastereomers require separation by recrystallization of their hydrochloride salts from methanol, resulting in low yields of intermediate (C) (34%). The poor diastereoselectivity of the alkylation step contributes to the low overall yield for the synthesis of Alvimopan.

In view of the importance of Alvimopan and related trans-3,4-dimethyl-4-(3-hydroxyphenyl)piperidine derivatives and intermediates in the treatment of gastrointestinal motility disorders and other conditions involving μ-opioid receptors, improved syntheses are needed. Such improvements may include, for example, one or more of the following: enhanced diastereoselectivity of individual reaction steps, increased product yields, use of lower cost starting materials, lowered energy consumption (e.g., avoidance of reactions conducted at very high or low temperatures or pressures), reduction in the number of synthetic steps, improved scale up conditions, and the like. The methods and compositions of the present invention are directed to these, as well as other important needs.

SUMMARY OF THE INVENTION

Accordingly, the present invention is directed, in part, to novel processes for preparing Alvimopan and related trans-3,4-dimethyl-4-(3-hydroxyphenyl)piperidine derivatives and intermediates thereto. Specifically, in one embodiment, there are provided processes for preparing a compound of Formula IIa, a compound of Formula IIb, or a mixture thereof:

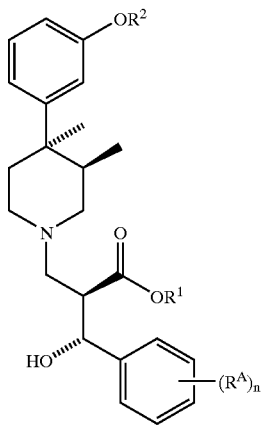

IIa

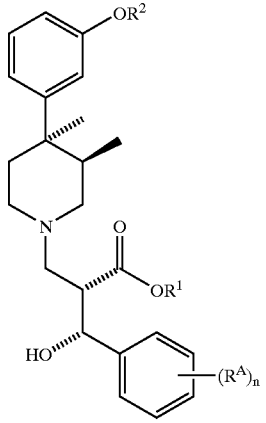

IIb wherein:
  each $R^1$ is, independently, H, alkyl, aryl, aralkyl, heteroaryl, or heterocyclyl;
  each $R^2$ is independently, H or a hydroxyl protecting group;
  each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
  n is 0 to 5;
  or a salt thereof;

comprising contacting a compound of Formula III:

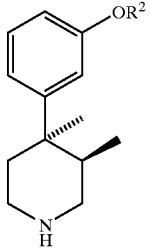

III with a compound of Formula IVa:

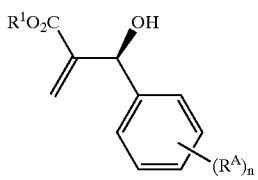

IVa for a time and under conditions effective to provide said compound of Formula IIa, compound of Formula IIb, or mixture thereof.

Another embodiment relates to processes for preparing a compound of Formula Va, a compound of Formula Vb, or a mixture thereof:

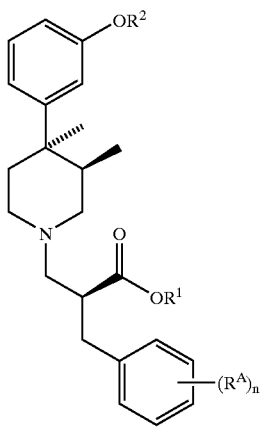

Va

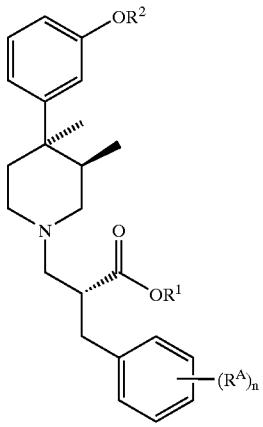

Vb wherein:

each $R^1$ is, independently, H, alkyl, aryl, aralkyl, heteroaryl, or heterocyclyl;

each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula IIa, a compound of Formula IIb, or a mixture thereof:

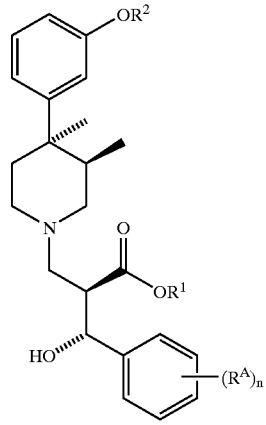

IIa

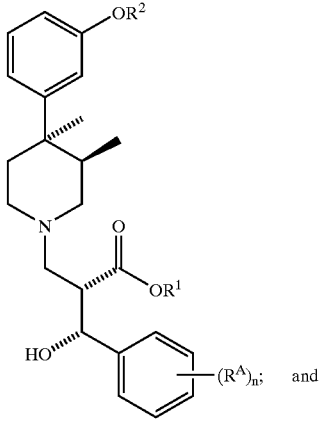

IIb and substituting the secondary hydroxyl group of said compound of Formula IIa, said compound of Formula IIb, or said mixture thereof with hydrogen to provide the compound of Formula Va, the compound of Formula Vb, or the mixture thereof.

Still another embodiment relates to processes for preparing a compound of Formula IIc, a compound of Formula IId, or a mixture thereof:

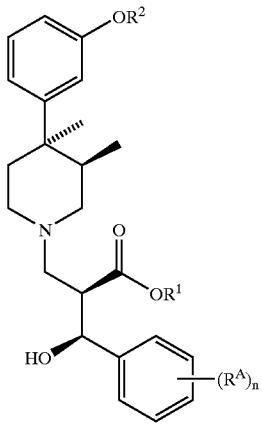
IIc

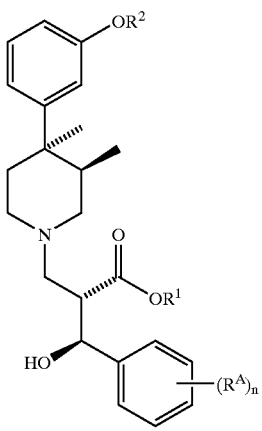
IId wherein:

each $R^1$ is, independently, H, alkyl, aryl, aralkyl, heteroaryl, or heterocyclyl;

each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

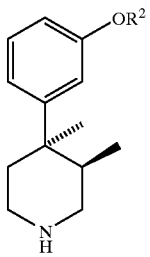
III with a compound of Formula IVb:

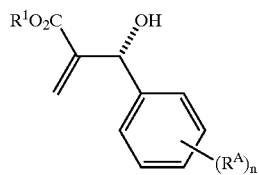
IVb for a time and under conditions effective to provide the compound of Formula IIc, the compound of Formula IId, or the mixture thereof.

Yet another embodiment relates to processes for preparing a compound of Formula Va, a compound of Formula Vb, or a mixture thereof:

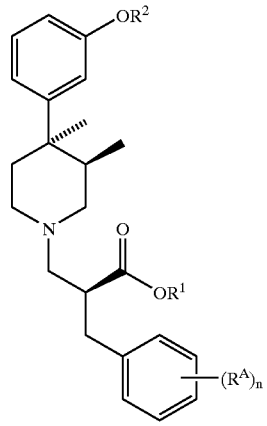
Va

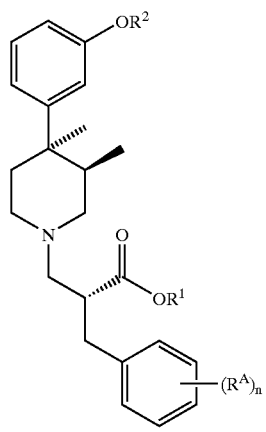
Vb wherein:

each $R^1$ is, independently, H, alkyl, aryl, aralkyl, heteroaryl, or heterocyclyl;

each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula IIc, a compound of Formula IId, or a mixture thereof:

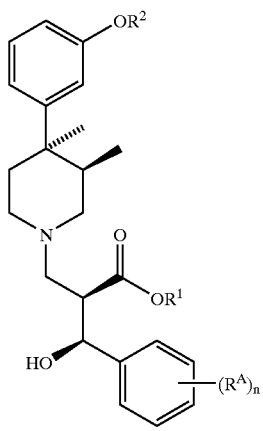

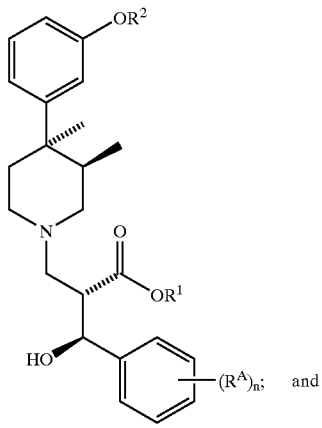

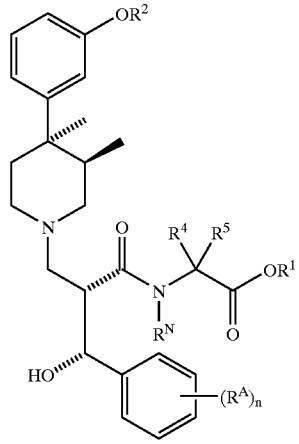

substituting the secondary hydroxyl group with hydrogen to provide the compound of Formula Va, the compound of Formula Vb, or the mixture thereof.

Another embodiment relates to processes for preparing a compound of Formula VIIa, a compound of Formula VIIb, or a mixture thereof:

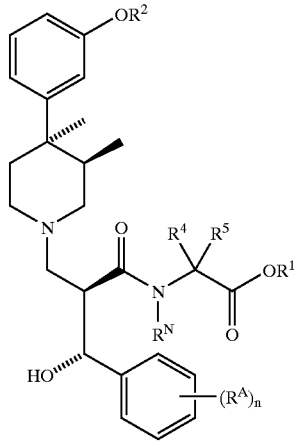

wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

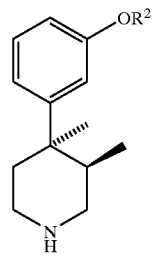

with a compound of Formula VIIIa:

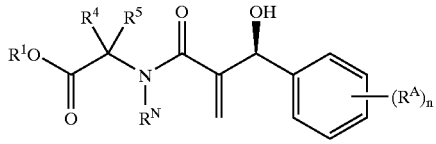

for a time and under conditions effective to provide said compound of Formula VIIa, said compound of Formula VIIb, or said mixture thereof.

Yet another embodiment relates to processes for preparing a compound of Formula IXa, a compound of Formula IXb, or a mixture thereof:

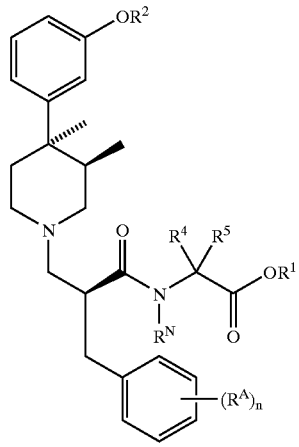

IXa

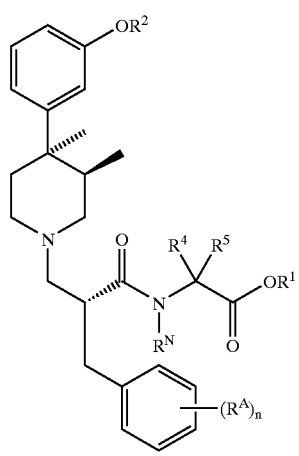

IXb wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula VIIa, a compound of Formula VIIb, or a mixture thereof:

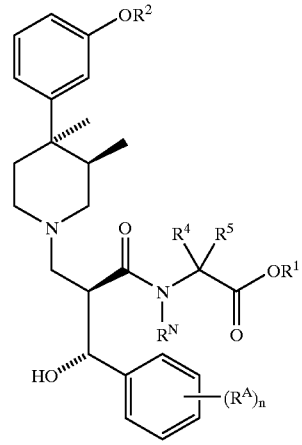

VIIa

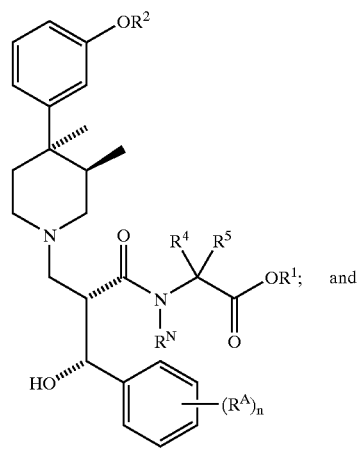

VIIb substituting the secondary hydroxyl group of said compound of Formula VIIa, said compound of Formula VIIb, or said mixture thereof with hydrogen to provide said compound of Formula IXa, said compound of Formula IXb, or said mixture thereof.

Still another embodiment relates to processes for preparing a compound of Formula VIIc, a compound of Formula VIId, or a mixture thereof:

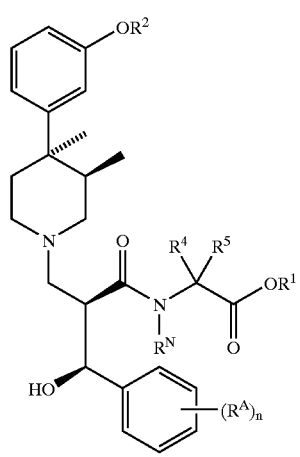

VIIc

-continued

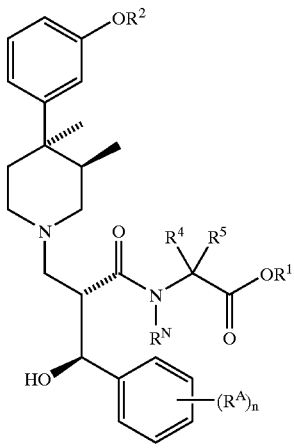

VIId wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

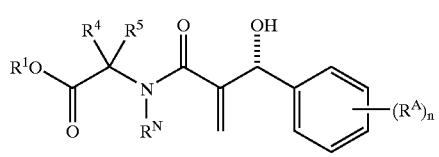

III with a compound of Formula VIIb:

VIIIb for a time and under conditions effective to provide said compound of Formula VIIc, said compound of Formula VIId, or said mixture thereof.

Another embodiment relates to processes for preparing a compound of Formula IXa, a compound of Formula IXb, or a mixture thereof:

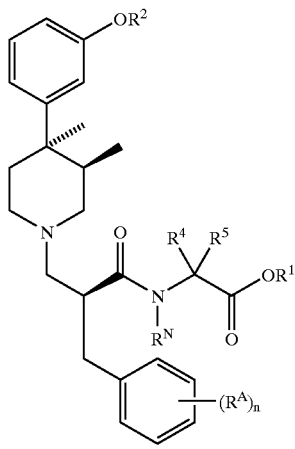

IXa

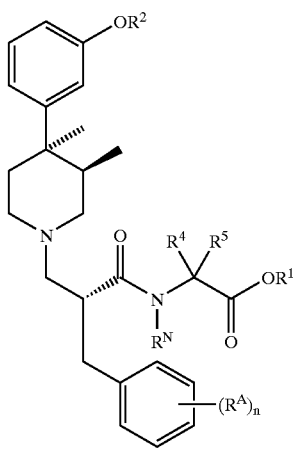

IXb wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula VIIc, a compound of Formula VIId, or a mixture thereof:

13

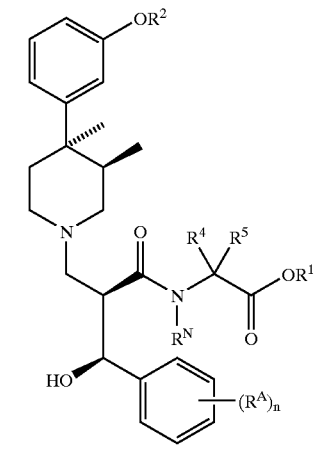

VIIc

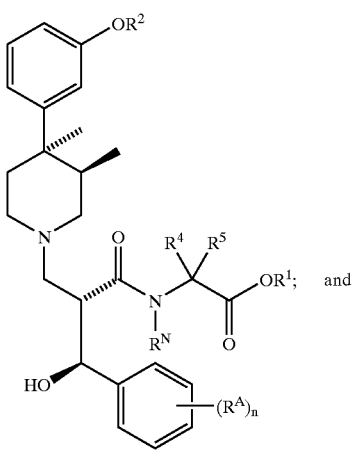

VIId

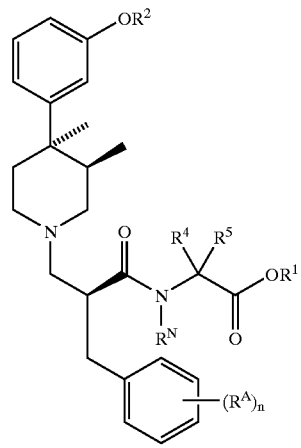

IXa substituting the secondary hydroxyl group with hydrogen to prepare said compound of Formula IXa, said compound of Formula IXb, or said mixture thereof.

Yet another embodiment of the invention relates to processes for preparing a compound of Formula IXa, a compound of Formula IXb, or a mixture thereof:

14

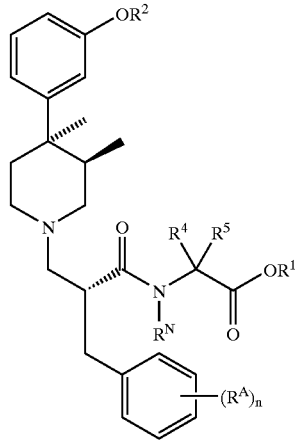

IXb wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, aryl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

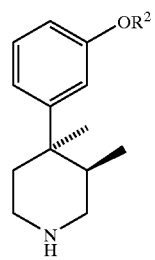

III with a compound of Formula XII:

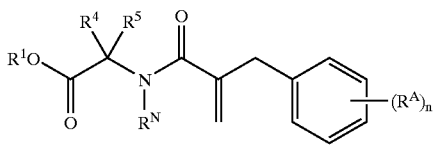

XII for a time and under conditions effective to prepare the compound of Formula IXa, the compound of Formula IXb, or the mixture thereof.

Another embodiment of the invention relates to compounds of Formula IIa:

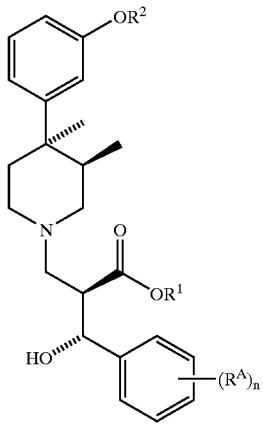

wherein:
 each $R^1$ is, independently, H, alkyl, aryl, aralkyl, heteroaryl, or heterocyclyl;
 each $R^2$ is, independently, H or a hydroxyl protecting group;
 each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
 n is 0 to 5;
 or a salt thereof.

Still another embodiment of the invention relates to compounds of Formula IIb:

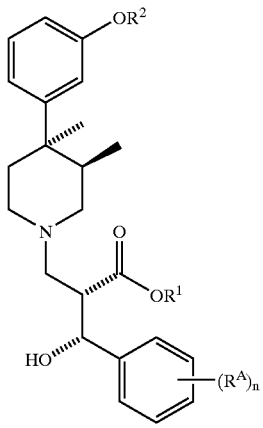

wherein:
 each $R^1$ is, independently, H alkyl, aryl, aralkyl, heteroaryl, or heterocyclyl;
 each $R^2$ is, independently, H or a hydroxyl protecting group;
 each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
 n is 0 to 5;
 or a salt thereof.

Yet another embodiment of the invention relates to compounds of Formula IIc:

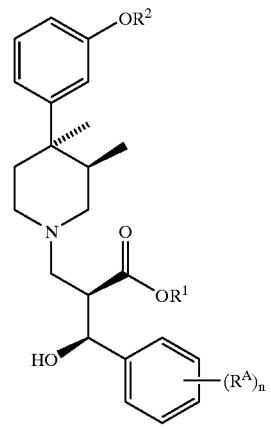

wherein:
 each $R^1$ is, independently, H, alkyl, aryl, aralkyl, heteroaryl, or heterocyclyl;
 each $R^2$ is, independently, H or a hydroxyl protecting group;
 each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
 n is 0 to 5;
 or a salt thereof.

Another embodiment of the invention relates to compounds of Formula IId:

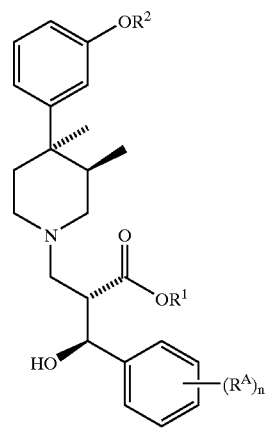

wherein:
 each $R^1$ is, independently, H, alkyl, aryl, aralkyl, heteroaryl, or heterocyclyl;
 each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Yet another embodiment of the invention relates to compounds of Formula VIa:

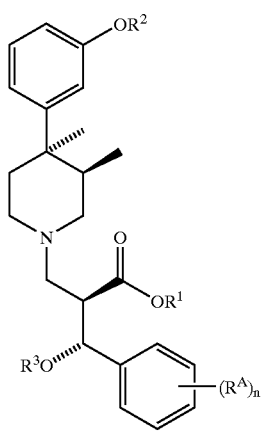

VIa wherein:

each $R^1$ is, independently, H, alkyl, aryl, aralkyl, heteroaryl, or heterocyclyl;

each $R^2$ is, independently, H or a hydroxyl protecting group;

each $R^3$ is, independently, a hydroxyl activating group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Another embodiment of the invention relates to compounds of Formula VIb:

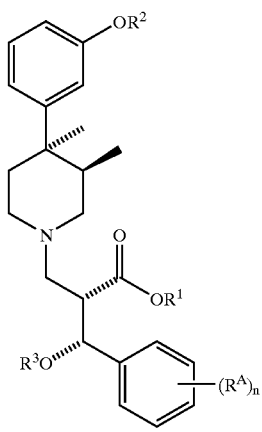

VIb wherein:

each $R^1$ is, independently, H, alkyl, aryl, aralkyl, heteroaryl, or heterocyclyl;

each $R^2$ is, independently, H or a hydroxyl protecting group;

each $R^3$ is, independently, a hydroxyl activating group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5; or a salt thereof.

Yet another embodiment of the invention relates to compounds of Formula VIc:

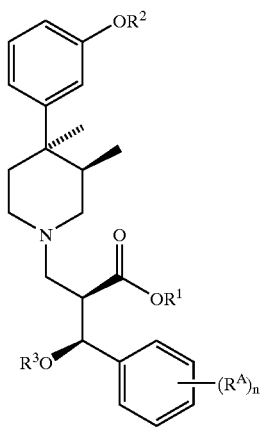

VIc wherein:

each $R^1$ is, independently, H, alkyl, aryl, aralkyl, heteroaryl, or heterocyclyl;

each $R^2$ is, independently, H or a hydroxyl protecting group;

each $R^3$ is, independently, a hydroxyl activating group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Still another embodiment of the invention relates to compounds of Formula VId:

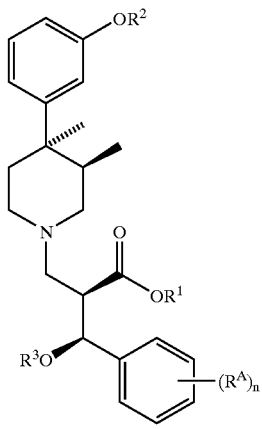

VId wherein:
- each R¹ is, independently, H, alkyl, aryl, aralkyl, heteroaryl, or heterocyclyl;
- each R² is, independently, H or a hydroxyl protecting group;
- each R³ is, independently, a hydroxyl activating group;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and
- n is 0 to 5;

or a salt thereof.

Another embodiment of the invention relates to compounds of Formula XIa:

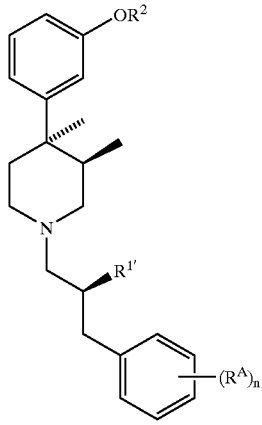

XIa wherein:
- each R¹' is, independently, —C(O)X, and X is halo, —OR¹, or —OC(O)R¹;
- each R¹ is, independently, H, alkyl, aryl, aralkyl, heteroaryl, or heterocyclyl;
- each R² is, independently, a hydroxyl protecting group;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and
- n is 0 to 5;

or a salt thereof.

Yet another embodiment of the invention relates to compounds of Formula XIb:

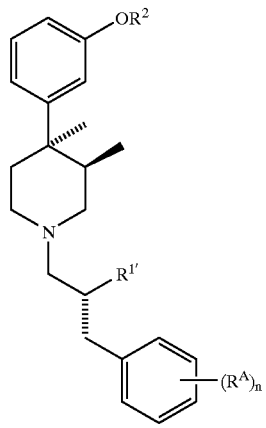

XIb wherein:
- each R¹' is, independently, —C(O)X, and X is halo, —OR¹, or —OC(O)R¹;
- each R¹ is, independently, H, alkyl, aryl, aralkyl, heteroaryl, or heterocyclyl;
- each R² is, independently, a hydroxyl protecting group;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and
- n is 0 to 5;

or a salt thereof.

Still another embodiment of the invention relates to compounds of Formula VIa:

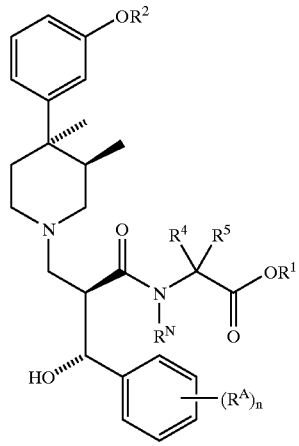

VIIa wherein:
- each R¹ is, independently, H, alkyl, aryl, aralkyl, heteroaryl, or heterocyclyl;
- each R² is, independently, H or a hydroxyl protecting group;
- each R⁴, R⁵, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Another embodiment of the invention relates to compounds of Formula VIIb:

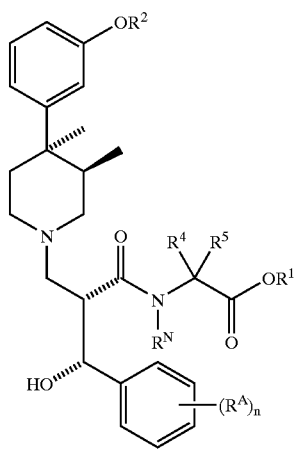

VIIb wherein:
each $R^1$ is, independently, H, alkyl, aryl, aralkyl, heteroaryl, or heterocyclyl;
each $R^2$ is, independently, H or a hydroxyl protecting group;
each $R^4$, $R^5$, and $R^N$ is, independently, H, alkyl, or aralkyl;
each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Yet another embodiment of the invention relates to compounds of Formula VIIc:

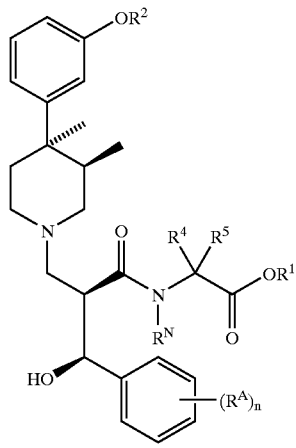

VIIc wherein:
each $R^1$ is, independently, H, alkyl, aryl, aralkyl, heteroaryl, or heterocyclyl;
each $R^2$ is, independently, H or a hydroxyl protecting group;
each $R^4$, $R^5$, and $R^N$ is, independently, H, alkyl, or aralkyl;
each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Still another embodiment of the invention relates to compounds of Formula VIId:

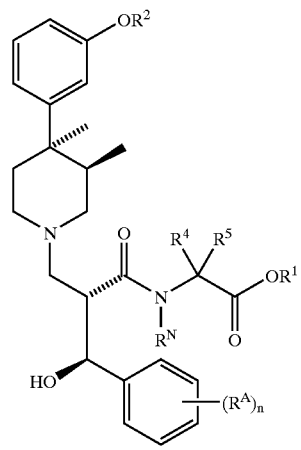

VIId wherein:
each $R^1$ is, independently, H, alkyl, aryl, aralkyl, heteroaryl, or heterocyclyl;
each $R^2$ is, independently, H or a hydroxyl protecting group;
each $R^4$, $R^5$, and $R^N$ is, independently, H, alkyl, or aralkyl;
each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Another embodiment of the invention relates to compounds of Formula VIIIa:

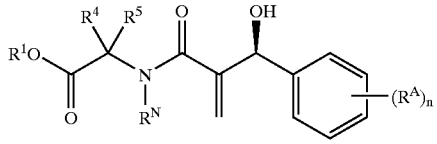

VIIIa wherein:
each $R^1$ is, independently, H, alkyl, aryl, aralkyl, heteroaryl, or heterocyclyl;
each $R^4$, $R^5$, and $R^N$ is, independently, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Still another embodiment relates to compounds of of Formula VIIIb:

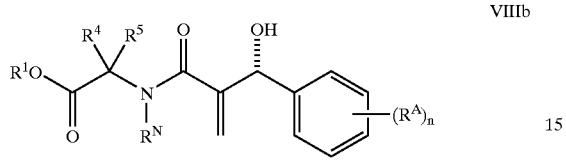

VIIIb wherein:
- each $R^1$ is, independently, H, alkyl, aryl, aralkyl, heteroaryl, or heterocyclyl;
- each $R^4$, $R^5$, and $R^N$ is, independently, H, alkyl, or aralkyl;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl and
- n is 0 to 5;

or a salt thereof.

Another embodiment of the invention relates to compounds of Formula Xa:

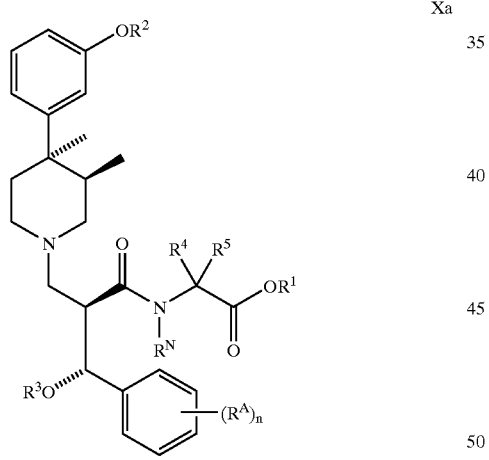

Xa wherein:
- each $R^1$ is, independently, H, alkyl, aryl, aralkyl, heteroaryl, or heterocyclyl;
- each $R^2$ is, independently, H or a hydroxyl protecting group;
- each $R^3$ is, independently, a hydroxyl activating group;
- each $R^4$, $R^5$, and $R^N$ is, independently, H, alkyl, or aralkyl;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
- n is 0 to 5;

or a salt thereof.

Still another embodiment of the invention relates to compounds of Formula Xb:

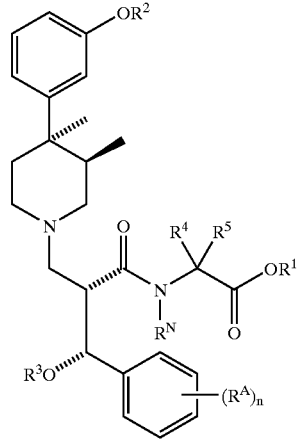

Xb wherein:
- each $R^1$ is, independently, H, alkyl, aryl, aralkyl, heteroaryl, or heterocyclyl;
- each $R^2$ is, independently, H or a hydroxyl protecting group;
- each $R^3$ is, independently, a hydroxyl activating group;
- each $R^4$, $R^5$, and $R^N$ is, independently, H, alkyl, or aralkyl;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
- n is 0 to 5;

or a salt thereof.

Another embodiment of the invention relates to compounds of Formula Xc:

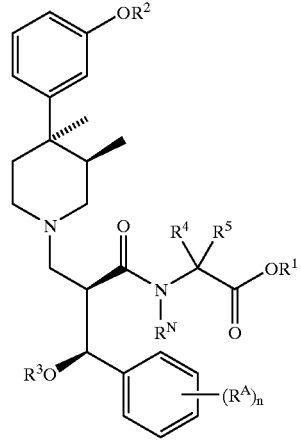

Xc wherein:
- each $R^1$ is, independently, H, alkyl, aryl, aralkyl, heteroaryl, or heterocyclyl;
- each $R^2$ is, independently, H or a hydroxyl protecting group;
- each $R^3$ is, independently, a hydroxyl activating group;
- each $R^4$, $R^5$, and $R^N$ is, independently, H, alkyl, or aralkyl;
- each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

Yet another embodiment of the invention relates to compounds of Formula Xd:

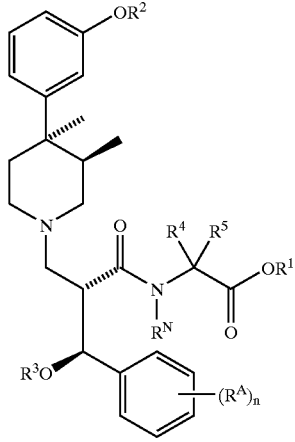

Xd wherein:
each R$^1$ is, independently, H, alkyl, aryl, aralkyl, heteroaryl, or heterocyclyl;
each R$^2$ is, independently, H or a hydroxyl protecting group;
each R$^3$ is, independently, a hydroxyl activating group;
each R$^4$, R$^5$, and R$^N$ is, independently, H, alkyl, or aralkyl;
each R$^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
n is 0 to 5;
or a salt thereof.

Still another embodiment of the invention relates to compounds of Formula IXa:

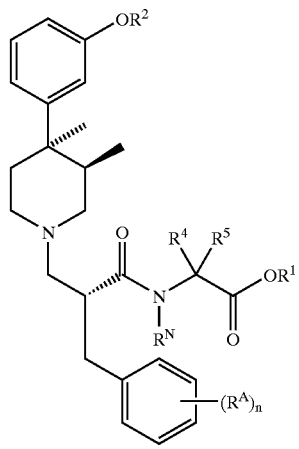

IXa wherein:
each R$^1$ is, independently, H, alkyl, aryl, aralkyl, heteroaryl, or heterocyclyl;

each R$^2$ is, independently, H a hydroxyl protecting group;
each R$^4$, R$^5$, and R is, independently, H, alkyl, or aralkyl;
each R$^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
n is 0 to 5;
or a salt thereof.

Still another embodiment of the invention relates to compounds of Formula IXb:

IXb wherein:
each R$^1$ is, independently, H, alkyl, aryl, aralkyl, heteroaryl, or heterocyclyl;
each R$^2$ is, independently, H a hydroxyl protecting group;
each R$^4$, R$^5$, and R$^N$ is, independently, H, alkyl, or aralkyl;
each R$^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
n is 0 to 5;
or a salt thereof.

Yet another embodiment of the invention relates to compounds of Formula XII:

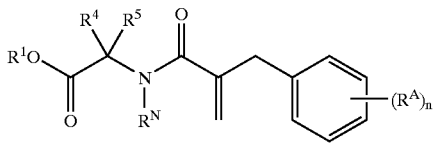

XII wherein:
each R$^1$ is, independently, H, alkyl, aryl, aralkyl, heteroaryl, or heterocyclyl;
each R$^2$ is, independently, H or a hydroxyl protecting group;
each R$^4$, R$^5$, and R$^N$ is, independently, H, alkyl, or aralkyl;
each R$^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO₂NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

DETAILED DESCRIPTION OF PREFERRED EMBODIMENTS

Figure 1:
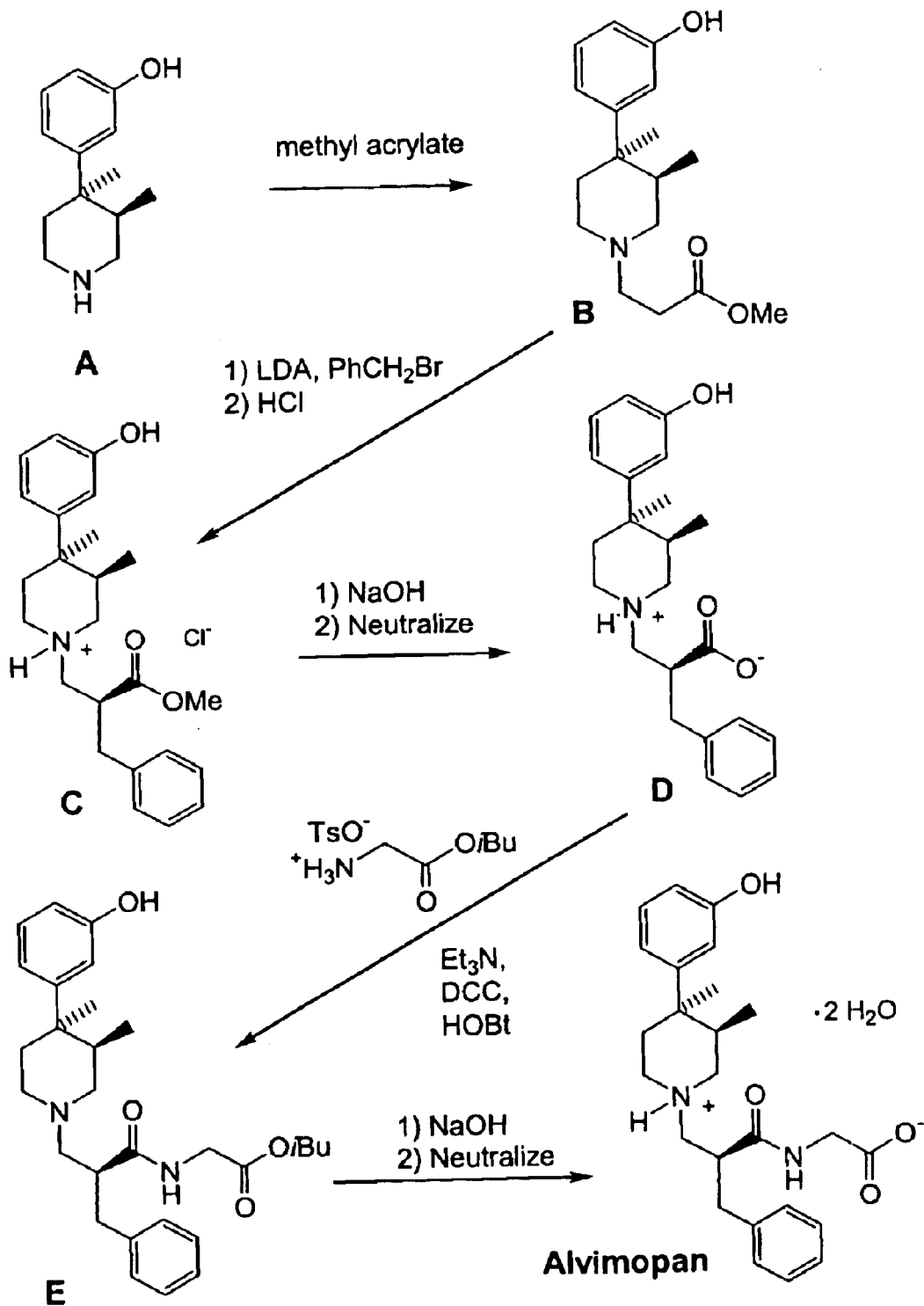
FIG. 1 shows a scheme for the synthesis of Alvimopan according to the prior art.

As used herein, the term "contacting" refers to the bringing together of compounds to within distances that allow for intermolecular interactions and chemical transformations accompanying such interactions. Often, contacting compounds are in solution phase.

As used herein, "alkyl" refers to a saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. Alkyl groups can be substituted or unsubstituted.

As used herein, "alkenyl" refers to an alkyl group having one or more double bonds.

As used herein, "alkynyl" refers to an alkyl group having one or more triple bonds.

As used herein, "aryl" refers to a mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. Aryl groups can be substituted or unsubstituted.

As used herein, "aralkyl" refers to aryl-substituted alkyl radicals having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl. Aralkyl groups can be substituted or unsubstituted.

As used herein, "heteroaryl" refers to a mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups can be substituted or unsubstituted.

As used herein, "heterocyclyl" refers to a mono-, di-, tri-, or other multicyclic aliphatic ring system that includes at least one, and preferably from 1 to about 4 sulfur, oxygen, or nitrogen heteroatom ring members. Heterocyclyl groups can have from about 3 to about 20 carbon atoms (and all combinations and subcombinations of ranges and specific numbers of carbon atoms therein), with from about 4 to about 10 carbons being preferred. The heterocyclyl group can also comprise unsaturations, and can also be fused to aromatic rings. Examples of heterocyclyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, and imidazolidinyl. Heterocyclyl groups can be substituted or unsubstituted.

As used herein, "silyl" refers to a group having the formula SiR'₃ where each R' is, independently, H, alkyl, aryl, aralkyl.

As used herein, "alkylcarbonyl" refers to an alkyl-C(=O)— group.

As used herein, "arylcarbonyl" refers to an aryl-C(=O)— group.

As used herein, "aralkylcarbonyl" refers to an aralkyl-C(=O)— group.

As used herein, "heteroarylcarbonyl" refers to a heteroaryl-C(=O)— group.

As used herein, "heterocyclylcarbonyl" refers to a heterocyclyl-C(=O)— group.

As used herein, "carboxyl" refers to a —C(=O)—OH group.

Typically, substituted chemical moieties include one or more substituents that replace hydrogen. Exemplary substituents include, for example, halo (e.g, F, Cl, Br, I), alkyl, alkenyl, alkynyl, aralkyl, aryl, heteroaryl, heterocyclyl, hydroxyl (OH), nitro (NO₂), cyano (CN), cyanato (CNO), thiocyanato (SCN), amino (e.g., NH₃ NHR", NR"₂), azido (N₃), carboxyl (COOH), C(O)R", OR", C(O)OR", NHC(O)R", aminocarbonyl, thiol, thiolato (SR"), sulfonic acid (SO₃H), phosphonic acid (PO₃H), SO₂R", phosphino (PH₂, PHR", PR"₂), silyl (SiR"₃, SiHR"₂, SiH₂R", SiH₃) and the like. In relation to the aforementioned substituents, each moiety R" can be, independently, any of H, alkyl, aryl, aralkyl, heteroaryl, or heterocyclyl, for example.

As used herein, the phrase "protecting group" refers to a moiety that renders a chemical functionality of a molecule inert to specific reaction conditions. The protecting group can later be removed from such functionality in a molecule, preferably without altering or substantially altering the remainder of the molecule. Protecting groups are well known in the art and are well described, for example, in Greene, T. W., et al., *Protecting Groups in Organic Synthesis* 2nd edition, John Wiley and Sons, Inc., New York, (1991), the disclosure of which is incorporated herein by reference in its entirety.

Accordingly, the phrase "hydroxyl protecting group" refers to a chemical moiety that renders a hydroxyl group inert to certain reaction conditions, such as reaction conditions designed to alter or change the molecule containing the hydroxyl group at a location other than the hydroxyl group. Hydroxyl protecting groups typically replace the hydrogen of the hydroxyl group and can be removed under conditions that do not substantially affect the remainder of the molecule. Exemplary hydroxyl protecting groups include, for example, alkyl, aryl, aralkyl, heteroaryl, heterocyclyl, alkylcarbonyl, arylcarbonyl, aralkylcarbonyl, heteroarylcarbonyl, heterocyclylcarbonyl, or silyl groups.

The phrase "activating group" refers to a moiety that renders a chemical functionality more sensitive to modification under certain reaction conditions. For example, an activating group may convert a poor leaving group into a good leaving group or increase (or decrease) susceptibility to nucleophilic atack or other chemical transformations.

Accordingly, the phrase "hydroxyl activating group" refers to a moiety that replaces the hydrogen of the hydroxyl group, thereby altering the chemical and electronic properties of the hydroxyl group such that the hydroxyl group is more susceptible to removal, such as by replacement with hydrogen or a moiety other than a hydroxyl group. Exemplary hydroxyl activating groups include, for example, alkyl, aryl, aralkyl, heteroaryl, heterocyclyl, alkylcarbonyl, arylcarbonyl, aralkylcarbonyl, heteroarylcarbonyl, heterocyclylcarbonyl, C(S)O-aryl, C(S)O-alkyl, or silyl.

The phrase "carboxyl activating group" is meant to refer to a moiety that replaces the hydrogen or hydroxyl of a carboxyl group, thereby altering the chemical and electronic properties of the carboxyl group such that the carboxyl group is more susceptible to nucleophilic attack or substitution. In embodiments in which the hydrogen of the carboxyl group is replaced, exemplary carboxyl activating groups include, for example, alkyl, aryl, aralkyl, heteroaryl, heterocyclyl, alkylcarbonyl, arylcarbonyl, aralkylcarbonyl, heteroarylcarbonyl, heterocyclylcarbonyl, C(S)O-aryl, C(S)O-alkyl, silyl or substituted alkylcarbonyl. An example of an aryl carboxyl activating group is pentahalophenyl, such as pentafluorophenyl, and an example of an alkylcarbonyl carboxyl activating group is acetyl or trifluoroacetyl. The carboxyl activating groups may be optionally substituted. An example of a substituted carboxyl activating group is substituted alkylcarbonyl, for example, carboxyl substituted alkylcarbonyl, such as succinyl (3-carboxylpropionyl).

In accordance with the present invention, certain types of carboxyl activation in which the hydrogen of the —C(=O)—OH group is replaced may also involve the use of coupling agents. As used herein, "coupling agents" refer to moieties that act to assist or promote the coupling of, or to improve the rate of the coupling of, carboxylate groups with compounds having reactive functionalities, for example, nucleophiles, including amino groups such as in the formation of amido functionality. Coupling agents are well known to one ordinarily skilled in the art and are described, for example, in Larock, R. C., *Comprehensive Organic Transformations*, VCH Publishers, Inc., NY (1989), and Carey, F. A., and Sundberg, R. J., *Advanced Organic Chemistry*, 3$^{rd}$ Edition, Plenum Press, NY (1990), the disclosures of each of which are hereby incorporated herein by reference in their entireties. A non-limiting example of a coupling agent that may be suitable for use in embodiments of the present invention is 1,3-dicyclohexylcarbodiimide (DCC), commercially available from Aldrich Chemical Company, Milwaukee, Wis., USA.

In embodiments in which the hydroxyl of the carboxyl group is replaced, the hydroxyl may be replaced by a moiety such as halo that alters the chemical and electronic properties of the carboxyl group, thereby rendering the resultant carbonyl compound, such as carboxylic acid halide more susceptible to nucleophilic attack or substitution. Exemplary carboxyl activating groups wherein the hydroxyl is replaced include, for example, halo, such as fluoro, chloro, bromo or iodo. The thus activated resultant carbonyl compound may be generated in situ, or may be provided in isolated form, as appropriate.

As used herein, "side effect" refers to a consequence other than the one(s) for which an agent or measure is used, as the adverse effects produced by a drug, especially on a tissue or organ system other then the one sought to be benefitted by its administration. In the case, for example, of opioids, the term "side effect" may preferably refer to such conditions as, for example, constipation, nausea and/or vomiting.

As used herein, "effective amount" refers to an amount of a compound as described herein that may be therapeutically effective to inhibit, prevent or treat the symptoms of particular disease, disorder or side effect. Such diseases, disorders and side effects include, but are not limited to, ileus and those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount", when used in connection with opioids, for example, for the treatment of pain, refers to the treatment and/or prevention of the painful condition. The term "effective amount", when used in connection with peripheral mu opioid antagonist compounds, refers to the treatment and/or prevention of side effects typically associated with opioids including, for example, such side effects as constipation, nausea and/or vomiting.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound which has been prepared by the addition of an acid. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base and zwitterions, are contemplated to be within the scope of the present invention.

"Patient" refers to animals, including mammals, preferably humans.

When any variable occurs more than one time in any constituent or in any formula, its definition in each occurrence is independent of its definition at every other occurrence. Thus, for example, if a group is shown to be substituted with, for example, 0 to 5 $R^A$, then said group may optionally be substituted with up to five $R^A$, and $R^A$ at each occurrence is selected independently from the defined list of possible $R^A$. Combinations of substituents and/or variables are permissible only if such combinations result in stable compounds.

When any variable occurs more than one time in any two or more diastereomers of a mixture, or in any two or more reactants of a process, its definition in each occurrence is independent of its definition at every other occurrence. Thus, for example, if one constituent of a mixture of diastereomers is shown to bear an R group, where $R^1$ is, for example, methyl, then other constituents of said mixture of diastereomers may each bear, independently, $R^1$ groups that are the same as, or different from, the R1 of the first constituent, so long as they are selected from the defined list of $R^1$. Further, for example, if one reactant of a process is shown to bear an $R^1$ group, where $R^1$ is, for example, methyl, then other reactants of said process may each bear, independently, $R^1$ groups that are the same as, or different from, the R1 of the first reactant, so long as they are selected from the defined list of $R^1$. Combinations of substituents and/or variables are permissible only if such combinations result in stable compounds.

The processes and synthetic methods described hereinthroughout may be carried out in any suitable solvent. Generally, suitable solvents are solvents which are substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular work-up following the reaction may be selected.

In certain embodiments, the diastereoselectivity of a reaction may be controlled or affected by the type of solvent employed, such as a protic solvent or an aprotic solvent. Protic solvents include, for example, water and alcohols such as methanol, ethanol, propanols, including n-propanol and isopropanol, butanols, including 1-butanol, 2-butanol, i-butanol, and t-butanol, substituted ethanols, including 2-nitroethanol, 2-fluoroethanol, 2,2,2-trifluoroethanol, 2-methoxyethanol and 2-ethoxyethanol, polyols, including ethylene glycol and diethylene glycol, pentanols, including 1-, 2-, or 3-pentanol, neo-pentanol, and t-pentanol, ethers, including monomethyl ether and diethylene glycol monoethyl ether, cyclic alcohols, including cyclohexanol, aromatic alcohols, including benzyl alcohol and phenol, and glycerol, to name a few.

Aprotic solvents include, for example, hydrocarbon solvents, and halogenated derivatives thereof, such as cyclohexane, pentane, toluene, benzene, cycloheptane, methylcyclohexane, ethylbenzene, m-, o-, or p-xylene, octane, indane, nonane, and the like. Aprotic solvents further include ethers, such as diethyl ether, dimethoxymethane, tetrahydrofuran (THF), 1,3-dioxane, 1,4-dioxane, furan, ethylene glycol dimethyl ether, ethylene glycol diethyl ether, diethylene glycol dimethyl ether, diethylene glycol diethyl ether, trieithylene glycol diisopropyl ether, anisole, or t-butylmethyl ether. Other aprotic solvents include, for example, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methyl-pyrrolidinone (NMP), formamide, N-methylacetamide, N-methylformamide, acetonitrile (MeCN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

In accordance with certain embodiments of the present invention, processes described herein may be carried out such that contacting of compounds and reagents occurs in the presence of microwave energy. Microwave technology may help increase reaction rates of various addition reactions such as, for example, Michael addition and related reactions. The use of microwaves in accelerating reaction rates is well known in the art of synthetic organic chemistry, and is described, for example, in Lidstrom, et al. *Tetrahedron*, 2001, 57(45), 9225–9283, the disclosure of which is hereby incorporated herein by reference in its entirety.

Compounds described hereinthroughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts.

It is well known in the art that compounds containing both amino and carboxyl groups often exist in equilibrium with their zwitterionic forms. Thus, any of the compounds described hereinthroughout that contain, for example, both amino and carboxyl groups, also include reference to their corresponding zwitterions.

Processes of the present invention may yield mixtures of diastereomers. Thus, in some embodiments, processes may, if desired, include a separation step to isolate diastereomers. Methods for separation of diastereomers are well known in the art and include, for example, chiral column chromatography, HPLC, recrystallization, or classical resolution methods involving selective reactivity.

In preferred form, the processes and intermediates of the present invention provide for improved syntheses of Alvimopan and related compounds, such as intermediates, diastereomers, and salts of Alvimopan. More particularly, the present methods may, for example, desirably eliminate or replace the inefficient step of transforming B to C (see FIG. 1), advantageously resulting in higher overall yields, improved diastereoselectivity, and the like. Accordingly, the present methods and intermediates generally pertain to the modification of piperidine intermediates (see, e.g., intermediate C in FIG. 1). For example, conjugate addition of piperidine intermediates to 2-(α-hydroxy)aryl acrylates (e.g., addition of compound 2 to compound 1a of FIG. 2) may proceed with high diastereoselectivity depending on the solvent in which the reaction is carried out. Reactions showing similar solvent dependencies have been reported in Perlmutter, et al, *J. Org. Chem.*, 1995, 60, 6515 and Perlmutter, et al., *Tetrahedron Lett.*, 1988, 29, 949, the disclosure of which are hereby incorporated herein by reference in their entireties.

Figure 2:
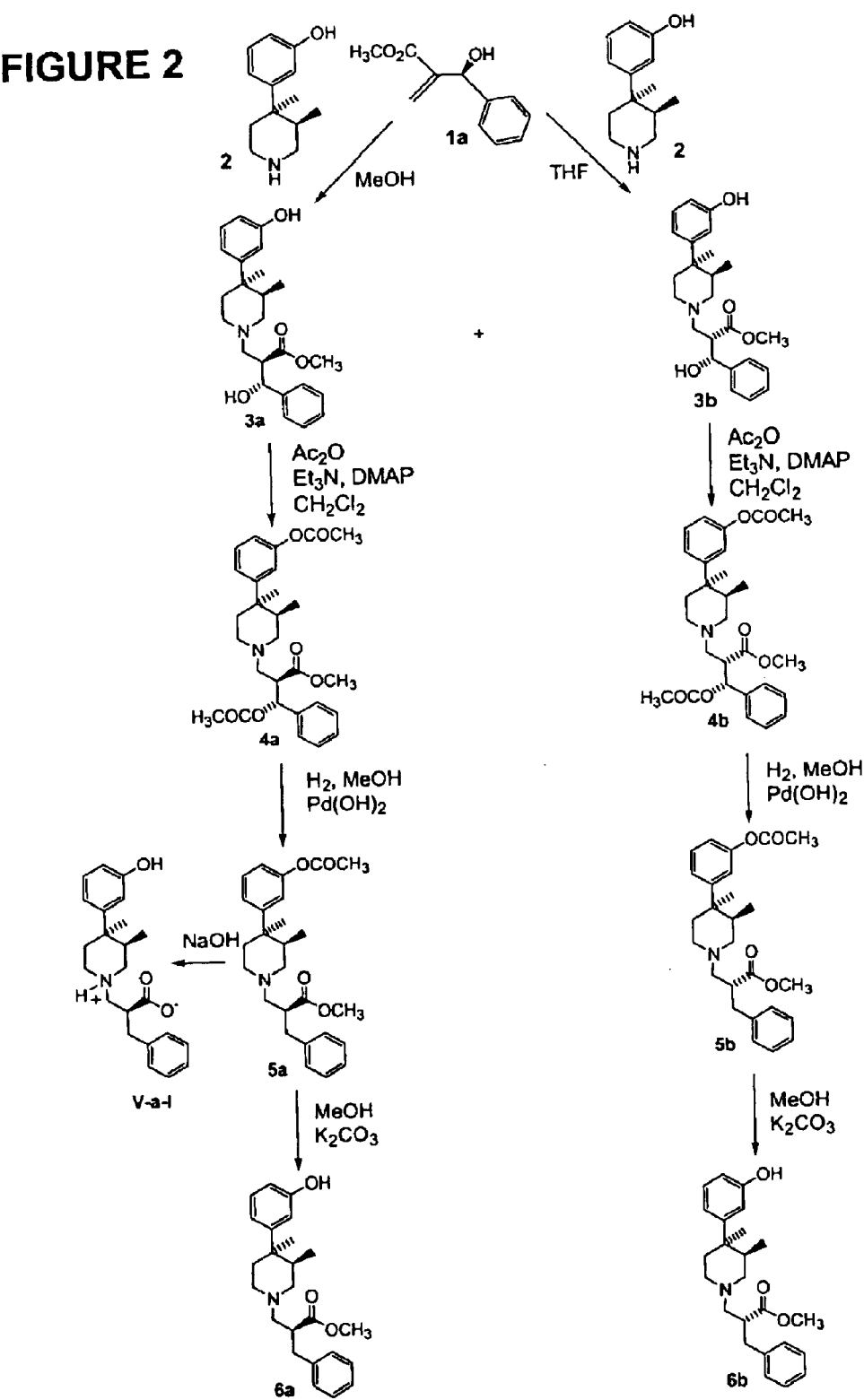
FIGS. 2 to 6 show schemes for the synthesis of compounds in accordance with embodiments of the present invention.

Accordingly, in one embodiment, the present invention provides processes for preparing compounds of Formula IIa, Formula IIb, and mixtures thereof:

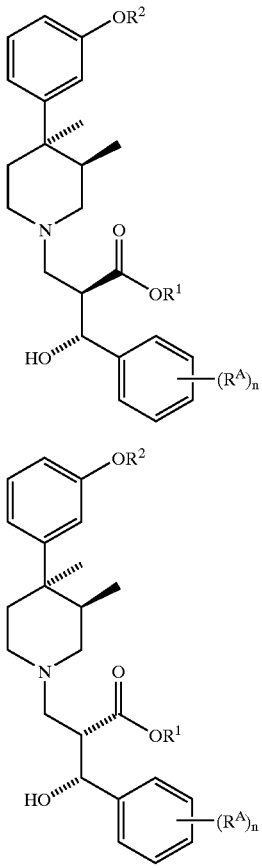

wherein:

each $R^1$ is, independently, H, alkyl, aryl, aralkyl, heteroaryl, or heterocyclyl;

each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

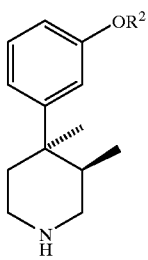

with a compound of Formula IVa:

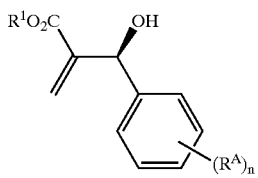

for a time and under conditions effective to provide said compound of Formula IIa, compound of Formula IIb, or mixture thereof. A synthetic procedure that exemplifies the above preparatory process is depicted in FIG. 2.

In the above process, each $R^1$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl, with alkyl being more preferred. Even more preferably, each $R^1$ is, independently, methyl or ethyl.

Also in the above process, each $R^2$ is, independently, H or a hydroxyl protecting group. In preferred embodiments, $R^2$ is H.

In the above process, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is an integer ranging from 0 to 5 (and all combinations and subcombinations of ranges and specific integers therein). Also in preferred embodiments, n is 0.

In accordance with preferred embodiments, contacting the compound of Formula III with a compound of Formula IVa may be carried out in solution comprising a protic or aprotic solvent. The particular type of solvent chosen may affect the diastereoselectivity of the reaction. For example, when the reaction is carried out in a protic solvent, the syn addition product is typically favored, whereas when the reaction is carried out in an aprotic solvent, the anti addition product is typically favored. For example, as depicted in FIG. 2, the addition product of 1a with 2 in the presence of a protic solvent (e.g., MeOH) favors syn product 3a. Conversely, the addition product of 1a with 2 in the presence of an aprotic solvent (e.g., THF) favors anti product 3b.

According to certain preferred embodiments, contacting is carried out in a protic solvent, such as an alcohol. Suitable alcohols may have the formula $R^{10}OH$, where $R^{10}$ is an alkyl group as hereinbefore defined. Exemplary alcohols include methanol, ethanol, isopropanol, n-propanol, butanols, and the like. In preferred embodiments, the protic solvent is methanol. In other preferred embodiments, contacting is carried out in an aprotic solvent such as an ether. Any ether is suitable, including, for example non-cyclic ethers, and cyclic ethers such as THF.

Thus, contacting the compound of Formula III with a compound of Formula IVa in the above process may result in the preparation of a compound of Formula IIa, a compound of Formula IIb, or a mixture of compounds of Formulas IIa and IIb, i.e., a mixture of diastereomers. In some embodiments, the mixture is characterized by a diastereomeric excess of one compound relative to another. For example, mixtures provided in accordance with the present invention may have a diastereomeric excess of the compound of Formula IIa relative to the compound of Formula IIb or, conversely, a diasteromeric excess of the compound of Formula IIb relative to the compound of Formula IIa. In certain preferred, embodiments, the compound of Formula IIa is prepared relative to the compound of Formula IIb in a diastereomeric excess of greater than about 1. More preferably, the compound of Formula IIa is prepared relative to the compound of Formula IIb in a diastereomeric excess ranging from about 2:1 to about 100:1 (and all combinations and subcombinations of ranges and specific ratios therein), with from about 2:1 to about 10:1 being even more preferred. In certain other preferred embodiments, the compound of Formula IIb is prepared relative to the compound of Formula IIa in a diastereomeric excess of greater than about 1. More preferably, the compound of Formula IIb is prepared relative to the compound of Formula IIa in a diasteromeric excess ranging from about 2:1 to about 100:1 (and all combinations and subcombinations of ranges and specific ratios therein), with from about 2:1 to about 10:1 being even more preferred. Methods for determining diasteromeric excess are well known to those skilled in the art and would be readily apparent once placed in possession of the present disclosure.

Contacting the compound of Formula III with a compound of Formula IVa may be conducted under conditions, for example, temperature, and for a time effective to provide compounds of Formulas IIa and/or IIb. By way of general guidance, the reaction may be conducted over a wide range of temperatures. Preferably, the reaction is conducted at a temperature and for a time sufficient to form compounds of Formulas IIa and/or IIb. The particular temperatures and times may vary, depending, for example, on the particular Formula III and Formula IVa compounds involved, as well as the particular solvent employed. In preferred form, the reaction may be conducted at a temperature of from about −78° C. to about 150° C., with from about −20° C. to about 50° C. being more preferred. The reaction may be conducted for a suitable period of time, for example, from about 1 minute to about 7 days, preferably from about 30 minutes to about 48 hours. The reaction may be monitored by any of a number of standard analytical techniques, such as thin layer chromatography (TLC).

In embodiments in which a mixture of compounds of Formula IIa and IIb are prepared, the present processes may further include a step for separating the compounds of Formula IIa and Formula IIb. For example, a diastereomeric mixture of compounds of Formulas IIa and IIb may be separated using any suitable method in the art. In some embodiments, separation may be carried out by chiral column chromatography, HPLC, recrystallization, or classical resolution methods. Other methods for separating the diastereomeric mixtures would be readily apparent to one ordinarily skilled in the art, once placed in possession of the present disclosure.

The compounds of Formulas IIa and/or IIb may undergo further transformations in accordance with the methods of the present invention. For example, the secondary hydroxyl group in the compounds of Formulas IIa and/or IIb may be removed. Thus, the present invention further provides processes for preparing compounds of Formula Va, compounds of Formula Vb, or mixtures thereof:

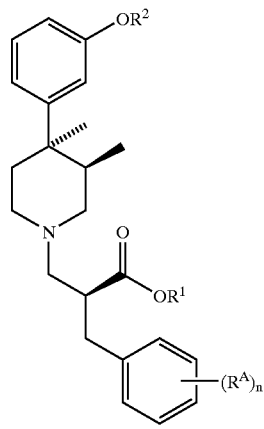

Va

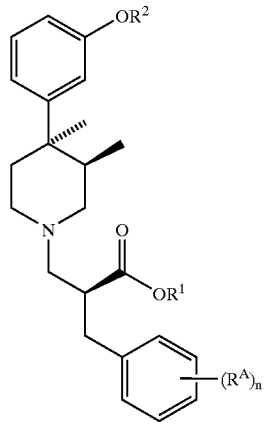

Vb wherein:

each $R^1$ is, independently, H, alkyl, aryl, aralkyl, heteroaryl, or heterocyclyl;

each $R^2$ is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula IIa, a compound of Formula IIb, or a mixture thereof:

IIa

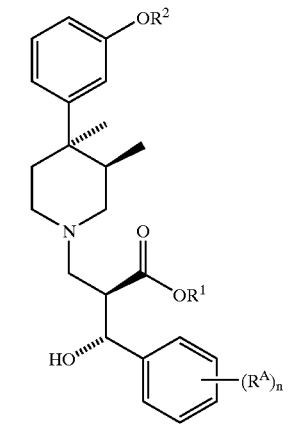

IIb substituting the secondary hydroxyl group of the compound of Formula IIa, the compound of Formula IIb, or the mixture thereof with hydrogen to provide the compound of Formula Va, the compound of Formula Vb, or the mixture thereof. Synthetic procedures that exemplify the above preparatory process are depicted in FIG. 2.

In the above process, each $R^1$ is, independently, H, alkyl, aryl, aralkyl, heteroaryl, or heterocyclyl, and each $R^2$ is, independently, H or a hydroxyl protecting group. Also in the above process, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, as previously defined; and n is an integer ranging from 0 to 5 (and all combinations and subcombinations of ranges and specific integers therein). In preferred embodiments, each R is H. Also in preferred embodiments, n is 0.

In the above process, the compound of Formula IIa and/or IIb may be provided, for example, by a process as described above, including by a process which comprises contacting a compound of Formula III:

III with a compound of Formula IVa:

IVa where each $R^1$, $R^2$, $R^A$ and n are as previously defined, for a time and under conditions effective to provide the compound of Formula IIa, compound of Formula IIb, or mixture thereof.

Substituting of the secondary hydroxyl with hydrogen (i.e., removal of the secondary hydroxyl group) may be carried out by any of a wide variety of suitable techniques. An example of a suitable method for substituting includes hydrogenation. Methods of hydrogenation are well known to those ordinarily skilled in the art, and typically involve contacting the substrate with molecular hydrogen in the presence of a catalyst. Common catalysts include, for example, Pd catalysts such as Pd(OH)$_2$, Pt catalysts such as PtO$_2$, and Ni catalysts such as Raney-type Nickel. Substituting of the secondary hydroxyl group with hydrogen may also involve ionic dehydroxylation. Methods of ionic dehydroxylation are well known in the art of synthetic organic chemistry, and typically involve contacting the substrate with in situ generated or pre-formed silicon hydride species in the presence of a Lewis acid. Ionic hydrogenations are described; for example, in Gevorgyan, et al., *J. Org. Chem.* 2000, 65, 6179–6186 and Sakai, et al., *Tetrahedron Lett.,* 1987, 28, 3817–18, the disclosures of each of which are hereby incorporated herein by reference in their entireties. A further method of substituting the hydroxyl group includes radical deoxygenation. Methods of radical deoxygenation are well known in the art of organic synthetic chemistry, and typically involve contacting the substrate with a tin hydride species in the presence of a radical initiator. Radical deoxygentations are described, for example, in Barton, D. H. R. and Jaszberenyi, J. C., *Tetrahedron Lett.,* 1989, 30, 2619–2622, Barton, et al., *Tetrahedron Lett.,* 1990, 31, 3991–3994, and Boussaguet, et al., *Tetrahedron Lett.,* 2000, 41, 3377–3380, the disclosures of each of which are hereby incorporated herein by reference in their entireties.

The substitution hydrogenation reaction may be conducted under conditions, for example, temperature, and for a time effective to provide compounds of Formulas Va and/or Vb. The particular temperatures and times may vary, depending, for example, on the particular Formula IIa and/or IIb compounds involved, the particular hydrogenating agent, as well as the particular solvent employed. In preferred form, the reaction may be conducted at a temperature of from about −78° C. to about 150° C., with from about 0° C.

to about 50° C. being more preferred. The reaction may be conducted for a suitable period of time, for example, from about 1 minute to about 7 days, preferably from about 30 minutes to about 48 hours. The reaction may be monitored by standard analytical techniques, such as thin layer chromatography (TLC).

Substituting can also include activating the secondary hydroxyl group prior to removal by converting the secondary hydroxyl group to a group having the formula —OR$^3$ wherein each R$^3$ is, independently, a hydroxyl activating group and substituting the —OR$^3$ group with hydrogen. A wide variety of hydroxyl activating groups are available and would be suitable for use in the present processes. In preferred embodiments, the hydroxyl activating group is, independently, alkylcarbonyl, arylcarbonyl, aralkylcarbonyl, heteroarylcarbonyl, heterocyclylcarbonyl, C(S)O-aryl, C(S)O-alkyl, or R$^Z_3$Si—, wherein each R$^Z$ is, independently, alkyl or aryl, with alkylcarbonyl being more preferred. A particularly preferred hydroxyl activating agent is (—C(O)CH$_3$). Substituting of the —OR$^3$ group with hydrogen can be accomplished by any of the aforementioned methods, such as hydrogenation, ionic dehydroxylation, or radical deoxygenation.

In an alternate embodiment, substituting of the secondary hydroxyl group with hydrogen may also involve contacting a compound of Formula IIa, Formula IIb, or mixture thereof with an activating reagent for a time and under conditions effective to provide a compound of Formula VIa, a compound of Formula VIb, or a mixture thereof:

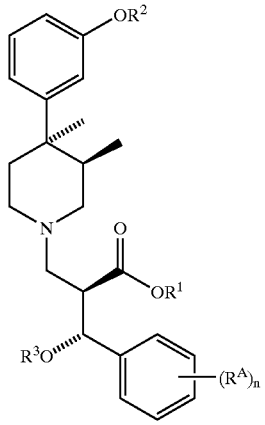

VIa

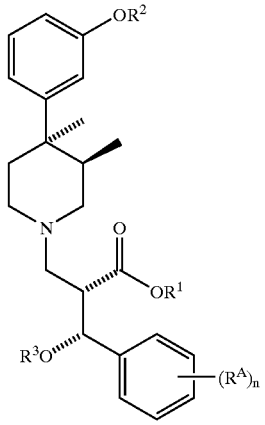

VIb wherein each R$^1$, R$^2$, R$^A$ and n is as defined previously, and each R$^3$ is, independently, a hydroxyl activating group; and contacting the compound of Formula VIa, Formula VIb, or mixture thereof with a hydrogenating reagent for a time and under conditions effective to provide the compound of Formula Va, Formula Vb, or mixture thereof.

Suitable activating reagents include reagents that are capable of replacing the hydrogen of the secondary hydroxyl group with a hydroxyl activating group in any of the compounds of Formulas IIa and IIb. Examples of suitable activating reagents include alkyl anhydrides such as, for example, acetic anhydride (Ac$_2$O), propionic anhydride, and trifluoroacetic anhydride, alkyl vinyl ethers such as dihydopyran, trialkylsilyl halides such as chlorotrimethylsilane, and alkyl alcohols such as methanol and ethanol, and the like.

Suitable hydrogenating reagents include reagents capable of replacing an activated or unactivated hydroxyl group with hydrogen. Hydrogenating reagents can include those compounds that effect hydrogenation, ionic dehydroxylation, radical deoxygenation, or other similar processes. For example, hydrogenating reagents can include molecular hydrogen and a Pd catalyst such as Pd(OH)$_2$, a Pt catalyst such as PtO$_2$, or a Ni catalyst such as Raney-type Nickel. Other hydrogenating reagents can include, in ionic hydrogenations, for example, silicon hydride species, such as, for example, dimethylethylsilane, in the presence of a Lewis acid, such as, for example, B(C$_6$F$_5$)$_3$, and in radical deoxygenations, for example, tin hydride species, such as, for example, tributyl tin hydride, in the presence of a radical initiator, such as AIBN (free radical initiator).

The activation reaction may be conducted under conditions, for example, temperature, and for a time effective to provide compounds of Formulas VIa and/or VIb. The particular temperatures and times may vary, depending, for example, on the particular Formula IIa and/or IIb compounds involved, the particular activating agent, as well as the particular solvent employed. In preferred form, the reaction may be conducted at a temperature of from about –78° C. to about 150° C., with from about 25° C. to about 70° C. being more preferred. The reaction may be conducted for a suitable period of time, for example, from about 5 minutes to about 7 days, preferably from about 30 minutes to about 48 hours. The reaction may be monitored by standard analytical techniques, such as thin layer chromatography (TLC).

In embodiments of the above process, each R$^2$ is, independently, a hydroxyl protecting group that may be removed from the compounds of Formula VIa and/or VIb. A wide variety of techniques and reagents are available for the removal of the hydroxyl protecting group, and would be apparent to the ordinarily skilled artisan once placed in possession of the present invention. For example, removal of the hydroxyl protecting group can be carried out, for example, by base hydrolysis, acid hydrolysis, or hydrogenation.

Examples of the above process involving methods for removal of the secondary hydroxyl from compounds of Formulas IIa and IIb are provided in FIG. 2. In this regard, compounds 3a and 3b are reacted with activating reagent Ac$_2$O in the presence of triethylamine, DMAP, and dichloromethane to provide intermediates 4a and 4b having an acetylated secondary hydroxyl group. Subsequently, the acetylated intermediate is hydrogenated with molecular hydrogen in the presence of Pd(OH)$_2$, effectively removing the secondary hydroxyl group to give the intermediates 5a and 5b. Additionally, intermediates 5a and 5b can be hydrolyzed, such as with NaOH, to convert the methyl ester moiety to a carboxyl group, as exemplified by compound V-a-i. Further, intermediates 5a and 5b can be hydrolyzed with K$_2$CO$_3$ and MeOH to yield intermediates 6a and 6b.

The compounds of Formulas Va and/or Vb may undergo further transformations in accordance with the methods of the present invention. In this regard, the present invention provides processes for preparing compounds of Formula Ia, Formula Ib, or mixtures thereof:

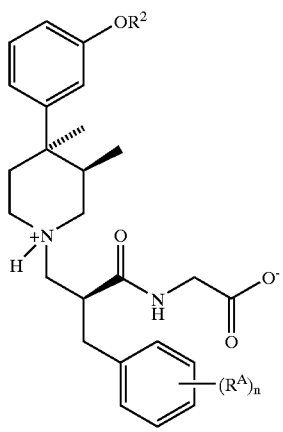

Ia

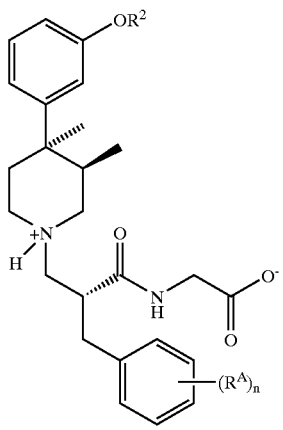

Ib wherein:
each $R^2$ is, independently, H or a hydroxyl protecting group;
each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
n is 0 to 5;
or a salt thereof.

The process comprises providing a compound of Formula Va, a compound of Formula Vb, or a mixture thereof (which may be prepared, for example, employing a method described herein), and selectively converting the —OR$^1$ moiety of the compound of Formula Va, the compound of Formula Vb, or the mixture thereof to —NHCH$_2$COOH. In accordance with certain embodiments, this selective conversion may proceed directly from compounds of Formula Va and/or Vb. In accordance with other preferred embodiments, the conversion may first involve optionally converting —OR$^1$ of the compounds of Formula Va and/or Vb to —X, where X is halo or —OC(O)R$^1$. Techniques for the optional conversion of the compounds of Formula Va and/or Vb to acid halides or acid anhydrides are well known in the art, and are described, for example, in Larock, R. C., *Comprehensive Organic Transformations*, VCH Publishers, Inc., NY (1989), and Carey, F. A., and Sundberg, R. J., *Advanced Organic Chemistry*, 3$^{rd}$ Edition, Plenum Press, NY (1990), the disclosures of each of which are hereby incorporated herein by reference in their entireties.

In the preparation of the compounds of Formulas Ia and/or Ib from the compounds of Formulas Va and/or Vb, each $R^1$ in compounds Va and/or Vb is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl, with alkyl being more preferred. In even more preferred embodiments, each $R^1$ is, independently, methyl or ethyl. In certain other preferred embodiments each $R^1$ is H. Also in the preparation of the compounds of Formulas Ia and/or Ib from the compounds of Formulas Va and/or Vb, each $R^2$ is, independently, hydrogen or a hydroxyl protecting group, with hydrogen being preferred. Further in the preparation of the compounds of Formulas Ia and/or Ib, n is an integer from 0 to 5 (and all combinations and subcombinations of ranges and specific integers therein). In even more preferred embodiments, the above transformation reaction provides Alvimopan and/or diastereomers thereof.

A wide variety of techniques are available for selectively converting —OR$^1$ to —NHCH$_2$COOH in the above process, and would be readily apparent to one of ordinary skill in the art, once armed with the teachings of the present disclosure. Suitable conversion techniques are described, for example, in Werner et al., *J. Org. Chem.*, 1996, 61, 587, the disclosure of which is hereby incorporated herein by reference in its entirety. An example of a suitable selective conversion includes contacting NH$_2$CH$_2$COOH, or an acid addition salt, ester or other derivative thereof with a compound of Formula Va, Formula Vb, or a mixture thereof.

Contacting a compound of Formula Va and/or Vb with a compound NH$_2$CH$_2$COOH may be carried out in a protic solvent, such as an alcohol, or in an aprotic solvent such as an ether. Suitable alcohols and ethers include those discussed above. In addition, the conversion may be conducted under conditions, for example, temperature, and for a time effective to provide compounds of Formulas Ia and/or Ib. The particular temperatures and times may vary, depending, for example, on the particular Formula Va and/or Vb compounds involved, as well as the particular solvent employed. In preferred form, the reaction may be conducted at a temperature of from about −20° C. to about 100° C., with from about 0° C. to about 25° C. being more preferred. The reaction may be conducted for a suitable period of time, for example, from about 5 minutes to about 48 hours, preferably from about 1 hour to about 24 hours. The reaction may be monitored by standard analytical techniques, such as thin layer chromatography (TLC).

Figure 3:
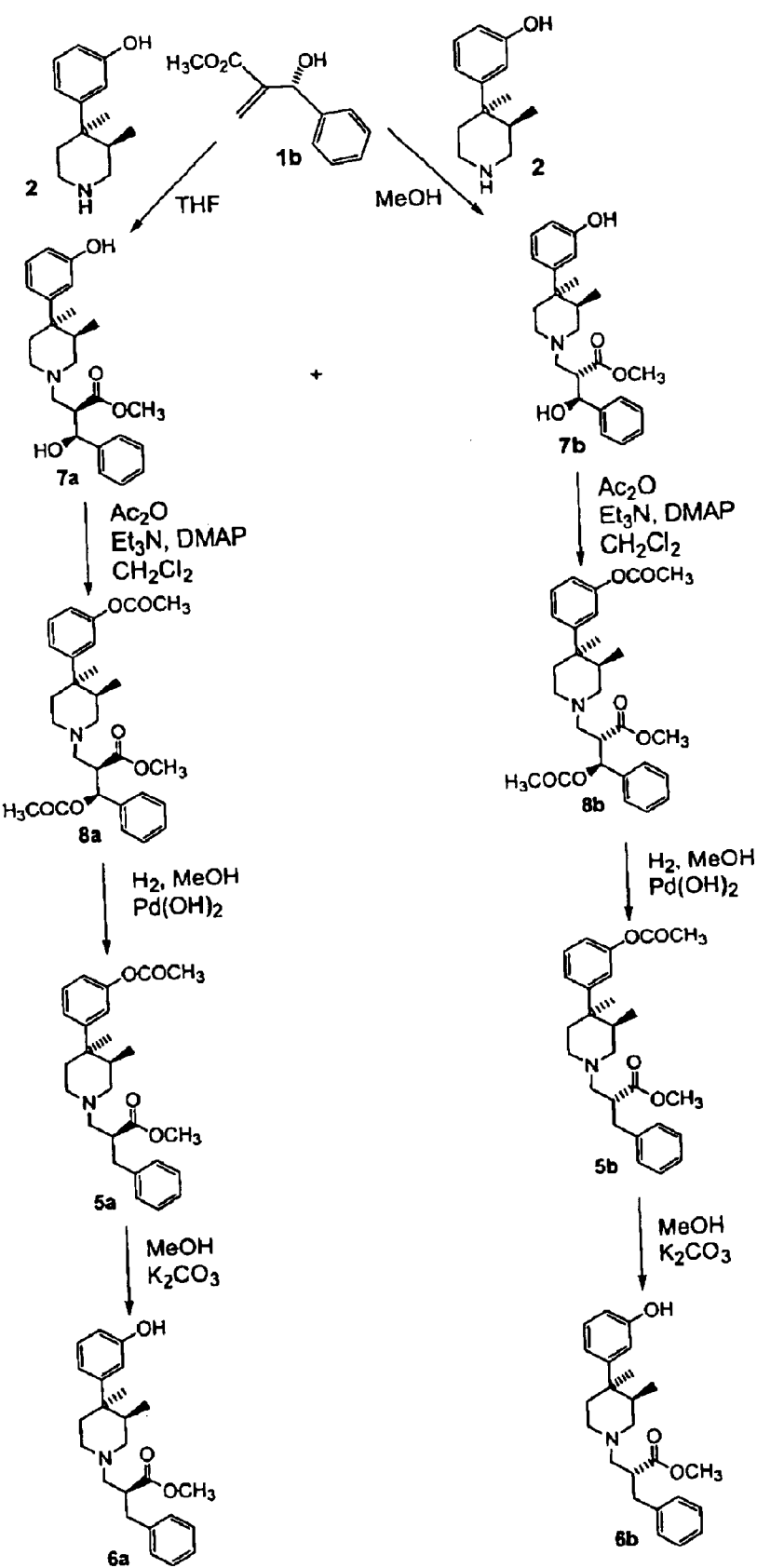

In another embodiment of the present invention, there are provided processes for preparing a compound of Formula IIc, a compound of Formula IId, or a mixture thereof:

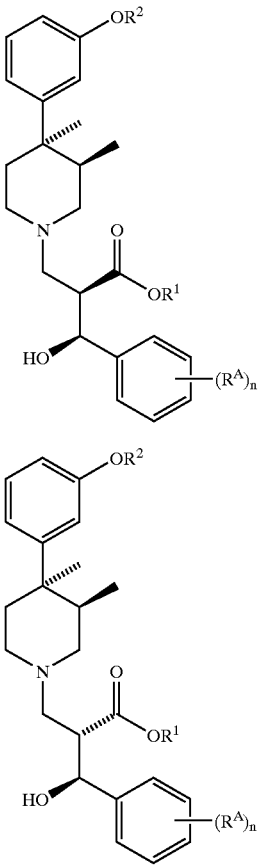

wherein:

each R¹ is, independently, H, alkyl, aryl, aralkyl, heteroaryl, or heterocyclyl;

each R² is, independently, H or a hydroxyl protecting group;

each $R^A$ is, independently, halo, alkyl, halo-substituted alkyl alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

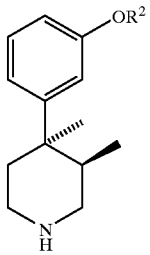

with a compound of Formula IVb:

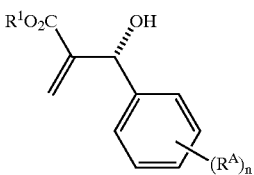

for a time and under conditions effective to provide the compound of Formula IIc, the compound of Formula IId, or the mixture thereof. A synthetic procedure that exemplifies the above preparatory process is depicted in FIG. 3.

In the above process, each R¹ is, independently, H, alkyl, aryl, aralkyl, heteroaryl, or heterocyclyl. In certain preferred embodiments, each R¹ is, independently, alkyl, aryl, aralkyl, heteroaryl, or heterocyclyl, with alkyl being more preferred. In even more preferred embodiments, each R¹ is, independently, methyl or ethyl.

Also in the above process, each R² is, independently, H or a hydroxyl protecting group. In certain preferred embodiments, each R² is H.

In the above process, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and n is an integer ranging from 0 to 5 (and all combinations and subcombinations of ranges and specific integers therein). In preferred embodiments, each R is H. Also in preferred embodiments, n is 0.

The preparation of compounds of Formulas IIc and/or IId may involve contacting a compound of Formula III with a compound of Formula IVb in a solvent, including protic or aprotic solvents. As with processes for the preparation of compounds of Formulas IIa and/or IIb, the particular solvent selected may affect the diastereoselectivity of the reaction. For example, when the reaction is carried out in a protic solvent, the syn addition product is typically favored, whereas when the reaction is carried out in an aprotic solvent, the anti addition product is typically favored. For example, as depicted in FIG. 3, the addition product of 1b with 2 in the presence of a protic solvent (e.g., MeOH) favors syn product 7b. Conversely, the addition product of 1b with 2 in the presence of an aprotic solvent (e.g., THF) favors anti product 7a.

According to certain preferred embodiments, contacting the compound of Formula III with a compound of Formula IVb is carried out in a protic solvent, such as an alcohol. Suitable alcohols may have the formula R¹⁰OH, where R¹⁰ is an alkyl group as hereinbefore defined. Exemplary alcohols include methanol, ethanol, isopropanol, n-propanol, butanols, and the like. In preferred embodiments, the protic solvent is methanol. In other preferred embodiments, contacting is carried out in an aprotic solvent such as an ether. Any ether is suitable, including, for example non-cyclic ethers, and cyclic ethers such as THF.

Thus, contacting the compound of Formula III with a compound of Formula IVb in the above process may result in the preparation of a compound of Formula IIc, a compound of Formula IId, or a mixture of compounds of Formulas IIc and IId, i.e., a mixture of diastereomers. In some embodiments, the mixture is characterized by a diastereomeric excess of one compound relative to another. For example, mixtures provided in accordance with the present invention may have a diastereomeric excess of the compound of Formula IIc relative to the compound of Formula IId or, conversely, a diastereomeric excess of the compound of Formula IId relative to the compound of Formula IIc. In certain preferred embodiments, the compound of Formula IIc is prepared relative to the compound of Formula IId in a diastereomeric excess of greater than about 1. More preferably, the compound of Formula IIc is prepared relative to the compound of Formula IId in a diastereomeric excess ranging from about 2:1 to about 100:1 (and all combinations and subcombinations of ranges and specific ratios therein), with from about 2:1 to about 10:1 being even more preferred. In certain other preferred embodiments, the compound of Formula IId is prepared relative to the compound of Formula IIc in a diastereomeric excess of greater than about 1. More preferably, the compound of Formula IId is prepared relative to the compound of Formula IIc in a diasteromeric excess ranging from about 2:1 to about 100:1 (and all combinations and subcombinations of ranges and specific ratios therein), with from about 2:1 to about 10:1 being even more preferred.

Contacting the compound of Formula III with a compound of Formula IVb may be conducted under conditions, for example, temperature, and for a time effective to provide compounds of Formulas IIc and/or IId. The particular temperatures and times may vary, depending, for example, on the particular Formula III and/or IVb compounds involved, as well as the particular solvent employed. In preferred form, the reaction may be conducted at a temperature of from about −78° C. to about 150° C., with from about −20° C. to about 50° C. being more preferred. The reaction may be conducted for a suitable period of time, for example, from about 1 minute to about 7 days, preferably from about 30 minutes to about 48 hours. The reaction may be monitored by standard analytical techniques, such as thin layer chromatography (TLC).

In embodiments in which a mixture of compounds of Formula IIc and IId are prepared, the present processes may further include a step for separating the compounds of Formula IIc and Formula IId. A wide variety of methods are available for separating mixtures of compounds of Formulas IIc and IId, and suitable methods include those discussed above in connection with the separation of compounds of Formulas IIa and IIb.

As with the compounds of Formulas IIa and IIb, the compounds of Formulas IIc and/or IId may undergo further transformations in accordance with the methods of the present invention. For example, the secondary hydroxyl group in the compounds of Formulas IIc and/or IId may be removed. Thus, compounds of Formula Va, compounds of Formula Vb, or mixtures thereof may be prepared from compounds of Formulas IIc, compounds of Formula IId, and mixtures thereof:

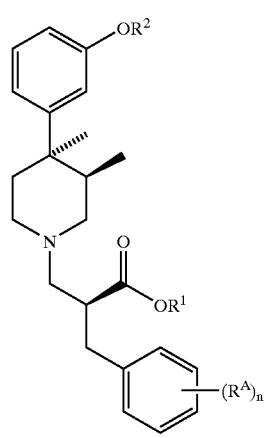

Va

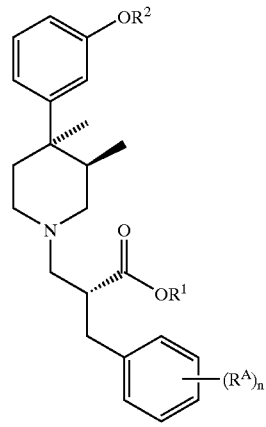

Vb wherein:

each R¹ is, independently, H, alkyl, aryl, aralkyl, heteroaryl, or heterocyclyl;

each R² is, independently, H or a hydroxyl protecting group;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula IIc, a compound of Formula IId, or a mixture thereof:

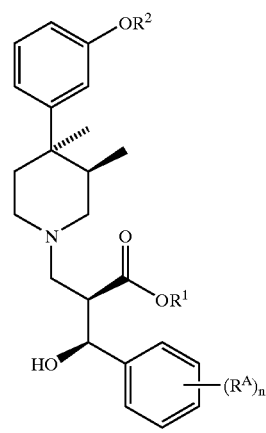

IIc

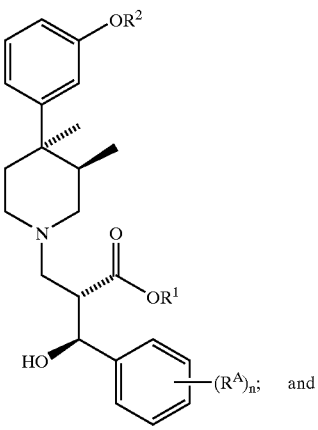

substituting the secondary hydroxyl group with hydrogen to provide the compound of Formula Va, the compound of Formula Vb, or the mixture thereof. Synthetic procedures that exemplify the above preparatory process are depicted in FIG. 3.

In the above process, each $R^1$ is, independently, H, alkyl, aryl, aralkyl, heteroaryl, or heterocyclyl, and each $R^2$ is, independently, H or a hydroxyl protecting group. Also in the above process, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, $NHSO_2R$, $SO_2NRR$, aminocarbonyl, amino, nitro, cyano, or SR, wherein each R is, independently, as previously defined; and n is an integer ranging from 0 to 5 (and all combinations and subcombinations of ranges and specific integers therein). In preferred embodiments, each R is H. Also in preferred embodiments, n is 0.

In the above process, the compound of Formula IIc and/or IId may be provided, for example, by a process as described above, including by a process which comprises contacting a compound of Formula III:

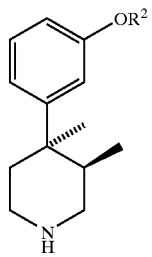

with a compound of Formula IVb:

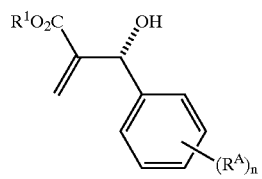

where each $R^1$, $R^2$, $R^A$ and n is as previously defined, for a time and under conditions effective to provide said compound of Formula IIc, compound of Formula IId, or mixture thereof.

Substitution or removal of the secondary hydroxyl with hydrogen may be carried out by any of a wide variety of suitable techniques, including the techniques discussed above in connection with the preparation of the compounds of Formulas Va and/or Vb from the compounds of Formulas IIa and/or IIb. Thus, exemplary substitution methods include, for example, hydrogenation, ionic dehydroxylation and radical deoxygenation, using methods and reagents as discussed above.

The substitution hydrogenation reaction may be conducted under conditions of temperature and time effective to provide compounds of Formulas Va and/or Vb. The particular temperatures and times may vary, depending, for example, on the particular Formula IIc and/or IId compounds involved, the particular hydrogenating agent, as well as the particular solvent employed. In preferred form, the reaction may be conducted at a temperature of from about –78° C. to about 150° C., with from about –20° C. to about 50° C. being more preferred. The reaction may be conducted for a suitable period of time, for example, from about 1 minute to about 7 days, preferably from about 5 minutes to about 48 hours. The reaction may be monitored by any of a number of standard analytical techniques, such as thin layer chromatography (TLC).

As described above, substituting can also include activating the secondary hydroxyl group prior to removal by converting the secondary hydroxyl group to a group having the formula —$OR^3$ wherein each $R^3$ is as previously defined, and substituting the —$OR^3$ group with hydrogen. Substituting the —$OR^3$ group with hydrogen can be accomplished by any of the aforementioned methods such as, for example, hydrogenation, ionic dehydroxylation, or radical deoxygenation.

In an alternate embodiment, substituting of the secondary hydroxyl group with hydrogen may also involve contacting a compound of Formula IIc, a compound of Formula IId, or a mixture thereof with an activating reagent for a time and under conditions effective to provide a compound of Formula VIe, a compound of Formula VIc, or a mixture thereof:

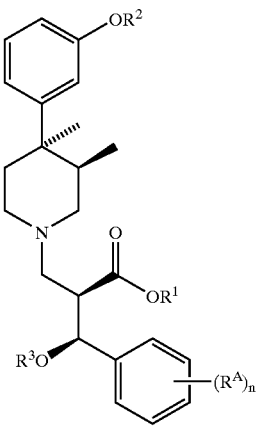

-continued

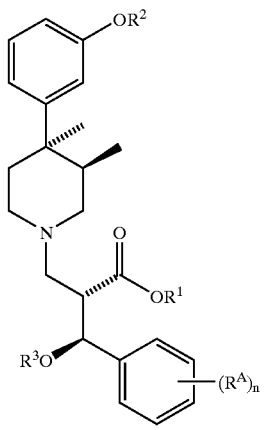

VId wherein each $R^1$, $R^2$, $R^A$ and n is as previously defined, and each $R^3$ is, independently, a hydroxyl activating group; and contacting the compound of Formula VIc, the compound of Formula VId, or the mixture thereof with a hydrogenating reagent for a time and under conditions effective to provide the compound of Formula Va, the compound of Formula Vb, or the mixture thereof.

As with the compounds of Formulas IIa and IIb, discussed above, suitable activating reagents include reagents that are capable of replacing the hydrogen of the secondary hydroxyl group with a hydroxyl activating group in the compounds of Formulas IIc and IId. Examples of suitable activating reagents include alkyl anhydrides, such as, for example, acetic anhydride ($Ac_2O$), propionic anhydride, and trifluoroacetic anhydride, alkyl vinyl ethers, such as dihydopyran, trialkylsilyl halides, such as chlorotrimethylsilane, and alkyl alcohols, such as methanol and ethanol, and the like.

As with the embodiments discussed above, suitable hydrogenating reagents include compounds that effect hydrogenation, ionic dehydroxylation, radical deoxygenation, or other similar processes. An example of a suitable hydrogenating reagent includes molecular hydrogen and a Pd catalyst such as $Pd(OH)_2$, a Pt catalyst such as $PtO_2$, or a Ni catalyst such as Raney-type Nickel. Other hydrogenating reagents can include, in ionic hydrogenations, for example, silicon hydride species, such as, for example, dimethylethylsilane, in the presence of a Lewis acid, such as, for example, $B(C_6F_5)_3$, and in radical deoxygenations, for example, tin hydride species, such as, for example, tributyl tin hydride, in the presence of a radical initiator, such as AIBN (free radical initiator).

In embodiments of the above process, each $R^2$ is, independently, a hydroxyl protecting group that may be removed from the compounds of Formula VIc and/or VId. Removal of the hydroxyl protecting group may be carried out by any of a wide variety of suitable techniques, including the techniques discussed above in connection with the preparation of the compounds of Formulas Va and/or Vb from the compounds of Formulas IIa and/or IIb. Thus, exemplary removal techniques include, for example, base hydrolysis, acid hydrolysis, or hydrogenation.

The activation reaction may be conducted under conditions, for example, temperature, and for a time effective to provide compounds of Formulas VIc and/or VId. The particular temperatures and times may vary, depending, for example, on the particular Formula IIc and/or IId compounds involved, the particular activating agent, as well as the particular solvent employed. In preferred form, the reaction may be conducted at a temperature of from about −20° C. to about 50° C., with from about 0° C. to about 25° C. being more preferred. The reaction may be conducted for a suitable period of time, for example, from about 1 minute to about 48 hours, preferably from about 30 minutes to about 24 hours. The reaction may be monitored by standard analytical techniques, such as thin layer chromatography (TLC).

Examples of the above process involving methods for removal of the secondary hydroxyl from compounds of Formulas IIc and IId are provided in FIG. 3. In this regard, compounds 7a and 7b are reacted with activating reagent $Ac_2O$ in the presence of triethylamine, DMAP, and dichloromethane to provide intermediates 8a and 8b having an acetylated secondary hydroxyl group. Subsequently, the acetylated intermediate is hydrogenated with molecular hydrogen in the presence of $Pd(OH)_2$, effectively removing the secondary hydroxyl group to give the intermediates 5a and 5b. Intermediates 5a and 5b can be hydrolyzed with $K_2CO_3$ and MeOH to yield intermediates 6a and 6b.

The compounds of Formulas Va and/or Vb may undergo further transformations in accordance with the methods of the present invention, and may be utilized in processes for preparing compounds of Formula Ia, Formula Ib, or mixtures thereof, as discussed in detail above.

In accordance with another embodiment of the present invention, there are provided processes for preparing compounds of Formula VIIa, Formula VIIb, or mixtures thereof:

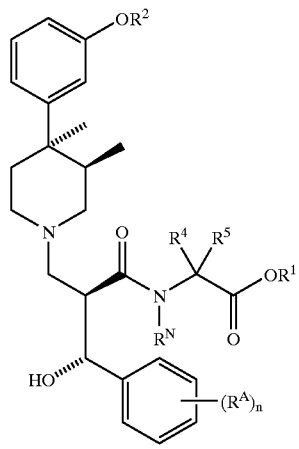

VIIa

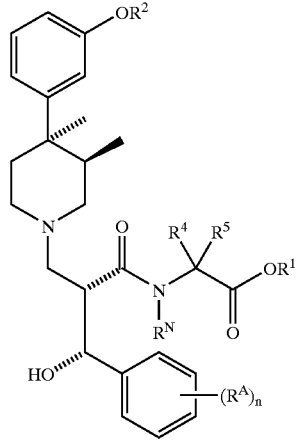

VIIb wherein:
each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

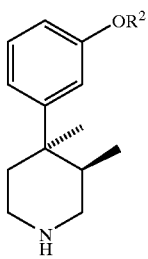

III with a compound of Formula VIIIa:

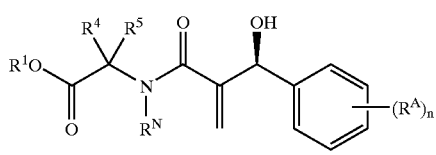

Figure 4:
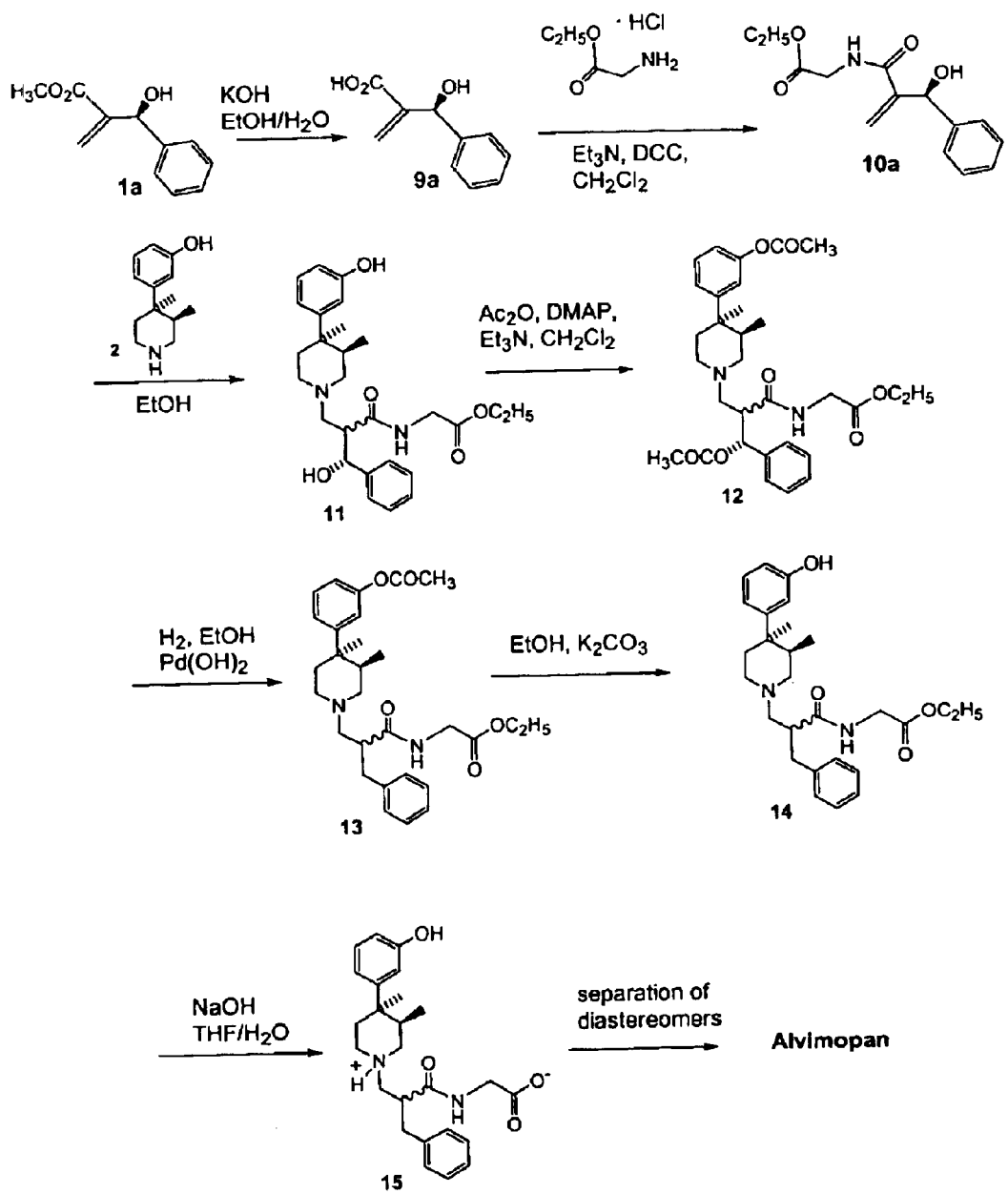

VIIIa for a time and under conditions effective to provide said compound of Formula VIIa, said compound of Formula VIIb, or said mixture thereof. A synthetic procedure that exemplifies the above preparatory process is depicted in FIG. 4.

In the above process, each $R^1$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl, with alkyl being more preferred. In even more preferred embodiments, each $R^1$ is, independently, methyl or ethyl.

Also in the above process, each $R^2$ is, independently, H or a hydroxyl protecting group. In certain preferred embodiments, each $R^2$ is a hydroxyl protecting group.

In the above process, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, CC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

In accordance with preferred embodiments, contacting the compound of Formula III with a compound of Formula VIIIa may be carried out in solution comprising a protic or aprotic solvent. In preferred form, contacting the compound of Formula III with a compound of Formula VIIIa may be carried out in a protic solvent.

According to certain preferred embodiments, contacting is carried out in a protic solvent, such as an alcohol. Suitable alcohols may have the formula $R^{10}$OH, where $R^{10}$ is an alkyl group as hereinbefore defined. Exemplary alcohols include methanol, ethanol, isopropanol, n-propanol, butanols, and the like. In preferred embodiments, the protic solvent is methanol. In other preferred embodiments, contacting is carried out in an aprotic solvent such as an ether. Any ether is suitable, including, for example non-cyclic ethers, and cyclic ethers such as THF.

Thus, contacting the compound of Formula III with a compound of Formula VIIIa in the above process may result in the preparation of a compound of Formula VIIa, a compound of Formula VIIb, or a mixture of compounds of Formulas VIIa and VIIb, i.e., a mixture of diastereomers.

Contacting the compound of Formula III with a compound of Formula VIIIa may be conducted under conditions of temperature and time effective to provide compounds of Formulas VIIa and/or VIIb. The particular temperatures and times may vary, depending, for example, on the particular Formula III and Formula VIIIa compounds involved, as well as the particular solvent employed. In preferred form, the reaction may be conducted at a temperature of from about 0° C. to about 200° C., with from about 25° C. to about 80° C. being more preferred. The reaction may be conducted for a suitable period of time, for example, from about 1 hour to about 72 hours, preferably from about 12 hours to about 48 hours. The reaction may be monitored by standard analytical techniques, such as thin layer chromatography (TLC).

In embodiments in which a mixture of compounds of Formula VIIa and VIIb are prepared, the present processes may further include a step for separating the compounds of Formula VIa and Formula VIIb. For example, a diastereomeric mixture of compounds of Formulas VIIa and VIIb may be separated using any suitable method in the art. In some embodiments, separation may be carried out by chiral column chromatography, HPLC, recrystallization, or classical resolution methods. Other methods for separating the diastereomeric mixtures would be readily apparent to one skilled in the art, once placed in possession of the present disclosure.

In the above process, the compound of Formula VIIIa may be provided, for example, by a process which comprises contacting a compound having the formula:

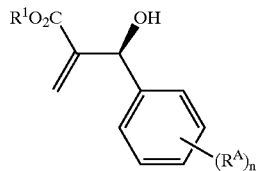

wherein each $R^1$ is, independently, H, alkyl, aryl, aralkyl, heteroaryl, or heterocyclyl with a compound, or acid addition salt thereof, having the formula:

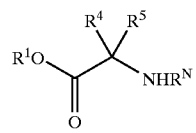

where each $R^1$, $R^4$, $R^5$, $R^N$, $R^A$ and n is as previously defined, for a time and under conditions effective to provide the compound of Formula VIIa.

Contacting the above compounds to provide a compound of Formula VIIIa may be carried out in a protic solvent, such as an alcohol, or in an aprotic solvent such as an ether.

Suitable alcohols and ethers include those discussed above. The contacting may be conducted under conditions of temperature and time effective to provide a compounds of Formula VIIIa. The particular temperatures and times may vary, depending, for example, on the particular starting materials involved, as well as the particular solvent employed. In preferred form, the reaction may be conducted at a temperature of from about −20° C. to about 100° C., with from about 0° C. to about 25° C. being more preferred. The reaction may be conducted for a suitable period of time, for example, from about 5 minutes to about 48 hours, preferably from about 1 hour to about 24 hours. The reaction may be monitored by standard analytical techniques, such as thin layer chromatography (TLC).

The compounds of Formulas VIIa and/or VIIb may undergo further transformations in accordance with the methods of the present invention. For example, the secondary hydroxyl group in the compounds of Formulas VIa and/or VIb may be removed. Thus, the present invention further provides processes for preparing compounds of Formula IXa, compounds of Formula IXb, or mixtures thereof:

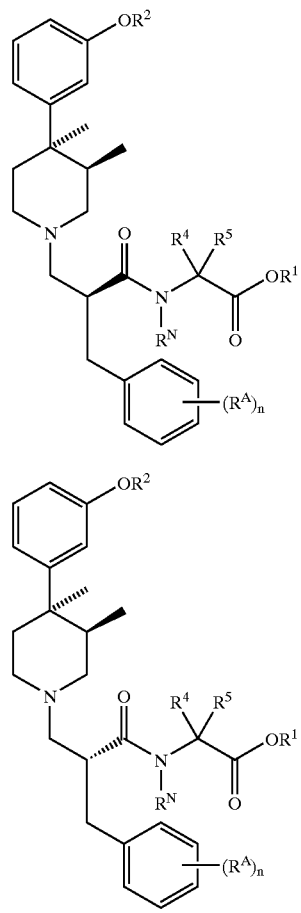

wherein:
  each $R^1$ is, independently, H, alkyl, aryl, aralkyl, heteroaryl, or heterocyclyl;
  each $R^2$ is, independently, H or a hydroxyl protecting group;
  each $R^4$, $R^5$, and $R^N$ is, independently, H, alkyl, or aralkyl;
  each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
  n is 0 to 5;
  or a salt thereof;
comprising providing a compound of Formula VIIa, a compound of Formula VIIb, or a mixture thereof:

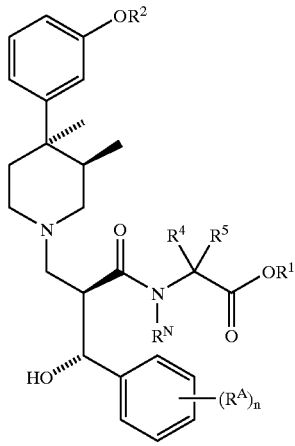

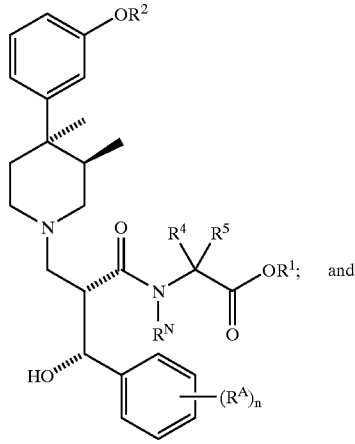

substituting the secondary hydroxyl group of said compound of Formula VIIa, said compound of Formula VIIb, or said mixture thereof with hydrogen to provide said compound of Formula IXa, said compound of Formula IXb, or said mixture thereof. Synthetic procedures that exemplify the above preparatory process are depicted in FIG. 4.

In the above process, each $R^1$ is, independently, H, alkyl, aryl, aralkyl, heteroaryl, or heterocyclyl, each $R^2$ is, independently, hydrogen or a hydroxyl protecting group. In certain preferred embodiments, each $R^1$ is, independently, alkyl, aryl, aralkyl, heteroaryl, or heterocyclyl, with alkyl being more preferred. In even more preferred embodiments, each $R^1$ is, independently, methyl or ethyl. Also in the above process, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

In the above process, the compound of Formula VIIa and/or VIIb may be provided, for example, by a process as described above, including by a process which comprises contacting a compound of Formula III:

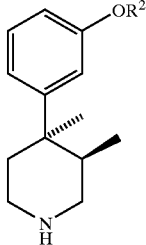

III with a compound of Formula VIIIa:

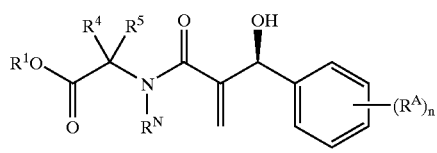

VIIIa where each $R^1$, $R^2$, $R^4$, $R^5$, $R^A$, $R^N$ and n is as previously defined, for a time and under conditions effective to provide the compound of Formula VIa, the compound of Formula VIIb, or the mixture thereof.

Substitution or removal of the secondary hydroxyl with hydrogen may be carried out by any of a wide variety of suitable techniques, including the techniques discussed above in connection with the preparation of the compounds of Formulas Va and/or Vb. Thus, exemplary substitution methods include, for example, hydrogenation, ionic dehydroxylation and radical deoxygenation, using methods and reagents as discussed above.

The substitution hydrogenation reaction may be conducted under conditions of temperature and time effective to provide compounds of Formulas IXa and/or IXb. The particular temperatures and times may vary, depending, for example, on the particular Formula VIIa and/or VIIb compounds involved, the particular hydrogenating agent, as well as the particular solvent employed. In preferred form, the reaction may be conducted at a temperature of from about −78° C. to about 150° C., with from about 0° C. to about 50° C. being more preferred. The reaction may be conducted for a suitable period of time, for example, from about 1 minute to about 7 days, preferably from about 30 minutes to about 48 hours. The reaction may be monitored by standard analytical techniques, such as thin layer chromatography (TLC).

As described above, substituting can also include activating the secondary hydroxyl group prior to removal by converting the secondary hydroxyl group to a group having the formula —$OR^3$ wherein each $R^3$ is as previously defined, and substituting the —$OR^3$ group with hydrogen. Substituting the —$OR^3$ group with hydrogen can be accomplished by any of the aforementioned methods such as, for example, hydrogenation, ionic dehydroxylation, or radical deoxygenation.

In an alternate embodiment, substituting of the secondary hydroxyl group with hydrogen may also involve contacting a compound of Formula VIa, a compound of Formula VIb, or a mixture thereof with an activating reagent for a time and under conditions effective to provide a compound of Formula Xa, a compound of Formula Xb, or a mixture thereof:

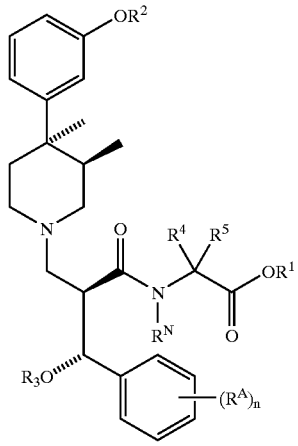

Xa

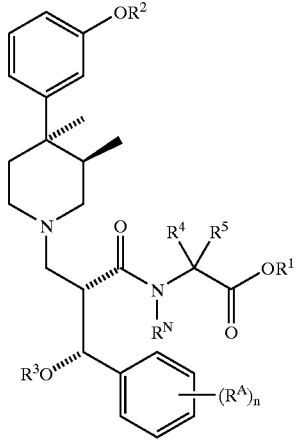

Xb wherein each $R^1$, $R^2$, $R^4$, $R^5$, $R^A$, $R^N$ and n is as previously defined, and each $R^3$ is, independently, a hydroxyl activating group; and contacting the compound of Formula Xa, the compound of Formula Xb, or the mixture thereof with a hydrogenating reagent for a time and under conditions effective to provide the compound of Formula IXa, the compound of Formula IXb, or the mixture thereof.

As with the compounds of Formulas IIa, IIb, IIc and IId discussed above, suitable activating reagents include reagents that are capable of replacing the hydrogen of the secondary hydroxyl group with a hydroxyl activating group in the compounds of Formulas VIIa and VIIb. Examples of suitable activating reagents include alkyl anhydrides, such as, for example, acetic anhydride ($Ac_2O$), propionic anhydride, and trifluoroacetic anhydride, alkyl vinyl ethers such as dihydopyran, trialkylsilyl halides such as chlorotrimethylsilane, and alkyl alcohols such as methanol and ethanol, and the like.

As with the embodiments discussed above, suitable hydrogenating reagents include compounds that effect hydrogenation, ionic dehydroxylation, radical deoxygenation, or other similar processes. An example of a suitable hydrogenating reagent includes molecular hydrogen and a Pd catalyst such as $Pd(OH)_2$, a Pt catalyst such as $PtO_2$, or a Ni catalyst such as Raney-type Nickel. Other hydrogenating reagents can include, in ionic hydrogenations, for example, silicon hydride species, such as, for example, dimethylethylsilane, in the presence of a Lewis acid, such as, for example, B(C₆F₅)₃, and in radical deoxygenations, for example, tin hydride species, such as, for example, tributyl tin hydride, in the presence of a radical initiator, such as AIBN (well known free radical initiator).

The activation reaction may be conducted under conditions of temperature time effective to provide compounds of Formulas Xa and/or Xb. The particular temperatures and times may vary, depending, for example, on the particular Formula VIIa and/or VIIb compounds involved, the particular activating agent, as well as the particular solvent employed. In preferred form, the reaction may be conducted at a temperature of from about −78° C. to about 150° C., with from about 25° C. to about 70° C. being more preferred. The reaction may be conducted for a suitable period of time, for example, from about 5 minutes to about 7 days, preferably from about 30 minutes to about 48 hours. The reaction may be monitored by standard analytical techniques, such as thin layer chromatography (TLC).

In embodiments of the above process, each $R^2$ is, independently, a hydroxyl protecting group that may be removed from the compounds of Formula IXa, IXb, Xa and/or Xb. Removal of the hydroxyl protecting group may be carried out by any of a wide variety of suitable techniques, including the techniques discussed above in connection with the preparation of the compounds of Formulas Va and/or Vb. Thus, exemplary removal techniques include, for example, base hydrolysis, acid hydrolysis, or hydrogenation.

Examples of the above process involving methods for removal of the secondary hydroxyl from compounds of Formulas VIIa and VIIb are provided in FIG. 4. In this regard, compound 11 is reacted with activating reagent Ac₂O in the presence of triethylamine, DMAP, and dichloromethane to provide intermediate 12 having an acetylated secondary hydroxyl group. Subsequently, the acetylated intermediate is hydrogenated with molecular hydrogen in the presence of Pd(OH)₂, effectively removing the secondary hydroxyl group to give the intermediate 13. Intermediate 13 can be hydrolyzed with K₂CO₃ and EtOH to yield intermediate 14. Intermediate 14 can be further hydrolyzed with NaOH in THF and water to provide compound 15 which may be converted to Alvimopan, or intermediate 13 can be hydrolyzed directly under suitable conditions to compound 15.

In accordance with another embodiment of the present invention, there are provided processes for preparing compounds of Formula VIc, Formula VIId, or mixtures thereof:

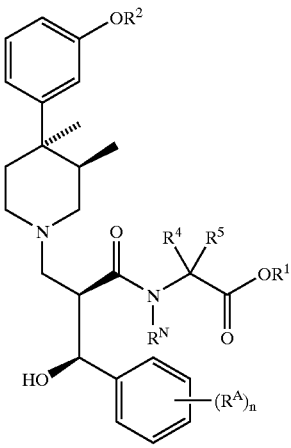

VIIc

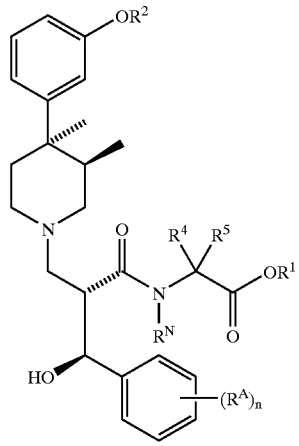

VIId wherein:
each $R^1$ is, independently, H, alkyl, aryl, aralkyl, heteroaryl, or heterocyclyl;
each $R^2$ is, independently, H or a hydroxyl protecting group;
each $R^4$, $R^5$, and $R^N$ is, independently, H, alkyl, or aralkyl;
each $R^A$ is, independently, halo, alkyl, halo-substituted alkyl alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and
n is 0 to 5;
or a salt thereof;
comprising contacting a compound of Formula III:

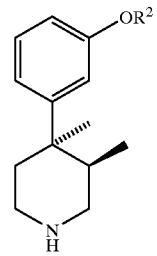

III with a compound of Formula VIIIb:

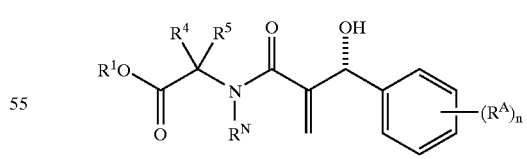

Figure 5:
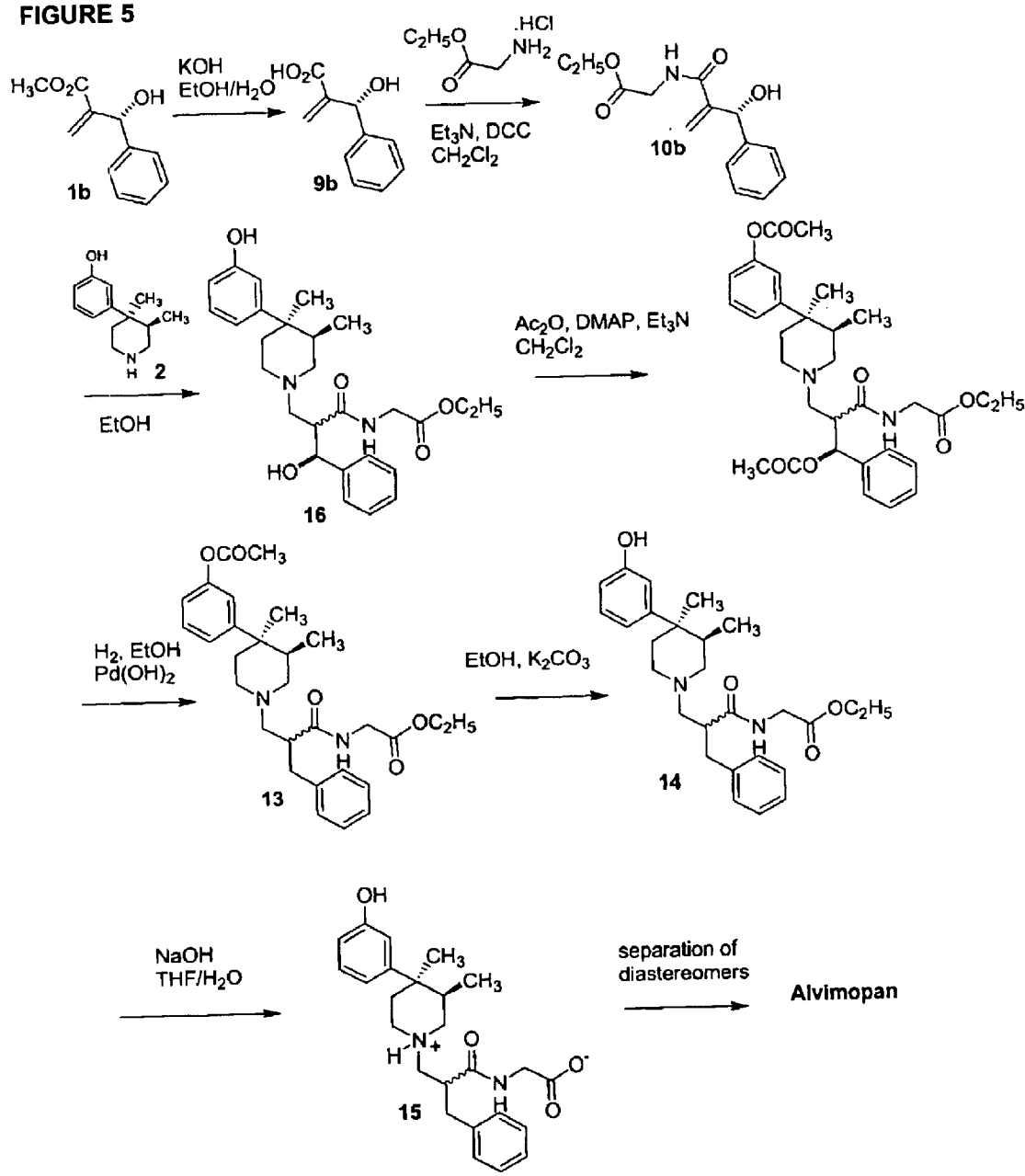

VIIIb for a time and under conditions effective to provide the compound of Formula VIc, the compound of Formula VIId, or the mixture thereof. A synthetic procedure that exemplifies the above preparatory process is depicted in FIG. 5.

In the above process, each $R^1$ is, independently, H, alkyl, aryl, aralkyl, heteroaryl, or heterocyclyl, each $R^1$ is, independently, hydrogen or a hydroxyl protecting group. In certain preferred embodiments, each $R^1$ is, independently, alkyl, aryl, aralkyl, heteroaryl, or heterocyclyl, with alkyl being more preferred. In even more preferred embodiments, each $R^1$ is, independently, methyl or ethyl. Also in the above process, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, $NHSO_2R$, $SO_2NRR$, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

In accordance with preferred embodiments, contacting the compound of Formula III with a compound of Formula VIIIb may be carried out in solution comprising a protic or aprotic solvent. In preferred form, contacting the compound of Formula III with a compound of Formula VIIIa may be carried out in a protic solvent.

According to certain preferred embodiments, contacting is carried out in a protic solvent, such as an alcohol. Suitable alcohols may have the formula $R^{10}OH$, where $R^{10}$ is an alkyl group as hereinbefore defined. Exemplary alcohols include methanol, ethanol, isopropanol, n-propanol, butanols, and the like. In preferred embodiments, the protic solvent is methanol. In other preferred embodiments, contacting is carried out in an aprotic solvent such as an ether. Any ether is suitable, including, for example non-cyclic ethers, and cyclic ethers such as THF.

Thus, contacting the compound of Formula III with a compound of Formula VIIIb in the above process may result in the preparation of a compound of Formula VIIc, a compound of Formula VIId, or a mixture of compounds of Formulas VIIc and VIId, i.e., a mixture of diastereomers.

Contacting the compound of Formula III with a compound of Formula VIIIb may be conducted under conditions of temperature and time effective to provide compounds of Formulas VIIc and/or VIId. The particular temperatures and times may vary, depending, for example, on the particular Formula III and Formula VIIIb compounds involved, as well as the particular solvent employed. In preferred form, the reaction may be conducted at a temperature of from about −78° C. to about 150° C., with from about −20° C. to about 50° C. being more preferred. The reaction may be conducted for a suitable period of time, for example, from about 1 minute to about 7 days, preferably from about 30 minutes to about 48 hours. The reaction may be monitored by standard analytical techniques, such as thin layer chromatography (TLC).

In embodiments in which a mixture of compounds of Formula VIIc and VIId are prepared, the present processes may further include a step for separating the compounds of Formula VIIc and Formula VIId. For example, a diastereomeric mixture of compounds of Formulas VIIc and VIId may be separated using any suitable method in the art. In some embodiments, separation may be carried out by chiral column chromatography, HPLC, recrystallization, or classical resolution methods. Other methods for separating the diastereomeric mixtures would be readily apparent to one skilled in the art, once placed in possession of the present disclosure.

In the above process, the compound of Formula VIIb may be provided, for example, by a process which comprises contacting a compound having the formula:

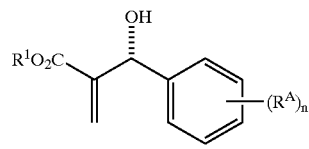

wherein each $R^1$ is, independently, H, alkyl, aryl, aralkyl, heteroaryl, or heterocyclyl; with a compound having the formula:

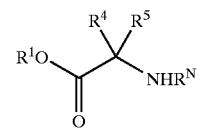

where each $R^1$, $R^4$, $R^5$, $R^N$, $R^A$ and n is as previously defined, for a time and under conditions effective to provide the compound of Formula VIIIb.

Contacting the above compounds to provide a compound of Formula VIIIb may be carried out in a protic solvent, such as an alcohol, or in an aprotic solvent such as an ether. Suitable alcohols and ethers include those discussed above. The contacting may be conducted under conditions of temperature and time effective to provide a compounds of Formula VIIIb. The particular temperatures and times may vary, depending, for example, on the particular starting materials involved, as well as the particular solvent employed. In preferred form, the reaction may be conducted at a temperature of from about −20° C. to about 50° C., with from about 0° C. to about 25° C. being more preferred. The reaction may be conducted for a suitable period of time, for example, from about 5 minutes to about 48 hours, preferably from about 30 minutes to about 24 hours. The reaction may be monitored by standard analytical techniques, such as thin layer chromatography (TLC).

The compounds of Formulas VIIc and/or VIId may undergo further transformations in accordance with the methods of the present invention. For example, the secondary hydroxyl group in the compounds of Formulas VIIc and/or VIId may be removed. Thus, the present invention further provides additional processes for preparing compounds of Formula IXa, compounds of Formula IXb, or mixtures thereof:

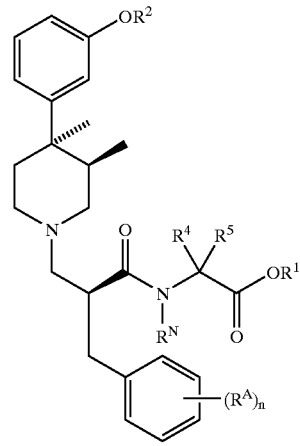

IXa

IXb

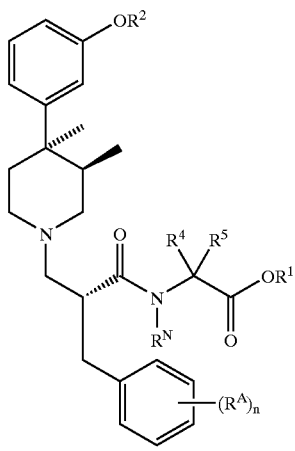

wherein:

each R¹ is, independently, H, alkyl, aryl, aralkyl, heteroaryl, or heterocyclyl;

each R² is, independently, H or a hydroxyl protecting group;

each R⁴, R⁵, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising providing a compound of Formula VIc, a compound of Formula VId, or a mixture thereof:

VIIc

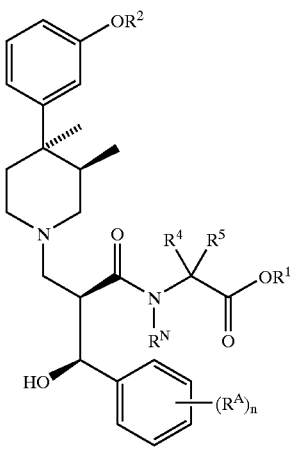

VIId

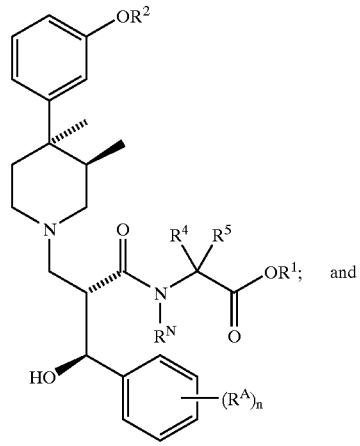
and substituting the secondary hydroxyl group of the compound of Formula VIIc, the compound of VIId, or the mixture thereof with hydrogen to provide the compound of Formula IXa, the compound of Formula IXb, or the mixture thereof.

In the above process, each R¹ is, independently, H, alkyl, aryl, aralkyl, heteroaryl, or heterocyclyl, each R² is, independently, hydrogen or a hydroxyl protecting group. Also in the above process, each R⁴, R⁵, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each R⁴, R⁵, $R^N$ and R is H. Also in preferred embodiments, n is 0.

In the above process, the compound of Formula VIIc and/or VIId may be provided, for example, by a process as described above, including by a process which comprises contacting a compound of Formula III:

III

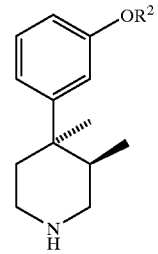

with a compound of Formula VIIIb:

VIIIb

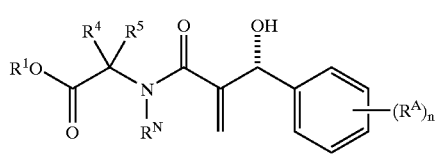

where each R¹, R², R⁴, R⁵, $R^N$, $R^A$ and n is as previously defined, for a time and under conditions effective to provide said compound of Formula VIIc, said compound of Formula VIId, or said mixture thereof.

Substitution or removal of the secondary hydroxyl with hydrogen may be carried out by any of a wide variety of suitable techniques, including the techniques discussed above. Thus, exemplary substitution methods include, for example, hydrogenation, ionic dehydroxylation and radical deoxygenation, using methods and reagents as discussed above.

The substitution hydrogenation reaction may be conducted under conditions of temperature and time effective to provide compounds of Formulas IXa and/or IXb. The particular temperatures and times may vary, depending, for example, on the particular Formula VIIa and/or VIIb compounds involved, the particular hydrogenating agent, as well as the particular solvent employed. In preferred form, the reaction may be conducted at a temperature of from about −78° C. to about 150° C., with from about −20° C. to about 50° C. being more preferred. The reaction may be conducted for a suitable period of time, for example, from about 1 minute to about 7 days, preferably from about 5 minutes to about 48 hours. The reaction may be monitored by standard analytical techniques, such as thin layer chromatography (TLC).

As described above, substituting can also include activating the secondary hydroxyl group prior to removal by converting the secondary hydroxyl group to a group having the formula —$OR^3$ wherein each $R^3$ is as previously defined, and substituting the —$OR^3$ group with hydrogen. Substituting the —$OR^3$ group with hydrogen can be accomplished by any of the aforementioned methods such as, for example, hydrogenation, ionic dehydroxylation, or radical deoxygenation.

In an alternate embodiment, substituting of the secondary hydroxyl group with hydrogen may also involve contacting a compound of Formula VIIc, a compound of Formula VIId, or a mixture thereof with an activating reagent for a time and under conditions effective to provide a compound of Formula Xc, a compound of Formula Xd, or a mixture thereof:

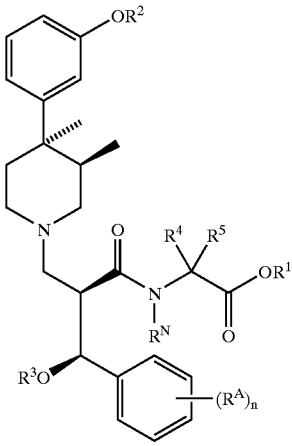

Xc

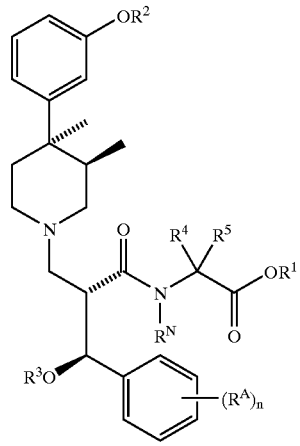

Xd wherein each $R^1$, $R^2$, $R^4$, $R^5$, $R^A$, $R^N$ and n is as previously defined, and each $R^3$ is, independently, a hydroxyl activating group; and contacting the compound of Formula Xc, the compound of Formula Xd, or the mixture thereof with a hydrogenating reagent for a time and under conditions effective to provide the compound of Formula Xc, the compound of Formula Xd, or the mixture thereof.

As with compounds discussed above, suitable activating reagents include reagents that are capable of replacing the hydrogen of the secondary hydroxyl group with a hydroxyl activating group in the compounds of Formulas VIIc and VIId. Examples of suitable activating reagents include alkyl anhydrides, such as, for example, acetic anhydride ($Ac_2O$), propionic anhydride, and trifluoroacetic anhydride, alkyl vinyl ethers, such as dihydopyran, trialkylsilyl halides, such as chlorotrimethylsilane, and alkyl alcohols, such as methanol and ethanol, and the like.

The activation reaction may be conducted under conditions of temperature time effective to provide compounds of Formulas Xc and/or Xd. The particular temperatures and times may vary, depending, for example, on the particular Formula VIIc and/or VIId compounds involved, the particular activating agent, as well as the particular solvent employed. In preferred form, the reaction may be conducted at a temperature of from about −78° C. to about 100° C., with from about 0° C. to about 25° C. being more preferred. The reaction may be conducted for a suitable period of time, for example, from about 5 minutes to about 24 hours, preferably from about 1 hour to about 3 hours. The reaction may be monitored by standard analytical techniques, such as thin layer chromatography (TLC).

As with the embodiments discussed above, suitable hydrogenating reagents include compounds that effect hydrogenation, ionic dehydroxylation, radical deoxygenation, or other similar processes. An example of a suitable hydrogenating reagent includes molecular hydrogen and a Pd catalyst such as $Pd(OH)_2$, a Pt catalyst such as $PtO_2$, or a Ni catalyst such as Raney-type Nickel. Other hydrogenating reagents can include, in ionic hydrogenations, for example, silicon hydride species, such as, for example, dimethylethylsilane, in the presence of a Lewis acid, such as, for example, $B(C_6F_5)_3$, and in radical deoxygenations, for example, tin hydride species, such as, for example, tributyl tin hydride, in the presence of a radical initiator, such as AIBN (free radical initiator).

In embodiments of the above process, each $R^2$ is, independently, a hydroxyl protecting group that may be removed from the compounds of Formula VIIc and/or VIId.

Removal of the hydroxyl protecting group may be carried out by any of a wide variety of suitable techniques, including the techniques discussed above. Thus, exemplary removal techniques include, for example, base hydrolysis, acid hydrolysis, or hydrogenation.

In accordance with another embodiment of the present invention, there are provided processes for preparing compounds of Formula IXa, Formula IXb, or mixtures thereof:

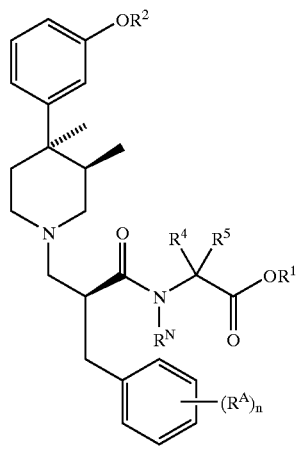

IXa

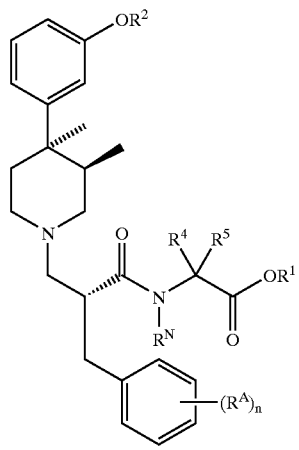

IXb wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, aryl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof;

comprising contacting a compound of Formula III:

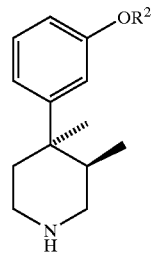

III with a compound of Formula XII:

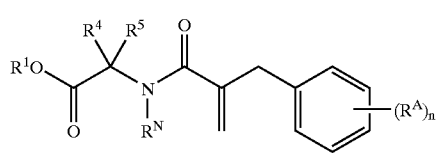

XII for a time and under conditions effective to prepare compounds of Formula IXa, compounds of Formula IXb, or mixtures thereof.

In the above process, each $R^1$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl. Each $R^1$ can be, for example, an alkyl group, such as methyl, ethyl or 2-methylpropyl.

In the above process, each $R^4$, $R^5$, and $R^N$ is, independently, H, alkyl, or aralkyl, each $R^A$ is, independently, halo, alkyl, halo-substituted alkyl, alkenyl, alkynyl, aryl, heteroaryl, heterocyclyl, OR, C(O)R, C(O) OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

In accordance with preferred embodiments, contacting the compound of Formula III with a compound of Formula XII may be carried out in solution comprising a protic or aprotic solvent. Suitable protic and aprotic solvents include the solvents discussed above. In preferred form, contacting the compound of Formula III with a compound of Formula XII may be carried out in a protic solvent.

According to certain preferred embodiments, contacting is carried out in a protic solvent, such as an alcohol. Suitable alcohols may have the formula $R^{10}OH$, where $R^{10}$ is an alkyl group as hereinbefore defined. Exemplary alcohols include methanol, ethanol, isopropanol, n-propanol, butanols, and the like. In preferred embodiments, the protic solvent is methanol. In other preferred embodiments, contacting is carried out in an aprotic solvent such as an ether. Any ether is suitable, including, for example non-cyclic ethers, and cyclic ethers such as THF.

Thus, contacting the compound of Formula III with a compound of Formula XII in the above process may result in the preparation of a compound of Formula IXa, a compound of Formula IXb, or a mixture of compounds of Formulas IXa and IXb, i.e., a mixture of diastereomers.

Contacting the compound of Formula III with a compound of Formula XII may be conducted under conditions of temperature and time effective to provide compounds of Formulas IXa and/or IXb. The particular temperatures and times may vary, depending, for example, on the particular Formula III and Formula XII compounds involved, as well as the particular solvent employed. In preferred form, the reaction may be conducted at a temperature of from about −20° C. to about 200° C., with from about 25° C. to about 150° C. being more preferred. The reaction may be conducted for a suitable period of time, for example, from about 1 hour to about 7 days, preferably from about 24 hours to about 48 hours. The reaction may be monitored by standard analytical techniques, such as thin layer chromatography (TLC).

In certain preferred embodiments, contacting the compound of Formula III with a compound of Formula XII is conducted in the presence of microwave radiation.

In the above process, the compound of Formula XII may be provided, for example, by a process which comprises contacting a compound having the formula: contacting a compound having the formula:

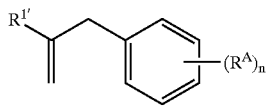

wherein each $R^1$ is, independently, —C(O)X, and X is halo, —OR$^1$, or OC(O)R$^1$; and each $R^1$ is, independently, H, alkyl, aryl, aralkyl, heteroaryl, or heterocyclyl; with a compound having the formula:

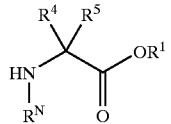

where each $R^4$, $R^5$, $R^N$, $R^A$ and n is as previously defined, for a time and under conditions effective to prepare said compound of Formula XII.

Contacting the above compounds to provide a compound of Formula XII may be carried out in a protic solvent, such as an alcohol, or in an aprotic solvent such as an ether. Suitable alcohols and ethers include those discussed above. The contacting may be conducted under conditions of temperature and time effective to provide compounds of Formula XII. The particular temperatures and times may vary, depending, for example, on the particular starting materials involved, as well as the particular solvent employed. In preferred form, the reaction may be conducted at a temperature of from about −20° C. to about 50° C., with from about 0° C. to about 25° C. being more preferred. The reaction may be conducted for a suitable period of time, for example, from about 5 minutes to about 48 hours, preferably from about 30 minutes to about 24 hours. The reaction may be monitored by standard analytical techniques, such as thin layer chromatography (TLC).

Figure 6:
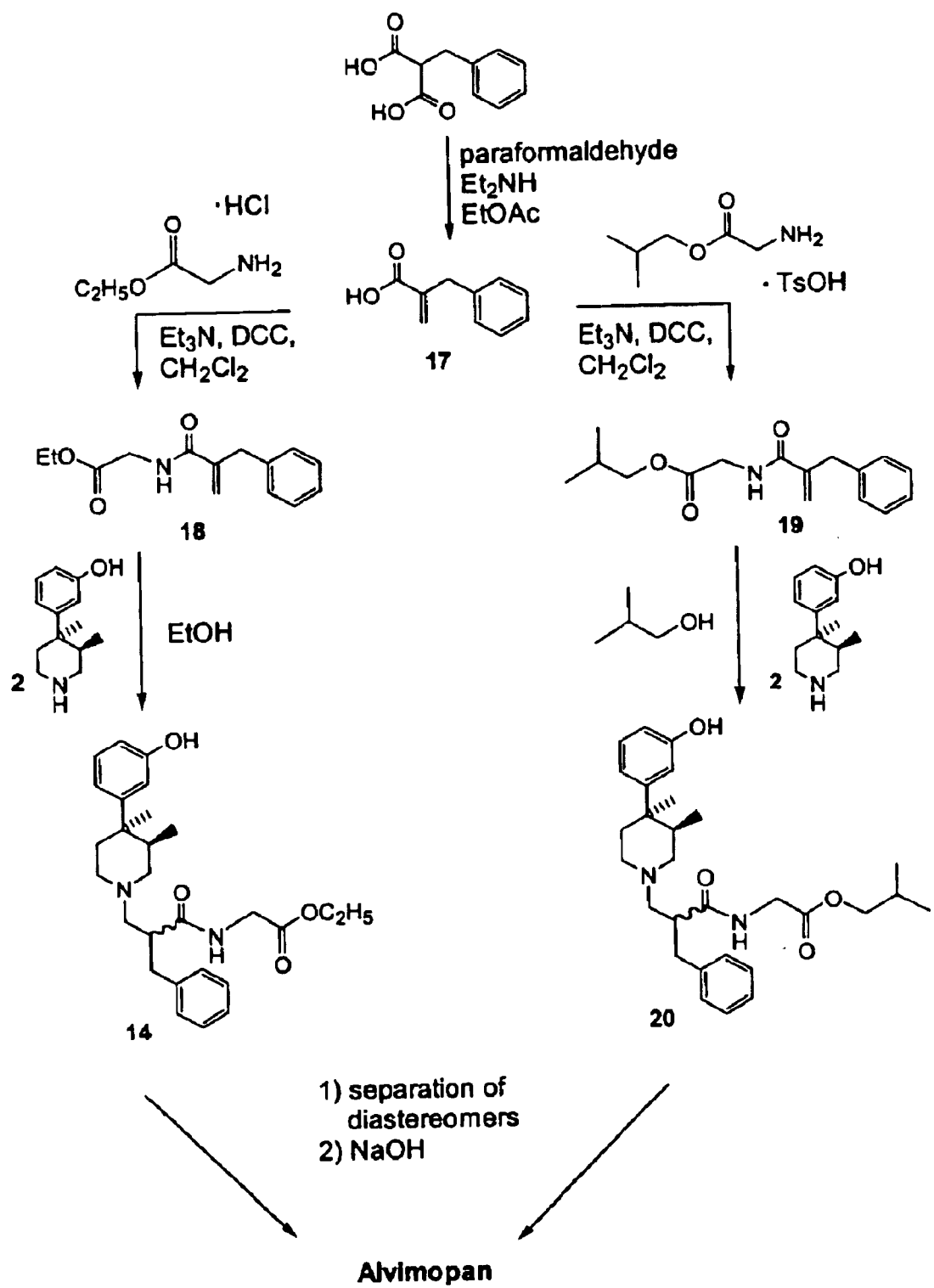

Examples of the above process are provided in FIG. 6, which shows the conjugate addition of 2 to the amide 18 obtained in two steps and high overall yield from benzyl malonic acid. The conjugate addition performed in refluxing ethanol (b.p.: 78° C.) was slow, but the addition afforded the desired product 14 in 42% yield after seven days of reaction. To increase the rate of the reaction, 2 was added to the ester 19 (obtained by coupling of the acid 17 with glycine isobutyl ester under standard conditions) in refluxing isobutyl alcohol (b.p.: 108° C.). Product 20 was obtained in 64% yield after 3 days of reaction.

There are also provided, in accordance with the present invention, compounds of the formula IIa, IIb, IIc and IId:

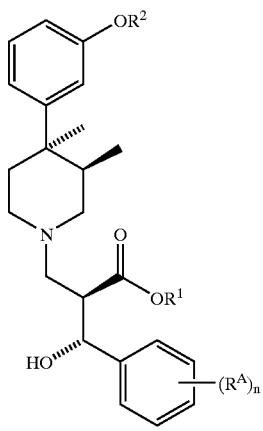

IIa

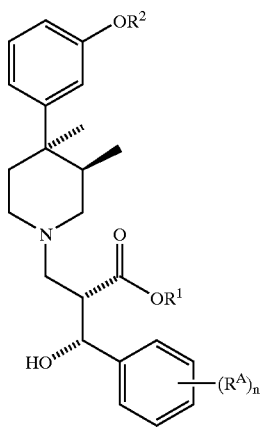

IIb

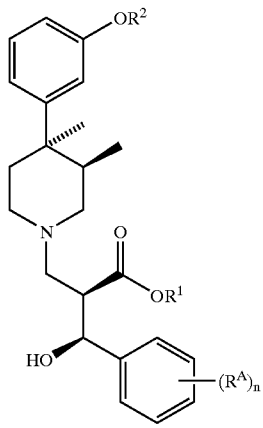

IIc

-continued

IId

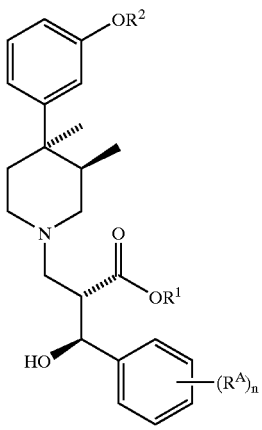

VIb

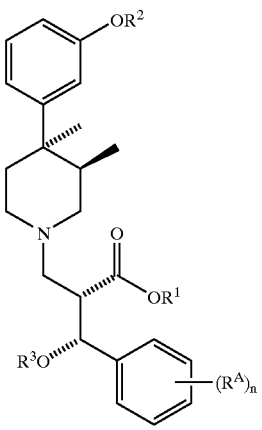

VIc

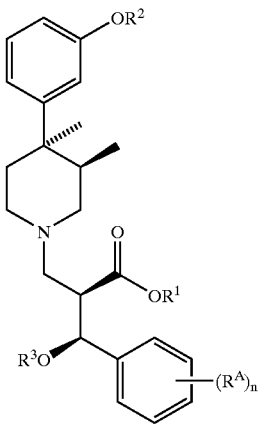

VId

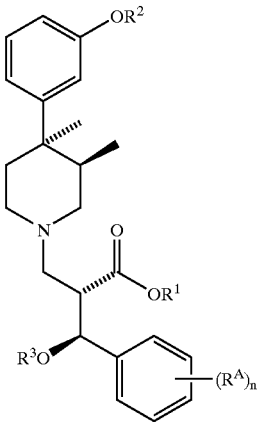

wherein:
  each $R^1$ is, independently, H, alkyl, aryl, aralkyl, heteroaryl, or heterocyclyl;
  each $R^2$ is, independently, H or a hydroxyl protecting group;
  each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is independently, H, alkyl, aryl, aralkyl, heteroaryl, or heterocyclyl; and
  n is 0 to 5;
or a salt thereof.

In the above compounds of formulas IIa, IIb, IIc and IId, each $R^1$ is, independently, hydrogen, alkyl, aryl, aralkyl, heteroaryl, or heterocyclyl. In certain preferred embodiments, each $R^1$ is, independently, alkyl, aryl, aralkyl, heteroaryl, or heterocyclyl. In even more preferred embodiments, each $R^1$ is, independently, an alkyl group, such as methyl or ethyl.

Also in the above compounds of formulas IIa, IIb, IIc and IId, each $R^2$ is, independently, H or a hydroxyl protecting group. In certain preferred embodiments, each $R^2$ is H.

In the above compounds, each $R^A$ is, independently, H, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each R is H. Also in preferred embodiments, n is 0.

In further embodiments of the present invention, there are provided compounds of the Formula VIa, VIb, VIc and VId:

VIa

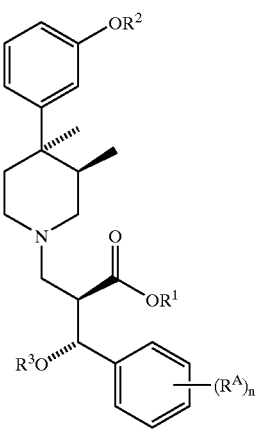

wherein:
  each $R^1$ is, independently, H, alkyl, aryl, aralkyl, heteroaryl, or heterocyclyl;
  each $R^2$ is, independently, H or a hydroxyl protecting group;
  each $R^3$ is, independently, a hydroxyl activating group;
  each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and
  n is 0 to 5;
or a salt thereof.

In the above compounds of Formulas VIa, VIb, VIc and VId, each $R^1$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl. In even more preferred embodiments, each $R^1$ is, independently, an alkyl group, such as methyl, or ethyl.

Also in the above compounds, each $R^2$ is, independently, H or a hydroxyl protecting group. In certain preferred embodiments, each $R^2$ is H.

In the above compounds of Formulas VIa, VIb, VIc and VId, each $R^3$ is, independently, a hydroxyl activating group. In certain preferred embodiments, each $R^3$ is, independently, alkylcarbonyl, arylcarbonyl, aralkylcarbonyl, heteroarylcarbonyl, heterocyclylcarbonyl, C(S)O-aryl, or $R^Z{}_3Si—$, wherein each $R^Z$ is, independently, alkyl or aryl, with alkylcarbonyl being more preferred. Even more preferably, each $R^3$ is $—C(O)CH_3$.

In the above compounds, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each R is H. Also in preferred embodiments, n is 0.

There are also provided by the present invention compounds of Formulas XIa and XIb:

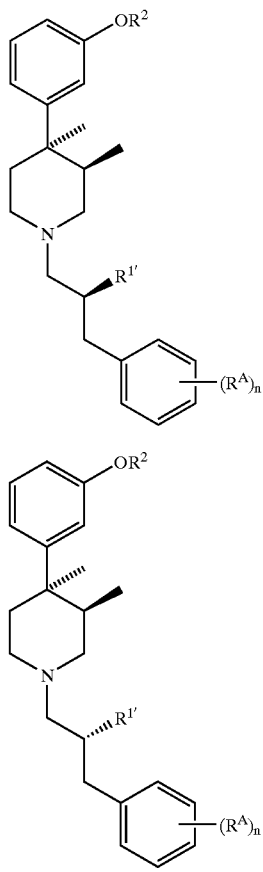

wherein:
each $R^{1'}$ is, independently, C(O)X, and X is halo, $—OR^1$, or $—OC(O)R^1$;
each $R^1$ is, independently, H, alkyl, aryl, aralkyl, heteroaryl, or heterocyclyl;
each $R^2$ is, independently, a hydroxyl protecting group;
each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

In the above compounds of Formulas XIa and XIb, each $R^{1'}$ is, independently, independently, —C(O)X, where X is halo, $—OR^1$, or $—OC(O)R^1$, each $R^1$ is independently H, alkyl, aryl, aralkyl, heteroaryl, or heterocyclyl, and each $R^2$ is independently a hydroxyl protecting group. In certain preferred embodiments, each $R^1$ is, independently, alkyl, aryl, aralkyl, heteroaryl, or heterocyclyl. Even more preferably, each $R^1$ is, independently, an alkyl group, such as methyl, or ethyl.

In the above compounds, each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, with H being preferred, and n is an integer ranging from 0 to 5 (and all combinations and subcombinations of ranges and specific integers therein). In preferred embodiments, n is 0.

In still further embodiments, there are provided compounds of the Formulas VIa, VIb, VIc and VId:

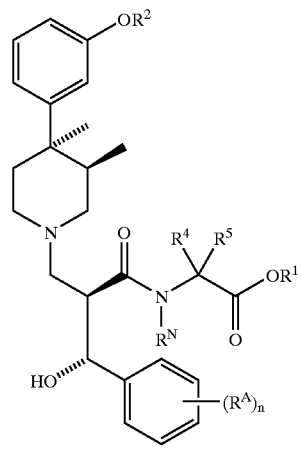

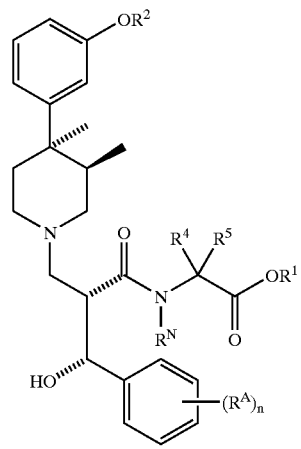

-continued

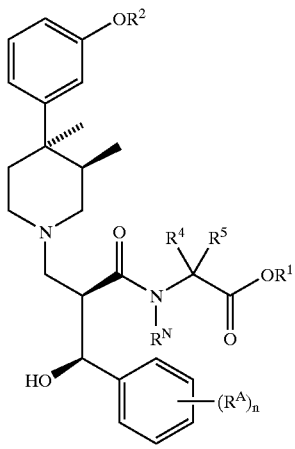

VIIc

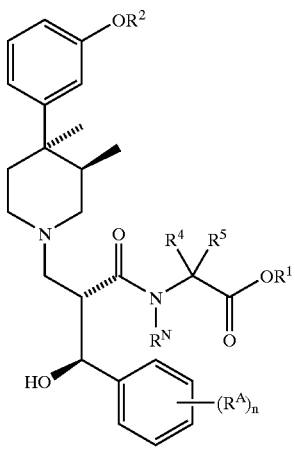

VIId wherein:
  each R¹ is, independently, H, alkyl, aryl, aralkyl, heteroaryl, or heterocyclyl;
  each R² is, independently, H or a hydroxyl protecting group;
  each $R^4$, $R^5$, and R is, independently, H, alkyl, or aralkyl;
  each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R s, independently, H, alkyl, aryl, aralkyl, heteroaryl, or heterocyclyl; and
  n is 0 to 5;
  or a salt thereof.

In the above compounds of Formulas VIIa, VIIb, VIIc and VIId, each R¹ is, independently, H, alkyl, aryl, aralkyl, heteroaryl, or heterocyclyl, and each $R^N$ is, independently, H, alkyl, aryl, aralkyl, heteroaryl, or heterocyclyl. In certain preferred embodiments, each R¹ is, independently, alkyl, aryl, aralkyl, heteroaryl, or heterocyclyl. Each R¹ can be, for example, an alkyl group, such as methyl, or ethyl.

Also in the above compounds, each R² is, independently, H or a hydroxyl protecting group. In certain preferred embodiments, each R² is H.

In the above compounds, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O) OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

There are also provided by the present invention compounds of Formulas VIIIa and VIIIb:

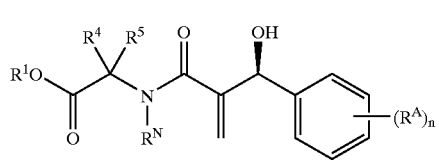

VIIIa

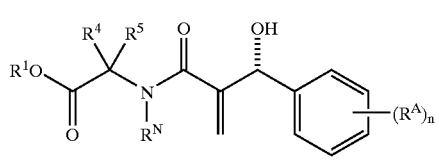

VIIIb wherein:

each R¹ is, independently, H, alkyl, aryl, aralkyl, heteroaryl, or heterocyclyl;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

In the above compounds of Formulas VIIIa and VIIIb, each R¹ is, independently, H, alkyl, aryl, aralkyl, heteroaryl, or heterocyclyl, and each $R^N$ is, independently, H, alkyl, aryl, aralkyl, heteroaryl, or heterocyclyl. In certain preferred embodiments, each R¹ is, independently, alkyl, aryl, aralkyl, heteroaryl, or heterocyclyl. Even more preferably, each R¹ is, independently, an alkyl group, such as methyl, or ethyl.

In the above compounds, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O) OR, OC(O)R, NHC(O)R, NHSO₂R, SO₂NRR, aminocarbonyl, amino, nitro, cyano, or SR, wherein each R is, independently, H, alkyl, aryl, aralkyl, heteroaryl, or heterocyclyl, with H being preferred, and n is an integer ranging from 0 to 5 (and all combinations and subcombinations of ranges and specific integers therein). In preferred embodiments, n is 0.

In still further embodiments, there are provided compounds of the Formulas Xa, Xb, Xc and Xd:

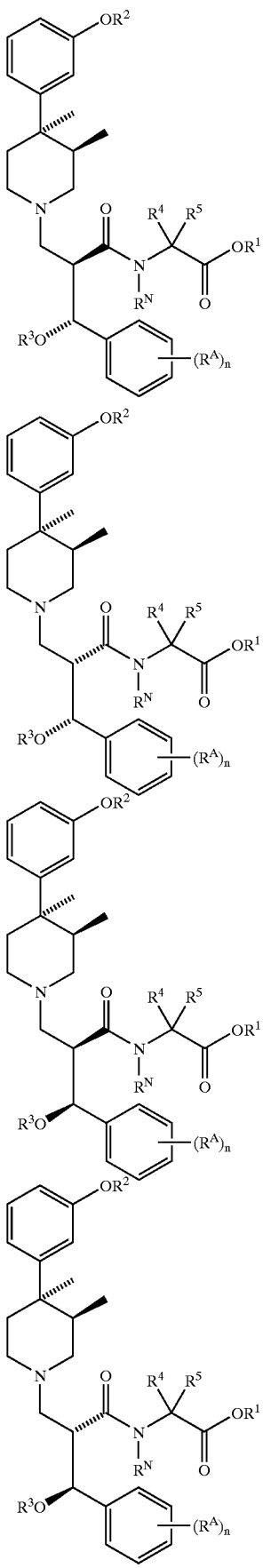

Xa

Xb

Xc

Xd wherein:

each $R^1$ is, independently, H, alkyl, aryl, aralkyl, heteroaryl, or heterocyclyl;

each $R^2$ is, independently, H or a hydroxyl protecting group;

each $R^3$ is, independently, a hydroxyl activating group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, $NHSO_2R$, $SO_2NRR$, aminocarbonyl, amino, nitro, cyano, or SR, wherein each R is, independently, H, alkyl, aryl, aralkyl, heteroaryl, or heterocyclyl; and n is 0 to 5;

or a salt thereof.

In the above compounds of Formulas Xa, Xb, Xc and Xd, each $R^1$ is, independently, H, alkyl, aryl, aralkyl, heteroaryl, or heterocyclyl, each $R^2$ is, independently, hydrogen or a hydroxyl protecting group, and each RN is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl. Even more preferably, each $R^1$ is, independently, an alkyl group, such as methyl or ethyl. Preferably, each $R^2$ is, independently, a hydroxyl protecting group.

In the above compounds, each $R^3$ is, independently, a hydroxyl activating group. In certain preferred embodiments, each $R^3$ is, independently, alkylcarbonyl, arylcarbonyl, aralkylcarbonyl, heteroarylcarbonyl, heterocyclylcarbonyl, C(S)O-aryl, or $R^Z_3Si—$, where each $R^Z$ is, independently, alkyl, or aryl, with alkylcarbonyl being more preferred. Even more preferably, each $R^3$ is —C(O)$CH_3$.

In the above compounds of Formulas Xa, Xb, Xc and Xd, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, $NHSO_2R$, $SO_2NRR$, aminocarbonyl, amino, nitro, cyano, or SR, wherein each R is, independently, H, alkyl, aryl, aralkyl, heteroaryl, or heterocyclyl, with H being preferred, and n is an integer ranging from 0 to 5 (and all combinations and subcombinations of ranges and specific integers therein). In preferred embodiments, n is 0.

The present invention further provides compounds of Formulas IXa and IXb:

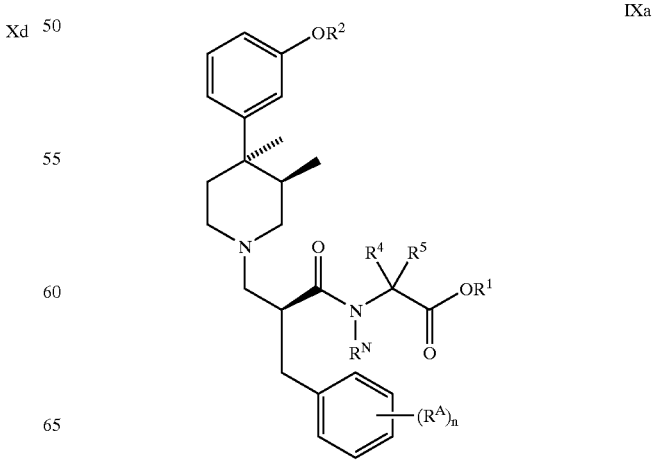

IXa

IXb

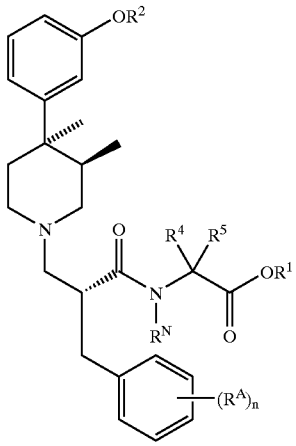

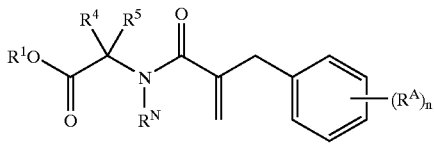

wherein:

each $R^1$ is, independently, H, alkyl, aryl, aralkyl, heteroaryl, or heterocyclyl;

each $R^2$ is, independently, H a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

In the above compounds of Formulas IXa and IXb, each $R^1$ is, independently H, alkyl, aryl, aralkyl, heteroaryl, or heterocyclyl, and each $R^N$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl. Even more preferably, each $R^1$ is, independently, an alkyl group, such as methyl or ethyl.

Also in the above compounds, each $R^2$ is, independently, H or a hydroxyl protecting group. In certain preferred embodiments, each $R^2$ is, independently, a hydroxyl protecting group, with alkyl, aryl, aralkyl, heteroaryl, heterocyclyl, alkylcarbonyl, arylcarbonyl, aralkylcarbonyl, heteroarylcarbonyl, heterocyclylcarbonyl, or silyl protecting groups being preferred.

In the above compounds, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each R is H. Also in preferred embodiments, n is 0.

The present invention further provides compounds of Formula XII:

XII wherein:

each $R^1$ is, independently, H, alkyl, aryl, aralkyl, heteroaryl, or heterocyclyl;

each $R^2$ is, independently, H or a hydroxyl protecting group;

each $R^4$, $R^5$, and $R^N$ is, independently, H, alkyl, or aralkyl;

each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl; and n is 0 to 5;

or a salt thereof.

In the above compounds of Formula XII, each $R^1$ is, independently, H, alkyl, aryl, aralkyl, heteroaryl, or heterocyclyl. In certain preferred embodiments, each $R^1$ is, independently, alkyl, aryl, aralkyl, heteroaryl, or heterocyclyl. Even more preferably, each $R^1$ is, independently, an alkyl group, such as methyl, ethyl or 2-methylpropyl.

In the above compounds, each $R^4$, $R^5$, and $R^N$ is, independently, H, alkyl, or aralkyl; each $R^A$ is, independently, halo, alkyl, halo-substituted alkyl, alkenyl, alkynyl, aryl, heteroaryl, heterocyclyl, OR, C(O)R, C(O)OR, OC(O)R, NHC(O)R, NHSO$_2$R, SO$_2$NRR, aminocarbonyl, amino, nitro, cyano, or SR, wherein each R is, independently, H, alkyl, aryl, aralkyl, heteroaryl, or heterocyclyl, and n is an integer ranging from 0 to 5 (and all combinations and subcombinations of ranges and specific integers therein). In preferred embodiments, each $R^4$, $R^5$, $R^N$ and R is H. Also in preferred embodiments, n is 0.

Compounds within the scope of the present invention including, for example, compounds of Formulas Ia, Ib, IIa, IIb, IIc, IId, Va, Vb, VIa, VIb, VIc, VId, VIIa, VIIb, VIIc, VIId, IXa, IXb, Xa, Xb, Xc, Xd, XIa and XIb, and particularly compounds of Formulas IIa, IIb, IIc, IId, VIIa, VIIb, VIIc and VIId, may also exhibit significant activity as opioid antagonist compounds, including mu, kappa and delta opioid antagonist activity, and thereby may desirably possess therapeutic value, for example, in the treatment of gastro-intestinal motility disorders. In particular, compounds of the present invention may be useful in blocking peripheral opioid receptors, thereby providing utility for preventing and/or treating ileus. The term "ileus", as used herein, refers to the obstruction of the bowel or gut, especially the colon. See, e.g., *Dorland's Illustrated Medical Dictionary*, p. 816, 27th ed. (W. B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W. B. Saunders Company, Philadelphia 1988). Ileus may be diagnosed by the disruption of normal coordinated movements of the gut, resulting in failure of the propulsion of intestinal contents. See, e.g., Resnick, *J. Am. J. of Gastroenterology* 1997,92, 751 and Resnick, *J. Am. J. of Gastroenterology*, 1997,92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, E. D. Jr. *Digestive Diseases and Sciences* 1990, 35, 121). "Post-surgical ileus", which may follow surgery such as laparotomy, may be characterized by such symptoms as, for example, obstruction of the gut, particularly in the colon, resulting in nausea, vomiting, lack of passage of flatus and/or stools, abdominal distention and lack of bowel sounds. This condition generally lasts from about 3 to about 5 days, hit may endure longer, including up to about one week. Longer durations are generally characteristic of a more severe form of ileus, termed post-surgical paralytic ileus, which may affect other portions of the GI tract in addition to the colon. Similarly, post-partum ileus is a common problem for women in the period following childbirth, and is thought to be caused by similar fluctuations in natural opioid levels as a result of birthing stress. "Post-partum ileus" generally refers to obstruction of the gut, particularly the colon, following parturition. Both natural and surgically-assisted procedures during parturition may lead to post-partum ileus treated by the present invention. Symptoms of postpartum ileus and post-surgical ileus are similar.

Compounds of the present invention may also be useful in preventing and/or treating peripheral opiate induced side effects. These side effects may be induced by administration of an opiate such as morphine to a mammal. The opiate induced side effects may include, for example, constipation, nausea, and vomiting. Thus, compounds of this invention may be useful for treating one or more opiate induced side effects. Compounds as described herein may also be useful in the treatment of irritable bowel syndrome, non-ulcer dyspepsia, and idiopathic constipation. Compounds of the invention do not substantially pass through the blood-brain barrier and therefore do not mitigate the opioid's effect on central (brain and spinal cord) opioid receptors. Consequently, these characteristics indicate that the compounds will also be substantially free of other centrally mediated effects. Other conditions that may be treated or prevented with compounds of the present invention, and techniques for formulating and administering such compounds, are described for example, in copending U.S. application Ser. No. 09/725,708, filed Nov. 29, 2000, now allowed, and copending U.S. application Ser. No. 09/725,661, filed Nov. 29, 2000, now allowed, the disclosures of each of which are hereby incorporated herein by reference, in their entireties.

In certain preferred embodiments, compounds of the present invention are peripheral opioid antagonist compounds, and preferably, mu opioid antagonist compounds. The term peripheral designates that the compound acts primarily on physiological systems and components external to the central nervous system, i.e., the compound preferably does not readily cross the blood-brain barrier. In preferred form, the peripheral opioid antagonist compounds employed in the methods of the present invention exhibit high levels of activity with respect to gastrointestinal tissue, while exhibiting reduced, and preferably substantially no, central nervous system (CNS) activity. The term "substantially no CNS activity", as used herein, means that less than about 20% of the pharmacological activity of the peripheral opioid antagonist compounds employed in the present methods is exhibited in the CNS. In preferred embodiments, the peripheral opioid antagonist compounds employed in the present methods exhibit less than about 15% of their pharmacological activity in the CNS, with less than about 10% being more preferred. In even more preferred embodiments, the peripheral opioid antagonist compounds employed in the present methods exhibit less than about 5% of their pharmacological activity in the CNS, with about 0% (i.e., no CNS activity) being still more preferred.

Accordingly, embodiments of the present invention are directed to pharmaceutical compositions involving mu opioid antagonist compounds, as well as methods involving the administration to a patient of a mu opioid antagonist compound. The methods of the present invention may be used to treat patients who are also being administered compounds that may slow gut motility including, for example, opiates and/or opioids, such as opioid analgesics, prior to, during, and subsequent to the onset of ileus. The administration of such opiate or opioid compounds may induce bowel dysfunction which, in turn, may delay recovery from ileus, including postoperative ileus. The methods of the present invention may also be used to treat patients who have not received any exogenous opiates and/or opioids. Thus, in certain embodiments, the present methods comprise administering a compound to patients who have not received any opioid analgesic drugs including, for example, any mu opioid agonists.

Compounds as described herein may be administered by any means that results in the contact of the active agent(s) with the agents' sit or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

Tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols and mixtures thereof, and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying techniques which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

Although the proper dosage of compounds of this invention will be readily ascertainable by one skilled in the art, once armed with the present disclosure, by way of general guidance, for example, typically a daily dosage may range from about 0.001 to about 100 milligrams of the peripheral opioid antagonist (and all combinations and subcombinations of ranges and specific dosages therein), per kilogram of patient body weight. Preferably, a daily dosage may be from about 0.01 to about 10 milligrams of the opioid antagonist per kilogram of patient body weight.

EXAMPLES

The invention is further described in the following examples. All of the examples are actual examples. These examples are for illustrative purposes only, and are not to be construed as limiting the appended claims.

The following experimental details apply to examples below. All chemicals were reagent grade and used without further purification. Analytical thin-layer chromatography (TLC) was performed on silica gel glass plates (250 microns) from Analtech and visualized by UV irradiation and iodine. Flash chromatography was conducted with silica gel (200–400 mesh, 60 Å, Aldrich). Chromatographic elution solvent systems are reported as volume:volume ratios. All $^1$H NMR spectra were recorded at ambient temperature on a Bruker-300 MHz spectrometer. The results are reported in ppm on the $\delta$ scale, from TMS. Melting points were obtained in open capillary tubes on a MEL-TEMP II melting point apparatus and are uncorrected. LC-MS data were obtained using a LC Thermo Finnigan Surveyor-MS Thermo Finnigan AQA in either positive mode or negative mode. Solvent A: 10 mM ammonium acetate, pH 4.5; solvent B: acetonitrile; solvent C: methanol; solvent D: water; column Waters Xterra C18 MS 2.0×50 mm, detector: PDA X=220–300 nM. Gradient program (positive mode): t=0.00, 600 $\mu$L/min, 99% A-1% B; t=0.30, 600 $\mu$L/min, 99% A-1% B; t=5.00, 600 $\mu$L/min, 1% A-99% B; t=5.30, 600 $\mu$L/min, 1% A-99% B. Gradient program (negative mode): t=0.00, 600 $\mu$L/min, 9% A-1% B-90% D; t=0.30, 600 $\mu$L/min, 9% A-1% B-90% D; t=5.00, 600 $\mu$L/min, 99% B-1% D; t=5.30, 600 $\mu$L/min, 99% B-1% D.

Example 1

Preparation of Precursor (±)methyl 3-hydroxy-2-methylene-3-phenylpropanoate (1).

Diazabicyclo[2.2.2]octane (5.2 g, 0.046 mol, 0.15 eq) was added to a mixture of benzaldehyde (31.5 mL, 0.309 mol, 1 eq) and methyl acrylate (42 mL, 0.464 mol, 1.5 eq). The reaction mixture was then allowed to stir at room temperature for 7 days. The reaction mixture was purified by column chromatography (eluent: hexane/ethyl acetate=95:5) to give the desired product as colorless oil (42 g, 77%). $R_f$ 0.5 (hexane/ethyl acetate=7:3). $^1$H NMR $\delta$ (DMSO-d$_6$) 3.6 (s, 3H), 5.43 (m, 1H), 5.73 (m, 1H), 5.98 (s, 1H), 6.19 (s, 1H), 7.29 (m, 5H).

Preparative chromatographic enantioresolution of the compounds of Example 1 was carried out by chiral separation using Chiralpak AS; 80% heptane (Fisher 012783), 20% isopropanol (Fisher 010923); 0.75 mL/min; room temperature; 20 μL inj.; UV 210 nM.

(+)Methyl 3(S)-hydroxy-2-methylene-3-phenylpropanoate (1a).

$R_f$ 0.5 (hexane/ethyl acetate=7:3). $^1$H NMR δ (DMSO-d$_6$) 3.6 (s, 3H), 5.43 (m, 1H), 5.73 (m, 1H), 5.98 (s, 1H), 6.19 (s, 1H), 7.29 (m, 5H). Fraction 2, $t_R$=8.86 min, 98.8% ee. m.p 48° C. $[α]_D^{25}$=+107.5 (c. 0.01, MeOH).

(−)Methyl 3-hydroxy-2-methylene-3-phenylpropanoate (1b).

$R_f$ 0.5, hexane/ethyl acetate=7:3. $^1$H NMR δ (DMSO-d$_6$) 3.6 (s, 3H), 5.43 (m, 1H), 5.73 (m, 1H), 5.98 (s, 1H), 6.19 (s, 1H), 7.29 (m, 5H). Fraction 1, $t_R$=6.46 min, 99.8% ee. m.p 51° C. $[α]_D^{25}$ (1b)=−113.7 (c. 0.01, MeOH).

Example 2

Preparation of Methyl (αS,3R,4R)-4-(3-hydroxyphenyl)-3,4-dimethyl-α-(S-hydroxyphenylmethyl)-1-piperidinepropanoate (3a).

A solution of 1a (3.92 g; 0.020 mol; 1.05 eq), prepared according to Example 1, in methanol (10 mL) was added dropwise to a solution of (3R,4R)-3-(3,4-dimethyl-4-piperidinyl)phenol 2 (4 g; 0.019 mol, 1 eq) in methanol (50 mL). The mixture was stirred at room temperature under nitrogen for 60 h. The solvent was evaporated and the residual yellow oil was dried under high vacuum to yield crude product containing the 2 diastereoisomers 3a and 3b (see FIG. 2; ratio 3a/3b=5.66:1; HPLC conditions: column Chiralcel OD 4.6×250 mm; flow: 1 mL/min; mobile phase: 85% hexane/15% isopropanol; λ=276 nM; Inj. Vol: 20 μL; 3a: $t_R$=130.10 min, area: 85.5%; 3b: $t_R$=22.88 min, area: 14.5%).

The 2 diastereoisomers were separated by column chromatography (eluent: hexane/EtOAc=9/1). $R_f$ (3a) 0.27 (hexane/EtOAc=7:3); $R_f$ (3b) 0.18 (hexane/EtOAc=7:3). The major isomer 3a was obtained as white solid (4.33 g, 56%). $^1$H NMR δ (DMSO-d$_6$) 0.60(d, 3H), 1.25 (s, 3H), 1.45 (d, 1H), 1.95 (m, 1H), 2.08 (m, 1H), 2.40 (m, 2H), 2.60 (m, 1H), 2.75 (m, 3H), 2.90 (m, 1H), 3.30 (s, 3H), 4.60 (d, 1H), 5.80 (s, 1H), 6.50 (d, 1H), 6.60 (s, 1H), 6.70 (d, 1H), 7.10 (t, 1H), 7.30 (m, 5H), 9.16 (s, 1H). [M+H]$^+$398.2,: $t_R$=2.85 min; purity: 99%.

Example 3

Preparation of Methyl (αR,3R,4R)-4-(3-hydroxyphenyl)-3,4-dimethyl-α-(S-hydroxyphenylmethyl)-1-piperidinepropanoate (3b).

A solution of 1a (1.05 g; 0.005 mol; 1.12 eq), prepared according to Example 1, in tetrahydrofuran (3 mL) was added drop wise to a solution of (3R,4R)-3-(3,4-dimethyl-4-piperidinyl)phenol 2 (1 g; 0.0048 mol, 1 eq) in tetrahydrofuran (20 mL). The mixture was stirred at room temperature under nitrogen for 72 h. The solvent was evaporated and the residual yellow oil was dried under high vacuum. The 2 diastereoisomers were separated by column chromatography (eluent: hexane/EtOAc=85/15). $R_f$ (3a) 0.27 (hexane/EtOAc=7:3); $R_f$ (3b) 0.18 (hexane/EtOAc=7:3). The major isomer 3b was obtained as white solid (0.360 g, 18%). $^1$H NMR δ (DMSO-d$_6$) 0.57 (d, 3H), 1.10 (s, 3H), 1.40 (m, 1H), 1.75–1.90 (m, 2H), 2.00 (m, 2H), 2.25 (m, 1H), 2.45 (m, 2H), 2.80 (m, 1H), 2.95 (m, 1H), 3.55 (s, 3H), 4.61 (m, 1H), 5.57 (d, 1H), 6.50 (d, 1H), 6.63 (s, 1H), 6.66 (d, 1H), 7.05 (t, 1H), 7.28 (m, 5H), 9.15 (s, 1H).

Example 4

Preparation of Methyl (αS,3R,4R)-4-(3-hydroxyphenyl)-3,4-dimethyl-α-(R-hydroxyphenylmethyl)-1-piperidinepropanoate (7a).

A solution of the methyl ester 1b (3.92 g; 0.020 mol; 1.05 eq), prepared according to Example 1, in tetrahydrofuran (10 mL) was added dropwise to a solution of 2 (4 g; 0.019 mol, 1 eq) in tetrahydrofuran (50 mL) (note: the mixture was heated gently for solubilization]. The mixture was stirred at room temperature under nitrogen for 60 h. The solvent was evaporated and the residual yellow oil was dried under high vacuum to yield: the crude product containing the two diastereoisomers 7a and 7b (see FIG. 5; ratio 7a/7b=2.3:1; HPLC conditions: column Chiralcel OD 4.6×250 mm; flow: 1 mL/min; mobile phase: 85% hexane/15% isopropanol; λ=276 nM; Inj. Vol: 20 μL; 7a: $t_R$=15.91 min, area: 69.57%; 7b: $t_R$=11.37 min, area: 30.18%).

Methanol (100 mL) was added to the reaction mixture. The suspension was stirred for 3 h at room temperature. The solid was collected by filtration and washed with methanol (2×20 mL). This white solid corresponds to the minor isomer 7b (1.79 g, 23%). The filtrate was concentrated and the crude material was purified by column chromatography (eluent: hexane/EtOAc=9:1). $R_f$ (7a) 0.26 (hexane/EtOAc=7:3); $R_f$(7b) 0.35 (hexane/EtOAc=7:3). The major isomer 7a was obtained as white solid (3.83 g, 49%). $^1$H NMR δ(DMSO-d$_6$) 0.55(d, 3H), 1.15 (s, 3H), 1.40 (d, 1H), 1.68(m, 1H), 1.90 (m, 1H), 2.00–2.20 (m, 3H), 2.50 (m, 3H), 2.95 (m, 1H), 3.55 (s, 3H), 4.60 (m, 1H), 5.60 (s, 1H), 6.50 (d, 1H), 6.60 (s, 1H), 6.70 (d, 1H), 7.05 (t, 1H), 7.40 (m, 5H), 9.16 (s, 1H). [M+H]$^+$398.2,: $t_R$=2.93 min; purity: 99%.

Example 5

Preparation of Methyl (αR,3R,4R)-4-(3-hydroxyphenyl)-3,4-dimethyl-α-(R-hydroxyphenylmethyl)-1-piperidinepropanoate (7b).

A solution of the methyl ester 1b (0.98 g; 0.005 mol; 1.05 eq), prepared according to Example 1, in methanol (2 mL) was added drop wise to a solution of 2 (1.0 g; 0.048 mol, 1 eq) in methanol (10 mL). The mixture was stirred at room temperature under nitrogen for 48 h. [note: the crude product contained the 2 diastereoisomers 7a and 7b, see FIG. 3]. The precipitate was collected by filtration and washed with ether (2×20 mL). The white solid corresponds to the major isomer 7b (1.43 g, 74%). $R_f$ (7a) 0.26 (hexane/EtOAc=7:3); $R_f$(7b) 0.35 (hexane/EtOAc=7:3). $^1$H NMR δ (DMSO-d$_6$) 0.73 (d, 3H), 1.20 (s, 3H), 1.45 (d, 1H), 1.90–2.10 (m, 2H), 2.25 (t, 1H), 2.45 (m, 2H), 2.60–3.00 (m, 4H), 3.32 (s, 3H), 4.64 (m, 1H), 5.82 (s, 1H), 6.52 (d, 1H), 6.63 (s, 1H), 6.70 (s, 1H), 7.05 (t, 1H), 7.29 (m, 5H), 9.16 (s, 1H).

Example 6

Preparation of Methyl (αS,3R,4R)-4-(3-acetoxyphenyl)-3,4-dimethyl-α-(phenylmethyl)-1-piperidinepropanoate 5a Obtained From 3a.

Acetic anhydride (Ac$_2$O) (1.30 mL, 0.014 mol, 2.5 eq) was added drop wise to a cold (0° C.) solution of 3a (2.2 g; 0.005 mol; 1 eq), triethylamine (1.93 mL, 0.014 mol; 2.5 eq) and 4-dimethylaminopyridine (0.135 g, 0.001 mol; 0.2 eq) in dichloromethane (30 mL). The mixture was stirred under nitrogen for 3 h (the solution warmed slowly from 0° C. to room temperature). An aqueous saturated solution of sodium bicarbonate (40 mL) was added to the reaction mixture. The organic phase was separated, washed with brine (50 mL) and dried over sodium sulfate. Evaporation of the solvent afforded the crude diacylated product 4a (2.61 g, 98%) [$R_f$ 0.46 (hexane/EtOAc=7:3)] used for the next step without further purification.

A solution of 4a (2.46 g, 0.005 mol) in methanol (50 mL) was hydrogenated at 75 psi for 16 h in the presence of Pd(OH)$_2$ (1 g) [20 wt. % Pd (dry basis) on carbon wet]. The mixture was filtered through celite and the celite was washed with methanol. The filtrate was concentrated under vacuum. Ethyl acetate (200 mL) was added and the organic solution was washed with an aqueous saturated solution of sodium bicarbonate (150 mL). The organic solution was separated and dried over sodium sulfate. Evaporation of the solvent afforded an oil which was purified by column chromatography (eluent: hexane/EtOAc=9:1). The desired product 5a (see FIG. 2) was obtained as a solid (1.79 g, 82%). $R_f$ 0.32 (hexane/EtOAc=8:2). $^1$H NMR δ (CDCl$_3$) 0.70 (d, 3H), 1.28 (s, 3H), 1.55 (m, 1H), 1.93 (m, 1H), 2.30 (s, 3H), 2.30–2.50 (m, 3H), 2.60–3.00 (m, 7H), 3.54 (s, 3H), 6.90 (m, 2H), 7.10–7.30 (m, 7H). [M+H]$^+$ 424.3: $t_R$=4.32 min; purity: 99%.

Example 7

Preparation of Methyl (αS,3R,4R)-4-(3-acetoxyphenyl)-3,4-dimethyl-α-(phenylmethyl)-1-piperidinepropanoate 5a Obtained From 7a.

Acetic anhydride (1.30 mL, 0.014 mol, 2.5 eq) was added drop wise to a cold (0° C.) solution of 7a (2.2 g; 0.005 mol; 1 eq), triethylamine (1.93 mL, 0.014 mol; 2.5 eq.) and 4-dimethylaminopyridine (0.135 g, 0.0011 mol; 0.2 eq) in anhydrous dichloromethane (30 mL) (see FIG. 3). The mixture was stirred under nitrogen for 3 h (the solution warmed slowly from 0° C. to room temperature). An aqueous saturated solution of sodium bicarbonate (40 mL) was added to the reaction mixture. The organic phase was separated, washed with brine (50 mL) and dried over sodium sulfate. Evaporation of the solvent afforded the crude diacetylated product 8a (see FIG. 3) (2.38 g, 89%) [$R_f$ 0.46 (hexane/EtOAc=7:3)] used for the next step without further purification.

A solution of 8a (2.20 g, 0.0045 mol) in methanol (50 mL) was hydrogenated at 70 psi for 16 h in the presence of Pd(OH)$_2$ (1 g) [20 wt. % Pd (dry basis) on carbon wet]. The mixture was filtered through celite and the celite was washed with methanol. The filtrate was concentrated under vacuum. Ethyl acetate (200 mL) was added and the organic solution was washed with an aqueous saturated solution of sodium bicarbonate (150 mL). The organic solution was separated and dried over sodium sulfate. Evaporation of the solvent afforded an oil which was purified by column chromatography (eluent: hexane/EtOAc=9:1). The desired product 5a was obtained as a solid (1.62 g, 84%). $R_f$ 0.32 (hexane/EtOAc=8:2). $^1$H NMR δ (CDCl$_3$) 0.70 (d, 3H), 1.28 (s, 3H), 1.55 (m, 1H), 1.93 (m, 1H), 2.30 (s, 3H), 2.30–2.50 (m, 3H), 2.60–3.00 (m, 7H), 3.54 (s, 3H), 6.90 (m, 2H), 7.10–7.30 (m, 7H). [M+H]$^+$ 424.2,: $t_R$=4.35 min; purity: 97%.

Example 8

Preparation of Methyl (αR,3R,4R)-4-(3-acetoxyphenyl)-3,4-dimethyl-α-(phenylmethyl)-1-piperidinepropanoate 5b Obtained From 3b.

Acetic anhydride (0.30 mL, 0.003 mol, 2.5 eq) was added drop wise to a cold (0° C.) solution of 3b (0.500 g; 0.00125 mol; 1 eq), triethylamine (0.43 mL, 0.003 mol; 2.5 eq) and 4-dimethylaminopyridine (0.030 g, 0.0002 mol; 0.2 eq) in THF (10 mL) (see FIG. 2). The mixture was stirred under nitrogen for 3 h (the solution warmed slowly from 0° C. to room temperature). An aqueous saturated solution of sodium chloride (20 mL) was added to the reaction mixture. Ethyl acetate (30 mL) was added and the organic phase was separated, washed with brine and dried over sodium sulfate. Evaporation of the solvent afforded the crude diacetylated product 4b [$R_f$ 0.46 (hexane/EtOAc=7:3)] used for the next step without further purification.

A solution of 4b in methanol (10 mL) was hydrogenated at 70 psi for 16 h in the presence of Pd(OH)$_2$ (0.200 g) [20 wt. % Pd (dry basis) on carbon wet]. The mixture was filtered through celite and the celite was washed with methanol. The filtrate was poured into an aqueous saturated solution of sodium bicarbonate (100 mL). The aqueous phase was extracted with ethyl acetate (3×20 mL). The combined organic extracts were washed with brine and dried over sodium sulfate. Evaporation of the solvent afforded crude 5b used for the next step without further purification (0.160 g, 30% (overall yield, 2 steps)). $R_f$ 0.32 (hexane/EtOAc=8:2). $^1$H NMR δ (CDCl$_3$) 0.74 (d, 3H), 1.28 (s, 3H), 1.57 (m, 4H), 1.95 (m, 1H), 2.30 (s, 3H), 2.40–2.50 (m, 2H), 2.60–2.70 (m, 2H), 2.85–3.00 (m, 3H), 3.58 (s, 3H), 6.90–7.00 (m, 2H), 7.10–7.30 (m, 7H).

Example 9

Preparation of Methyl (αR,3R,4R)-4-(3-acetoxyphenyl)-3,4-dimethyl-α-(phenylmethyl)-1-piperidinepropanoate 5b Obtained From 7b.

Acetic anhydride (0.38 mL, 0.004 mol, 2.5 eq) was added drop wise to a cold (0° C.) solution of 7b (0.650 g; 0.0016 mol; 1 eq), triethylamine (0.57 mL, 0.004 mol; 2.5 eq) and 4-dimethylaminopyridine (0.040 g, 0.00032 mol; 0.2 eq) in a mixture dichloromethane (10 mL) and dimethylformamide (3 mL) (see FIG. 3). The mixture was stirred under nitrogen for 3 h (the solution warmed slowly from 0° C. to room temperature). An aqueous saturated solution of sodium chloride (20 mL) was added to the reaction mixture. The organic phase was separated, washed with a saturated solution of sodium bicarbonate, brine and dried over sodium sulfate. Evaporation of the solvent afforded the crude diacetylated product 8b [$R_f$=0.46 (hexane/EtOAc=7:3)] used for the next step without further purification.

A solution of 8b in methanol (10 mL) was hydrogenated at 50 psi for 16 h in the presence of Pd/C (0.200 g) [10 wt. % Pd (dry basis) on carbon wet]. The mixture was filtered through celite and the celite was washed with methanol. The filtrate was poured into an aqueous saturated solution of sodium bicarbonate (100 mL). The aqueous phase was extracted with ethyl acetate (3×20 mL). The combined organic extracts were washed with brine and dried over sodium sulfate. Evaporation of the solvent afforded crude 5b further purified by column chromatography (0.210 g, 30%). $R_f$=0.32 (hexane/EtOAc=8:2). $^1$H NMR δ (CDCl$_3$) 0.74(d, 3H), 1.28 (s, 3H), 1.57 (m, 4H), 1.95 (m, 1H), 2.30 (s, 3H), 2.40–2.50 (m, 2H), 2.60–2.70 (m, 2H), 2.85–3.00 (m, 3H), 3.58 (s, 3H), 6.90–7.00 (m, 2H), 7.10–7.30 (m, 7H).

Example 10

Preparation of Methyl (αS,3R,4R)-4-(3-hydroxyphenyl)-3,4-dimethyl-α-(phenylmethyl)-1-piperidinepropanoate (6a).

Potassium carbonate (1.46 g, 0.0105 mol, 3 eq) was added to a solution of 5a (1.49 g, 0.0035 mol, 1 eq) in methanol (15 mL) (see FIGS. 2 and 3). The suspension was stirred under nitrogen for 2 h. Water (200 mL) was added and the suspension was extracted with ethyl acetate (200 mL). The organic solution was washed with brine (100 mL), separated and dried over sodium sulfate. Evaporation of the solvent afforded the methyl ester 6a as a solid (1.17 g, 87% yield). $R_f$ 0.30 (hexane/EtOAc=8:2). $^1$H NMR δ (CDCl$_3$) 0.70 (d, 3H), 1.25 (s, 3H), 1.51 (d, 1H), 1.94 (m, 1H), 2.20–2.50 (m, 3H), 2.60–3.00 (m, 5H), 3.55 (s, 3H), 6.64 (d, 2H), 6.75 (s, 1H), 6.85 (s, 1H), 7.10–7.35 (m, 7H); [M+H]+382.2,: $t_R$=3.42 min; purity: 99%. (Chiral purity determination; HPLC conditions: column Chiralcel OD 4.6×250 mm; flow: 1 mL/min; mobile phase: 92.5% hexane/7.5% isopropanol; λ=254 nM; Inj. Vol: 20 μL; 6a (reference standard): $t_R$=27.97 min; 6b (reference standard): $t_R$=25.36 min; result: 6a/6b= 98.7/1.3 (% area pic calculation)].

Example 11

Preparation of (αS,3R,4R)-4-(3-hydroxyphenyl)-3,4-dimethyl-α-(phenylmethyl)-1-piperidinepropanoic acid (V-i) obtained from 5a.

A 2N aqueous solution of sodium hydroxide (2.9 mL, 0.0059 mol, 5 eq) was added drop wise to a cold (0° C.) solution of 5a (0.500 g, 0.00118 mol, 1 eq) in THF (10 mL) (see FIG. 2). The ice bath was removed after 10 minutes and the mixture was stirred at room temperature for 3 h. The mixture was then cooled (0° C.) and acidified to pH 6 using a 1N aqueous solution of HCl. The THF was evaporated under vacuum. The mixture was then stirred at 0° C. for 2 h. The precipitate was collected by filtration, washed with water (2×10 mL) and ether (2×10 mL). The desired compound V-i was obtained as a solid (0.310 g, 71%).

Example 12
Preparation of methyl(αR,3R,4R)-4-(3-hydroxyphenyl)-3,4-dimethyl-α-(phenylmethyl)-1-piperidinepropanoate (6b).

Potassium carbonate (0.156 g, 0.001 mol, 3 eq) was added to a solution of 5b (0.160 g, 0.0003 mol, 1 eq) in methanol (15 mL). The suspension was stirred under nitrogen for 2 h. Water (50 mL) was added and the suspension was extracted with ethyl acetate (100 mL). The organic solution was washed with brine (50 mL), separated and dried over sodium sulfate. Evaporation of the solvent afforded the methyl ester 6b as a solid (0.060 g, 41% yield). $R_f$ 0.30 (hexane/EtOAc=8:2). $^1$H NMR δ (CDCl$_3$) 0.73 (d, 3H), 1.26 (s, 3H), 1.51 (d, 1H), 1.94 (m, 1H), 2.20–2.35 (m, 2H), 2.40–2.50 (m, 2H), 2.55–2.70 (m, 2H), 2.80–3.00 (m, 3H), 3.58 (s, 3H), 6.60 (d, 1H), 6.75 (s, 1H), 6.85 (d, 1H), 7.10–7.30 (m, 7H).

Example 13
Preparation of Precursor 3(S)-hydroxy-2-methylene-3-phenylpropanoic Acid (9a).

A solution of potassium hydroxide (2.27 g, 0.040 mol, 1.3 eq) in water (45 mL) was added drop wise to a solution of 1a (6 g, 0.031 mol, 1 eq) in methanol (15 mL) (see FIG. 4). The mixture was stirred at room temperature for 15 h. The solution was then concentrated under vacuum. The aqueous phase was washed with ether (2×100 mL), acidified with 6N aqueous HCl solution and extracted with ether (3×100 mL). The combined organic extracts were washed with brine (100 mL) and dried over sodium sulfate. Evaporation of the solvent afforded a colorless oil which crystallized upon standing. The desired product 9a was obtained as a solid (5.34 g, 96%). $R_f$ 0.26 (hexane/EtOAc=6:4).). $^1$H NMR δ (DMSO-d$_6$) 5.41 (s, 1H), 5.61 (s, 1H), 5.93 (s, 1H), 6.15 (s, 1H), 7.22 (m, 5H), 12.45 (s, 1H). [MH]$^-$ 177.2: $t_R$=1.28 min; purity: 88%.

Example 14
Preparation of [[3(S)-hydroxy-2-methylene-1-oxo-3-phenylpropyl]amino]acetic Acid Ethyl Ester (10a).

Triethylamine (3.75 mL, 0.027 mol, 1.2 eq) was added to a suspension of glycine ethyl ester hydrochloride (3.44 g, 0.024 mol, 1.1 eq) in anhydrous dichloromethane (60 mL) (see FIG. 4). The mixture was stirred for 15 min at room temperature and then cooled to 0° C. (ice bath). Compound 9a (4 g, 0.022 mol, 1 eq) and dicyclohexylcarbodiimide (5.09 g, 0.02469 mol, 1.1 eq) were added successively to the reaction mixture which was stirred at room temperature for 17 h. The precipitate (dicyclohexylurea and triethylamine hydrochloride) was collected by filtration. The filtrate was washed with a 1N aqueous solution of HCl (50 mL), brine (50 mL) and dried over sodium sulfate. Evaporation of the solvent afforded an oil which was purified by column chromatography (eluent: hexane/EtOAc=6:4). The desired product 10a was obtained as a yellow oil (3.51 g, 60%). $R_f$ 0.25 (hexane/EtOAc=4:6). $^1$H NMR δ (CDCl$_3$) 1.25 (t, 3H), 3.63 (s, 1H), 4.02 (m, 2H), 4.17 (q, 2H), 5.49 (s, 1H), 5.58 (d, 1H), 5.96 (s, 1H), 6.86 (s, 1H), 7.65 (m, 5H).[M+H]$^+$ 264.1,: $t_R$=2.55 min; purity: 96%.

Example 15
Preparation of [[2(S/R)-[[4(R)-(3-hydroxyphenyl)-3(R),4-dimethyl-1-piperidinyl]methyl]-3-(S)-hydroxy-1-oxo-3-phenylpropyl]amino]acetic Acid Ethyl Ester (11).

A solution of compound 10a (3.18 g, 0.012 mol, 1 eq) in denatured ethanol (13 mL) was added drop wise to a solution of compound 2 (2.72 g, 0.013 mol, 1.1 eq) in denaturated ethanol (30 mL) (see FIG. 4). The solution was heated to reflux for 26 h. The mixture was then concentrated under vacuum affording a yellow oil which was purified by column chromatography (eluent: increasing polarity from hexane/EtOAc=8:2 to hexane/EtOAc=6:4). The desired product 11 present as mixture of 2 diastereoisomers was obtained as a solid (3.10 g, 55%). [Ratio of the 2 diastereoisomers=1.1:1; HPLC conditions: column Chiralpak AD 4.6×250 mm; flow: 1 mL/min; mobile phase: 85% hexane/15% isopropanol; λ=254 nM; Inj. Vol: 20 µL; pic 1: $t_R$=24.50 min, area: 53.42%; pic 1: t=30.27 min, area: 46.58%]. $R_f$ 0.26 (hexane/EtOAc=5:5). $^1$H NMR δ (CDCl$_3$) 0.70 (m, 3H), 1.25 (m, 6H), 1.60 (m, 1H), 2.0 (m, 1H), 2.10 (m, 1H), 2.20–2.45 (m, 2H), 2.50–3.05 (m, 4H), 3.7 (s, 1H), 3.90–4.25 (m, 4H), 4.85 (m, 0.5H), 5.3 (m, 0.5H), 5.70 (signal, 1H), 6.60–6.80 (m, 3H), 7.15 (t, 1H), 7.20–7.40 (m, 4H), 7.65 (s, 0.5H), 9.5 (s, 0.5H). [M+H]$^+$ 469.3 $t_R$=2.77 min; purity: 92%.

Example 16
Preparation of [[2(S/R)-[[4(R)-(3-acetoxyphenyl)-3(R),4-dimethyl-1-piperidinyl]methyl]-1-oxo-3-phenylpropyl]amino]acetic Acid Ethyl Ester (13).

Acetic anhydride (1.0 mL, 0.010 mol, 2.5 eq) was added drop wise to a cold (0° C.) solution of 11 (2 g; 0.004 mol; 1 eq), triethylamine (1.48 mL, 0.010 mol; 2.5 eq) and 4-dimethylaminopyridine (0.104 g, 0.0008 mol; 0.2 eq) in dichloromethane (40 mL) (see FIG. 4). The mixture was stirred under nitrogen for 3 h (the solution warmed slowly from 0° C. to room temperature). An aqueous saturated solution of sodium bicarbonate (10 mL) was added to the reaction mixture. The organic phase was separated, washed with brine and dried over sodium sulfate. Evaporation of the solvent afforded the crude diacetylated product 12 (2.22 g, 94%) [$R_f$ 0.37 (hexane/EtOAc=5:5)] used for the next step without further purification.

A solution of 12 (2 g, 0.0036 mol) in denatured ethanol (35 mL) was hydrogenated at 70 psi for 16 h in the presence of Pd(OH)$_2$ (1 g) [20 wt. % Pd (dry basis) on carbon wet]. The mixture was filtered through celite and the celite was washed with denatured ethanol. The filtrate was concentrated. Ethyl acetate (100 mL) was added to the reaction mixture. The organic solution was washed with an aqueous saturated solution of sodium bicarbonate (100 mL), brine (100 mL) and dried over sodium sulfate. Evaporation of the solvent afforded a crude solid which was purified by column chromatography (eluent: heptane/EtOAc=7:3). The desired compound 13 was obtained as a solid (1.11 g, 62%). $R_f$ 0.48 (hexane/EtOAc=5:5). $^1$H NMR δ (CDCl$_3$) 0.75 (m, 3H), 1.30 (m, 7H), 2.0–2.20 (m, 2H), 2.35 (s, 3H), 2.35–2.50 (m, 2H), 2.55–2.80 (m, 4H), 2.85–3.05 (m, 1H), 3.35 (m, 1H), 3.70–4.0 (m, 2H), 4.20 (m, 3H), 6.95 (m, 2H), 7.10–7.35 (m, 7H). [M+H]$^+$ 495.3,: $t_R$=3.27 min; purity: 97%.

Example 17
Preparation of [[2(S/R)-[[4(R)-(3-hydroxyphenyl)-3(R),4-dimethyl-1-piperidinyl]methyl]-1-oxo-3-phenylpropyl]amino]acetic Acid Ethyl Ester 14 Obtained From 13.

Potassium carbonate (0.268 g, 0.0019 mol, 3.8 eq) was added to a solution of 13 (0.270 g, 0.0005 mol, 1 eq) in denatured ethanol (10 mL) (see FIG. 4). The suspension was stirred under nitrogen for 3 h. Water (50 mL) was added and the suspension was extracted with ethyl acetate (2×50 mL). The organic solution was washed with brine (50 mL), separated and dried over sodium sulfate. Evaporation of the solvent afforded the crude ethyl ester 14 which was further purified by column chromatography (eluent: hexane/ethyl acetate=8:2). The desired compound 14 was obtained as a solid (0.150 g, 60%).$R_f$ 0.25 (hexane/EtOAc=6:4). $^1$H NMR δ (CDCl$_3$) 0.70 (m, 3H), 1.25 (m, 6H), 1.60 (m, 1H), 1.95–2.15 (m, 2H), 2.20–3.00 (m, 8H), 3.35 (m, 1H), 3.754.0 (m, 2H), 4.15 (m, 3H), 5.5 (signal, 1H), 6.60–6.85 (m, 3H), 7.25 (m, 5H), 9.10 (s, 1H). [M+H]+453.3,: $t_R$=2.90 min; purity: 96%. Compound 14 was present as a mixture of 2 diastereoisomers (3R,4R,αS+3R,4R,αR); Ratio of the 2 diastereoisomers=1.3:1; HPLC conditions: column Chiralpak AD 4.6×250 mm; flow: 1 mL/min; mobile phase: 85% hexane/15% isopropanol; λ=254 nM; Inj. Vol: 20 μL; pic 1: $t_R$=12.67 min, area: 44.47%; pic 2: $t_R$=20.35 min, area: 55.53%; 14a (3R,4R,αS) (reference standard): $t_R$=20.89 min; 14b (3R,4R,αR) (reference standard): $t_R$=12.95 min.

Example 18

Preparation of [[2(SIR)-[[4(R)-(3-Hydroxyphenyl)-3(R),4-dimethyl-1-piperidinyl]methyl]-1-oxo-3-phenylpropyl]amino]acetic Acid (15).

A 2N aqueous solution of sodium hydroxide (3 mL, 0.0060 mol, 5 eq) was added drop wise to a cold (0° C.) solution of 13 (0.600 g, 0.012 mol, 1 eq) in THF (10 mL) (see FIG. 4). The ice bath was removed after 10 minutes and the mixture was stirred at room temperature for 3 h. The mixture was then cooled (0° C.) and acidified to pH 6 using a 1N aqueous solution of HCl. The THF was evaporated under vacuum. The mixture was then stirred at 0° C. for 2 h. The precipitate was collected by filtration, washed with water (2×10 mL) and ether (2×10 mL). The desired compound 15 was obtained as a solid (0.372 g, 72%). $R_f$ 0.24 (dichloromethane/MeOH=8:2) $^1$H NMR δ (DMSO-$d_6$) 0.70 (m, 3H), 1.25 (m, 3H), 1.50 (m, 1H), 1.95 (m, 1H), 2.10–3.05 (m, 8H), 3.70 (m, 2H), 6.50–6.75 (m, 3H), 7.10 (m, 1H), 7.10–7.35 (m, 6H), 8.40 (s, 1H), 9.20 (s, 1H). [M+H]+ 425.2: $t_R$=2.43 min; purity: 99%.

Example 19

Preparation of 3(R)-hydroxy-2-methylene-3-phenylpropanoic Acid (9b).

A solution of potassium hydroxide (2.65 g, 0.047 mol, 1.3 eq) in water (60 mL) was added drop wise to a solution of 1b (7 g, 0.036 mol, 1 eq) in methanol (20 mL) (see FIG. 5). The mixture was stirred at room temperature for 15 h. The solution was then concentrated under vacuum. The aqueous phase was washed with ether (2×100 mL), acidified with 6N aqueous HCl solution and extracted with ether (3×100 mL). The combined organic extracts were washed with brine (100 mL) and dried over sodium sulfate. Evaporation of the solvent afforded a colorless oil which crystallized upon standing. The desired product 9b was obtained as a solid (6.29 g, 97%). $R_f$ 0.26 (hexane/EtOAc=6:4). $^1$H NMR δ (DMSO-$d_6$) 5.41 (s, 1H), 5.61 (s, 1H), 5.93 (s, 1H), 6.15 (s, 1H), 7.22 (m, 5H), 12.45 (s, 1H). [M−H]− 177.1, $t_R$=1.23 min; purity: 91%.

Example 20

Preparation of [[3(R)-hydroxy-2-methylene-1-oxo-3-phenylpropyl]amino]acetic Acid Ethyl Ester (10b).

Triethylamine (5.16 mL, 0.037 mol, 1.2 eq) was added to a suspension of glycine ethyl ester hydrochloride (4.74 g, 0.033 mol, 1.1 eq) in anhydrous dichloromethane (80 mL) (see FIG. 5). The mixture was stirred for 15 min at room temperature and then cooled to 0° C. (ice bath). A solution of compound 9b (5.5 g, 0.030 mol, 1 eq) in anhydrous dichloromethane (10 mL) and dicyclohexylcarbodiimide (7.00 g, 0.034 mol, 1.1 eq) were added successively to the reaction mixture which was stirred at room temperature for 17 h The precipitate (dicyclohexylurea and triethylamine hydrochloride) was collected by filtration. The filtrate was washed with a 1N aqueous solution of HCl (100 mL), brine (100 mL) and dried over sodium sulfate. Evaporation of the solvent afforded an oil which was purified by column chromatography (eluent: hexane/EtOAc=8:2). The desired product 10b was obtained as an oil (6.16 g, 76%). $R_f$ 0.29 (hexane/EtOAc=4:6). $^1$H NMR δ (CDCl$_3$) 1.25 (t, 3H), 3.63 (s, 1H), 4.02 (m, 2H), 4.17 (q, 2H), 5.49 (s, 1H), 5.58 (s, 1H), 5.96 (s, 1H), 6.86 (s, 1H), 7.25 (m, 5H). [M+H]+ 264.1:$t_R$=2.50 min; purity: 92%.

Example 21

Preparation of [[2(S/R)-[[4(R)-(3-hydroxyphenyl)-3(R),4-dimethyl-1-piperidinyl]methyl]-3-(S)-hydroxy-1-oxo-3-phenylpropyl]amino]acetic Acid Ethyl Ester (16).

A solution of compound 10b (1 g, 0.003 mol, 1 eq) in tetrahydrofuran (3 mL) was added drop wise to a solution of compound 2 (0.857 g, 0.004 mol, 1.1 eq) in tetrahydrofuran (10 mL) (see FIG. 5). The solution was heated to reflux for 48 h. The mixture was then concentrated under vacuum affording an oil which was purified by column chromatography (eluent: increasing polarity from hexane/EtOAc=8:2 to hexane/EtOAc=6:4). The desired product 16 present as mixture of 2 diastereoisomers was obtained as a solid (0.660 g, 34%). [Ratio of the 2 diastereoisomers=1.1:1; HPLC conditions: column Chiralpak AD 4.6×250 mm; flow: 1 mL/min; mobile phase: 85% hexane/15% isopropanol; λ=254 nM; Inj. Vol: 20 μL; pic 1: $t_R$=22.82 min, area: 46.96%; pic 2: $t_R$=34.73 min, area: 53.04%] $R_f$ 0.26 (hexane/EtOAc=5:5). $^1$H NMR δ (CDCl$_3$) 0.70 (2d, 3H), 1.25 (m, 6H), 1.55 (m, 1H), 2.0 (m, 2H), 2.15–2.40 (m, 2H), 2.40–2.95 (m, 4H), 3.70–4.00 (m, 1H), 4.15 (m, 3H), 4.85 (d, 0.5H), 5.30 (d, 0.5H), 5.90 (signal, 1H), 6.60 (m, 1H), 6.70 (s, 1H), 6.80 (d, 1H), 7.15 (t, 1H), 7.35 (m, 6H), 7.80 (s, 0.5H), 9.50 (s, 1H). [M+H]+ 469.5 $t_R$=2.63 min; purity: 97%.

Example 22

Preparation of 2-methylene-3-phenylpropanoic Acid (17).

A solution of benzylmalonic acid (20.0 g, 0.103 mol, 1 eq) and paraformaldehyde (4.94 g, 0.164 mol, 1.6 eq) in ethyl acetate (150 mL) was cooled (0° C.) and treated with diethylamine (10.65 mL, 0.103 mol, 1 eq) drop wise, keeping the reaction temperature below 20° C. (see FIG. 6). The reaction was then warmed to reflux for 90 min and cooled again on ice. The homogeneous solution was treated with water (20 mL) and concentrated aqueous HCl (12N) (9.0 mL, 0.108 mol) drop wise, keeping the reaction temperature below 10° C. The phases were then separated. The organic layer was washed with brine (100 mL), dried over sodium sulfate, filtered, and the filtrate concentrated under vacuum giving compound 17 as a white solid (15 g, 90%). $R_f$ 0.46 (hexane/EtOAc=7:3). $^1$H NMR (300 MHz, CDCl$_3$) δ 7.28 (m, 5H), 6.42 (s, 1H), 5.62 (s, 1H), 3.67 (s, 2H). [M−H]− 161.0: $t_R$=2.53 min; purity: 99%.

Example 23

Preparation of [[2-Methylene-1-oxo-3-phenylpropyl]amino]acetic Acid Ethyl Ester (18).

Triethylamine (3.10 mL, 0.022 mol, 1.2 eq) was added to a suspension of glycine ethyl ester hydrochloride (2.84 g, 0.020 mol, 1.1 eq) in anhydrous dichloromethane (100 mL) (see FIG. 6). The mixture was stirred for 15 min at room temperature and then cooled to 0° C. (ice bath). Compound 17 (3 g, 0.018 mol, 1 eq) and dicyclohexylcarbodiimide (4.19 g, 0.020 mol, 1.1 eq) were added successively to the reaction mixture which was stirred at room temperature for 17 h. The precipitate (dicyclohexylurea and triethylamine hydrochloride) was collected by filtration. The filtrate was washed successively with a saturated aqueous solution of sodium bicarbonate (100 mL), 1N aqueous solution of HCl (100 mL), brine (100 mL) and was then dried over sodium sulfate. Evaporation of the solvent afforded an oil which was purified by column chromatography (eluent: hexane/EtOAc=8:2). The desired product 18 was obtained as a solid (3.79 g, 83%). $R_f$=0.14 (hexane/EtOAc=7:3). m.p. 51° C. $^1$H NMR δ (CDCl$_3$) 1.25 (t, 3H), 3.65 (s, 2H), 4.05 (d, 2H), 4.20

(q, 2H), 5.30 (s, 1H), 5.85 (s, 1H), 6.30 (s, 1H), 7.15–7.35 (m, 5H). [M+H]⁺ 248.0, $t_R$=3.03 min; purity: 99.5%.

Example 24

Preparation of [[2(S/R)-[[4(R)-(3-hydroxyphenyl)-3(R),4-dimethyl-1-piperidinyl]methyl]-1-oxo-3-phenylpropyl] amino]acetic Acid Ethyl Ester 14 obtained from 18.

A solution of 2 (0.5 g, 0.0024 mol, 1 eq) and 18 (0.6 g, 0.0024 mol, 1 eq) in denaturated ethanol (15 mL) was refluxed for 7 days. Evaporation of the solvent afforded the crude ethyl ester 14 which was purified by column chromatography (eluent: hexane/ethyl acetate=8:2). The desired compound 14 was obtained as a solid (0.460 g, 42%). $R_f$=0.26 (hexane/EtOAc=6:4). ¹H NMR δ (CDCl₃) 0.70 (m, 3H), 1.25 (m, 6H), 1.60 (m, 1H), 1.95–2.15 (m, 2H), 2.20–3.00 (m, 8H), 3.35 (m, 1H), 3.75–4.0 (m, 2H), 4.15 (m, 3H), 5.3 (signal, 1H), 6.60–6.85 (m, 3H), 7.25 (m, 5H), 9.10 (s, 1H). [M+H]⁺ 453.3, $t_R$=2.90 min; purity: 98%. Compound 14 is present as a mixture of 2 diastereoisomers (3R,4R,αS+3R,4R,αR); Ratio of the 2 diastereoisomers= 1:1.2; HPLC conditions: column Chiralpak AD 4.6×250 mm; flow: 1 mL/min; mobile phase: 85% hexane/15% isopropanol; X=254 nM; Inj. Vol: 20 µL; pic 1: $t_R$=12.35 min, area: 55.59%; pic 2: $t_R$=19.82 min, area: 44.51%; 14a (3R,4R,αS) (reference standard): $t_R$=20.89 min; 14b (3R, 4R,αR) (reference standard): $t_R$=12.95 min.

Example 25

Preparation of [[2-Methylene-1-oxo-3-phenylpropyl]amino] acetic Acid 2-methylpropyl Ester (19).

Triethylamine (3.10 mL, 0.022 mol, 1.2 eq) was added to a suspension of 2-methylpropyl glycine, p-toluenesulfonic acid salt (6.17 g, 0.020 mol, 1.1 eq) in anhydrous dichloromethane (100 mL). The mixture was stirred for 15 min at room temperature and then cooled to 0° C. (ice bath). Compound 17 (3 g, 0.018 mol, 1 eq) and dicyclohexylcarbodiimide (4.19 g, 0.0203 mol, 1.1 eq) were added successively to the reaction mixture which was stirred at room temperature for 17 h. The precipitate (dicyclohexylurea and triethylamine hydrochloride) was collected by filtration. The filtrate was washed successively with a saturated aqueous solution of sodium bicarbonate (100 mL), 1N aqueous solution of HCl (100 mL), brine (100 mL) and was then dried over sodium sulfate. Evaporation of the solvent afforded an oil which was purified by column chromatography (eluent: hexane/EtOAc=8:2). The desired product 18 was obtained as a solid (4.01 g, 79%). $R_f$0.41 (hexane/EtOAc=7:3).). m.p. 35° C. ¹H NMR δ (CDCl₃) 0.95 (d, 6H), 1.95 (m, 1H), 3.65 (s, 2H), 3.90 (d, 2H), 4.05 (d, 2H), 5.30 (s, 1H), 5.85 (s, 1H), 6.30 (s, 1H), 7.20–7.40 (m, 5H). [M+H]⁺ 276.1, $t_R$=3.53 min; purity: 100%.

Example 26

Preparation of [[2(S/R)-[[4(R)-(3-hydroxyphenyl)-3(R),4-dimethyl-1-piperidinyl]methyl]-1-oxo-3-phenylpropyl] amino]acetic Acid 2-Methylpropylester (20).

A solution of 2 (0.5 g, 0.002 mol, 1 eq) and 19 (0.67 g, 0.002 mol, 1 eq) in 2-methyl-1-propanol (15 mL) was refluxed for 3 days (see FIG. 6). Evaporation of the solvent afforded the crude ester 20 which was purified by column chromatography (eluent: hexane/ethyl acetate=8:2). The desired compound 20 was obtained as a solid (0.750 g, 64%). $R_f$=0.32 (hexane/EtOAc=6:4). ¹H NMR δ (CDCl₃) 0.70 (m, 3H), 0.95 (m, 6H), 1.25 (s, 3H), 1.60 (m, 1H), 1.80–2.15 (m, 2H), 2.20–2.50 (m, 2H), 2.50–3.00 (m, 7H), 3.35 (m, 1H), 3.80–4.00 (m, 3H), 4.20 (m, 1H), 5.20 (signal, 1H), 6.60–6.80 (m, 3H), 7.15–7.30 (m, 6H), 9.10 (s, 1H). [M+H]⁺ 481.3: $t_R$=3.47 min; purity: 100%.

Biological Methods

The affinities of compounds of the present invention can be assessed by their ability to inhibit binding of radiolabeled ligands to membranes prepared from cells expressing individual cloned human opioid receptors.

Statistics:

Raw data collected in this study were total cpm of radioligand bound in the presence of various concentrations of the test compound. The concentration to give half-maximal stimulation (EC₅₀) was determined from a best nonlinear regression fit of the data to the equation, $$Y = \text{Bottom} + \frac{(\text{Top} - \text{Bottom})}{1 + 10^{X - LogEC50}}$$

where Y is the radiolabeled compound bound at each concentration of test compound, Bottom is the theoretical value in the presence of an infinite concentration of test compound, Top is the theoretical value in the absence of added test compound, X is the logarithm of the concentration of test compound, and LogEC50 is the log of test compound concentration at which the response (Y) is halfway between Bottom and Top. The nonlinear regression fit was performed using the program Prism® (GraphPad Software, San Diego, Calif.). The dissociation constants (K₁) for test compounds were determined from the EC₅₀ values by the equation, $$K_I = \frac{EC_{50}}{1 + \frac{[\text{ligand}]}{K_d}}$$

where [ligand] is the concentration of radiolabeled ligand and the $K_d$ is the dissociation constant for the radiolabeled ligand.

Since the distributions of the logarithms of EC₅₀ and K₁ values are Gaussian, statistical comparisons were therefore made of the logarithms. Means, standard deviations and 95% confidence intervals were determined for the logarithms and the antilogarithms were then obtained and reported.

Test Materials:

Naloxone was obtained from RBI/Sigma (Natick, Mass.). Methylnaltrexone was obtained from Mallinckrodt Chemical Inc. (St. Louis, Mo.). Expression vectors containing the cloned human opioid receptors were obtained from Ohmeda Pharmaceutical Products Division. Cells expressing the receptors were grown and harvested at Adolor Pharmaceutical Corp. Radioligands were obtained form Amersham Life Sciences (Piscataway, N.J.).

Methods:

1. Preparation of Membranes for Receptor Binding:

Chinese Hamster Ovary cells were stably transfected with the cloned human µ, δ, or κ opioid receptors. Human Embryonic Kidney cells were stably transfected with the cloned human receptor. Cells were harvested by scraping them from the culture flask, centrifuging them at 1000×g for 10 min, resuspending them in buffer A and centrifuging again to remove growth medium. The cells were resuspended again in buffer A and homogenized for less than 30 seconds using a Polytron Homogenizer (Brinkmann) at setting 1. The homogenate was centrifuged at 48,000×g for 10 min at 4° C. The pellets were resuspended at 1 mg of protein per mL of buffer A and aliquots stored at −80° C. until used. Buffer A was 50 mM Tris HCl, pH 7.8, containing 1.0 mM EGTA, 5 mM MgCl₂, 10 µg/mL leupeptin, 10

μg/mL pepstatin A, 200 μg/mL bacitracin, and 0.5 μg/mL aprotinin.

2. Inhibition of Receptor Binding by Test Compounds:

Opioid receptor binding assays contained 0.4–1 nM [³H] diprenorphine (30,000–50,000 dpm), test compound as appropriate, and membrane preparation in a total volume of 0.5 mL of Buffer A. Sufficient membrane preparation was used so that approximately 10% of added radioligand was bound in the absence of inhibitors. Non-specific binding was determined in the presence of 10 μM naloxone and was usually equal to or less than 10% of total binding. After incubation at room temperature for one hour, the samples were filtered through GF/B filters that had been pre-soaked in a solution of 0.5% (w/v) polyethylenimine and 0.1% (w/v) bovine serum albumin in water. The filters were rinsed 4 times with 1 mL of ice-cold 50 mM Tris pH 7.8 and radioactivity remaining on the filters determined by scintillation spectroscopy. $K_i$ values were determined by Cheng-Prusoff corrections of $IC_{50}$ values derived from nonlinear regression fits of 8 or 12 point titration curves using the program, Prism® (GraphPad Software).

Compounds were tested at 1.0 μM and/or 10 μM or were titrated. For titrations, eight or twelve serial dilutions of test compound were prepared from a stock solution of 1.0 mM compound dissolved in dimethyl sulfoxide. An initial 1:10 dilution was made into assay buffer and serial dilutions were prepared. For twelve point titrations, 1:3.15 dilutions were made in assay buffer ranging from either $3.2 \times 10^{-10}$ M to $1.0 \times 10^{-4}$ M or $3.2 \times 10^{-11}$ M to $1.0 \times 10^{-5}$ M. For eight point titrations, either 1:10 or 1:6 serial dilutions were prepared in assay buffer. For 1:10 dilutions, the concentration range was from $1.0 \times 10^{-12}$ M to $1.0 \times 10^{-4}$ M. For 1:6 dilutions, the concentration range was either $3.6 \times 10^{-10}$ M to $1.0 \times 10^{-4}$ M or $3.6 \times 10^{-11}$ to $1.0 \times 10^{-5}$ M. For all titrations, 50 μL of the dilution series was then transferred to assay mixtures containing a total final volume of 500 μL, so that the final range of concentrations tested was 10 fold less than the ranges listed above.

Figure 7:
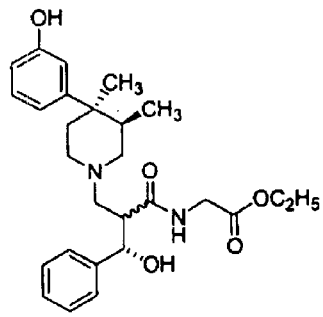
FIG. 7 shows the results of biological testing work for compounds in accordance with embodiments of the present invention.
Figure 7:
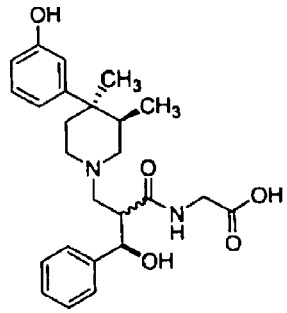
Figure 7:
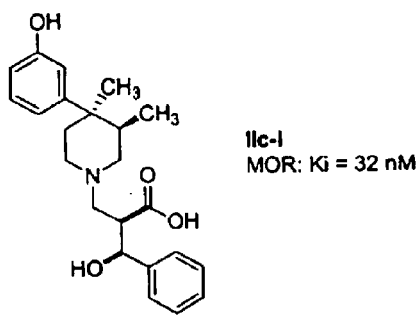
Figure 7:
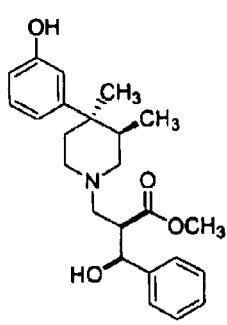
Figure 7:
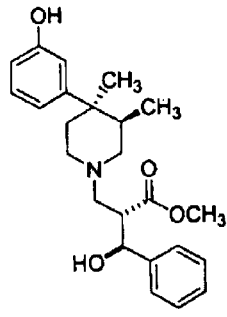
Figure 7:
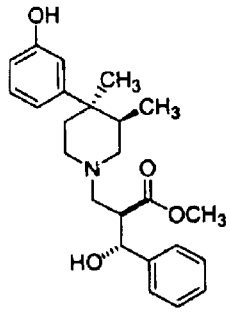
Figure 7:
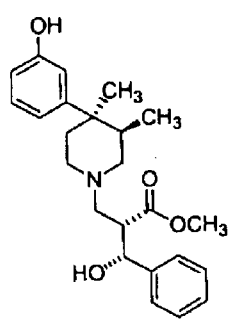

Binding affinities of selected compounds within the scope of the present invention toward μ opioid receptor (MOR) are indicated in FIG. 7. All of the tested compounds demonstrated modest to good affinity toward the μ opioid receptor (nanomolar range). The biological test work indicates that compounds IIc-ii, IId-i and IIa-i are μ opioid receptor antagonists, as determined by in vitro functional assay. As would be apparent to the ordinarily skilled artisan, once armed with the teachings of the present application, compounds VII-i, VII-ii and IIc-i are expected to also be μ opioid receptor antagonists.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A process for preparing a compound of Formula Ia, a compound of Formula Ib, or a mixture thereof:

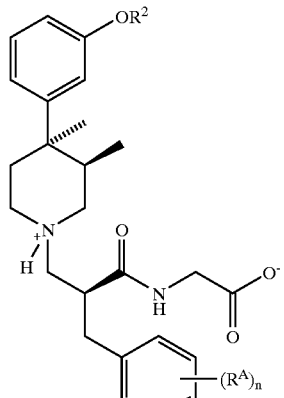

Ia

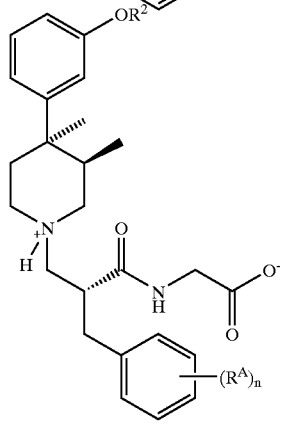

Ib wherein:

each $R^2$ is, independently, H or a hydroxyl protecting group;

each $R^A$ is, independently, halo, alkyl, halo-substituted alkyl, alkenyl, alkynyl, aryl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, or aralkyl; and n is 0 to 5;

or a salt thereof;

comprising:

(a) preparing a compound of Formula Va, a compound of Formula Vb, or a mixture thereof:

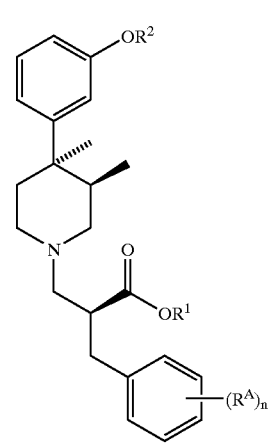

Va

-continued

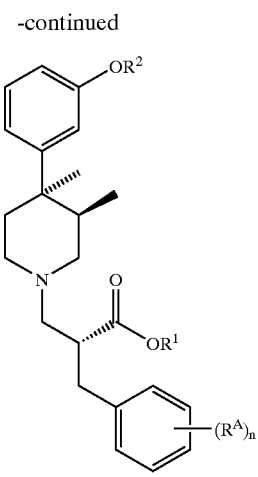

Vb wherein:

each $R^1$ is, independently, H, alkyl, aryl or aralkyl;

comprising providing a compound of Formula IIa, a compound of Formula IIb, or a mixture thereof:

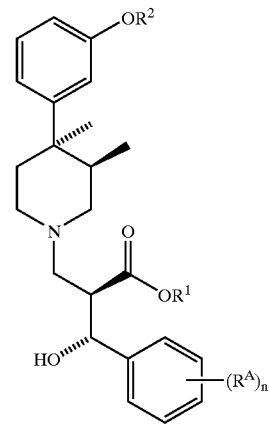

IIa

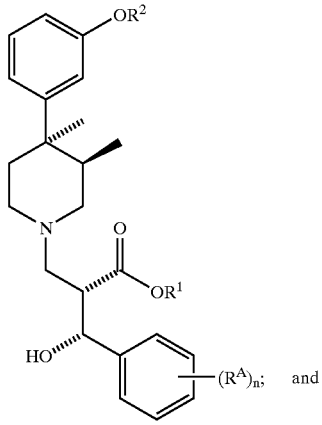

IIb; and substituting the secondary hydroxyl group of said compound of Formula IIa, said compound of Formula IIb, or said mixture thereof with hydrogen to provide said compound of Formula Va, said compound of Formula Vb, or said mixture thereof, wherein said substitution comprises hydrogenation, ionic dehydroxylation or radical deoxygenation;

(b) optionally converting —$OR^1$ of said compound of Formula Va, said compound of Formula Vb, or said mixture thereof to —X, where X is halo or —$OC(O)R^1$; and (c) selectively converting —$OR^1$, X, or —$OC(O)R^1$ of said compound of Formula Va, said compound of Formula Vb, or said mixture thereof, to —$NHCH_2COOH$, wherein said selective conversion comprises contacting the product from step (a) or optional step (b) with $NH_2CH_2COOH$ or an acid addition salt, ester or derivative thereof.

2. A process of claim 1 wherein each $R^1$ is, independently, alkyl, aryl, or aralkyl.

3. A process of claim 2 wherein each $R^1$ is, independently, alkyl.

4. A process of claim 3 wherein each $R^1$ is, independently, methyl or ethyl.

5. A process of claim 1 wherein $R^2$ is H.

6. A process of claim 1 wherein $R^1$ is H.

7. A process of claim 6 wherein said selective conversion is carried out in the presence of a coupling agent.

8. A process of claim 1 wherein n is 0.

9. A process for preparing a compound of Formula Ia, a compound of Formula Ib, or a mixture thereof:

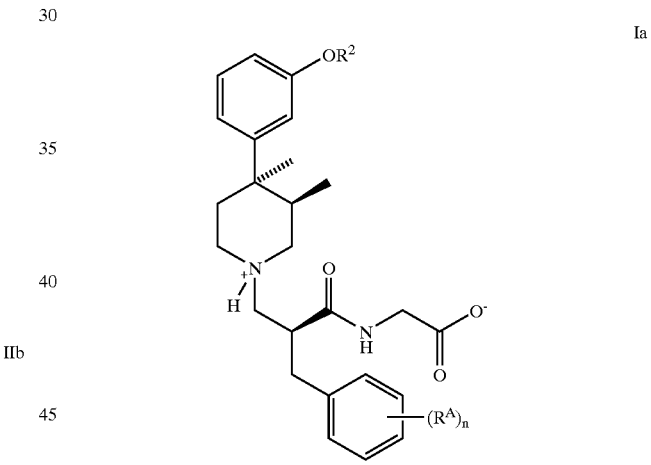

Ia

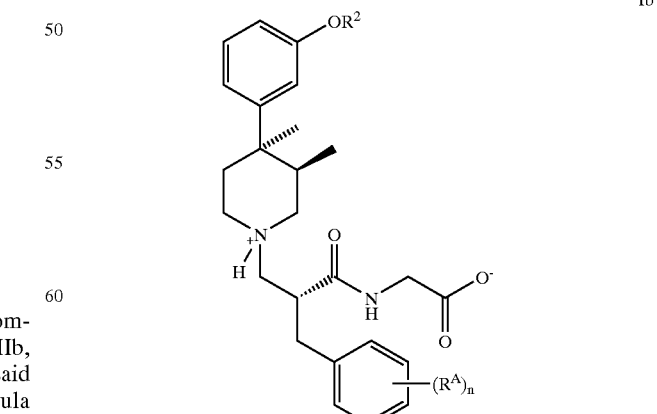

Ib wherein:

each R² is, independently, H or a hydroxyl protecting group;

each $R^A$ is, independently, halo, alkyl, halo-substituted alkyl, alkenyl, alkynyl, aryl, OR, C(O)R, C(O)OR, OC(O)R, NHC(O)R, NHSO₂R, SO₂NRR, aminocarbonyl, amino, nitro, cyano, or SR, wherein each R is, independently, H, alkyl, aryl, or aralkyl; and n is 0 to 5;

or a salt thereof;

comprising:

(a) preparing a compound of Formula Va, a compound of Formula Vb, or a mixture thereof:

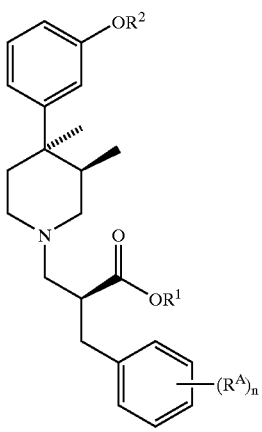

Va

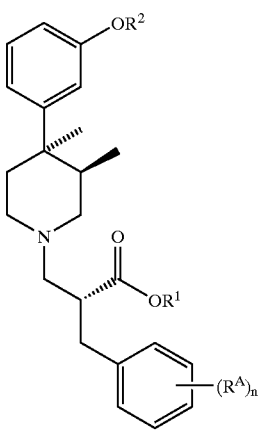

Vb wherein:

each R¹ is, independently, H, alkyl, aryl or aralkyl;

comprising providing a compound of Formula IIc, a compound of Formula IId, or a mixture thereof:

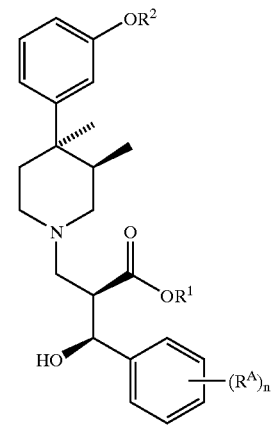

IIc

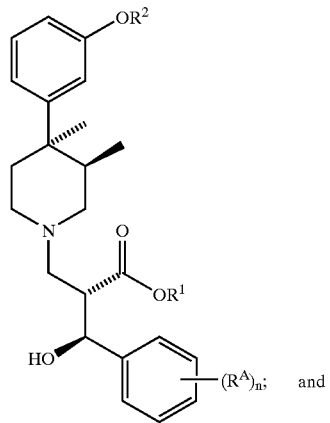

IId substituting the secondary hydroxyl group of said compound of Formula IIc, said compound of Formula IId, or said mixture thereof with hydrogen to provide said compound of Formula Va, said compound of Formula Vb, or said mixture thereof, wherein said substitution comprises hydrogenation, ionic dehydroxylation or radical deoxygenation;

(b) optionally converting —OR¹ of said compound of Formula Va, said compound of Formula Vb, or said mixture thereof to —X, where X is halo or —OC(O)R¹; and (c) selectively converting —OR¹, X, or —OC(O)R¹ of said compound of Formula Va, said compound of Formula Vb, or said mixture thereof, to —NHCH₂COOH, wherein said selective conversion comprises contacting the product from step (a) or optional step (b) with NH₂CH₂COOH or an acid addition salt, ester or derivative thereof.

10. A process of claim 9 wherein each R¹ is, independently, alkyl, aryl, or aralkyl.

11. A process of claim 10 wherein each R¹ is, independently, alkyl.

12. A process of claim 11 wherein R¹ is, independently, methyl or ethyl.

13. A process of claim 9 wherein R² is H.

14. A process of claim 9 wherein n is 0.

* * * * *